(12) United States Patent
McKew et al.

(10) Patent No.: US 7,557,135 B2
(45) Date of Patent: Jul. 7, 2009

(54) INHIBITORS OF CYTOSOLIC PHOSPHOLIPASE A$_2$

(75) Inventors: John C. McKew, Arlington, MA (US); Katherine L. Lee, Newton, MA (US); Lihren Chen, Bedford, MA (US); Richard Vargas, Brighton, MA (US); James D. Clark, Acton, MA (US); Cara Williams, Methuen, MA (US); Valerie Clerin, Watertown, MA (US); Suzana Marusic, Reading, MA (US); Kevin Pong, Robbinsville, NJ (US)

(73) Assignee: Wyeth, Madison, NJ (US)

( * ) Notice: Subject to any disclaimer, the term of this patent is extended or adjusted under 35 U.S.C. 154(b) by 231 days.

(21) Appl. No.: 11/442,199

(22) Filed: May 26, 2006

(65) Prior Publication Data

US 2007/0004719 A1    Jan. 4, 2007

Related U.S. Application Data

(60) Provisional application No. 60/685,564, filed on May 27, 2005.

(51) Int. Cl.
*A61K 31/404* (2006.01)
*C07D 209/14* (2006.01)

(52) U.S. Cl. ..................... 514/415; 548/507
(58) Field of Classification Search ............. 514/415; 548/507
See application file for complete search history.

(56) References Cited

U.S. PATENT DOCUMENTS

| | | | |
|---|---|---|---|
| 3,505,354 A | 4/1970 | Doebel et al. | |
| 3,629,284 A | 12/1971 | Yamamoto et al. | |
| 3,931,229 A | 1/1976 | Zinnes et al. | |
| 4,271,263 A | 6/1981 | Goettert | |
| 4,654,360 A | 3/1987 | Greenhouse et al. | |
| 4,894,386 A | 1/1990 | Brown et al. | |
| 5,081,145 A | 1/1992 | Guindon et al. | |
| 5,166,170 A | 11/1992 | Tegeler et al. | |
| 5,190,968 A | 3/1993 | Gillard et al. | |
| 5,206,377 A | 4/1993 | McAfee | |
| 5,212,195 A | 5/1993 | Clark et al. | |
| 5,229,516 A | 7/1993 | Musser et al. | |
| 5,288,743 A | 2/1994 | Brooks et al. | |
| 5,290,798 A | 3/1994 | Guillard et al. | |
| 5,314,908 A | 5/1994 | McAfee | |
| 5,322,776 A | 6/1994 | Knopf et al. | |
| 5,332,755 A | 7/1994 | Butler et al. | |
| 5,354,677 A | 10/1994 | Knopf et al. | |
| 5,380,739 A | 1/1995 | Clark et al. | |
| 5,420,289 A | 5/1995 | Musser et al. | |
| 5,424,329 A | 6/1995 | Boschelli et al. | |
| 5,482,960 A | 1/1996 | Berryman et al. | |
| 5,641,800 A | 6/1997 | Bach et al. | |
| 5,686,481 A | 11/1997 | Elliott et al. | |
| 6,500,853 B1 | 12/2002 | Seehra et al. | |
| 6,630,496 B1 | 10/2003 | Seehra et al. | |
| 6,635,771 B2 | 10/2003 | Mckew et al. | |
| 6,797,708 B2 | 9/2004 | Mckew et al. | |
| 6,891,065 B2 | 5/2005 | Wu et al. | |
| 6,984,735 B2 | 1/2006 | McKew et al. | |
| 7,282,594 B2 | 10/2007 | Michalak et al. | |
| 2003/0144282 A1* | 7/2003 | McKew et al. ............ 514/228.2 |
| 2003/0149209 A1 | 8/2003 | Inagaki et al. | |
| 2004/0186116 A1 | 9/2004 | Saunders et al. | |
| 2005/0049296 A1 | 3/2005 | Dehnhardt et al. | |
| 2005/0053600 A1 | 3/2005 | Lane | |
| 2005/0070723 A1 | 3/2005 | Dehnhardt et al. | |
| 2005/0148770 A1 | 7/2005 | Michalak et al. | |
| 2005/0159613 A1 | 7/2005 | Wu et al. | |
| 2006/0014759 A1 | 1/2006 | McKew et al. | |
| 2006/0041005 A1 | 2/2006 | Michalak et al. | |
| 2007/0004719 A1 | 1/2007 | McKew et al. | |

FOREIGN PATENT DOCUMENTS

| | | |
|---|---|---|
| CH | 48411 | 1/1970 |
| DE | 1816335 A1 | 7/1970 |
| DE | 4338770 A1 | 5/1996 |
| EP | 0337766 A1 | 10/1989 |
| EP | 0337767 A1 | 10/1989 |
| EP | 535926 A1 | 4/1993 |
| EP | 549916 A2 | 7/1993 |
| EP | 549916 A3 | 7/1993 |
| EP | 676959 A1 | 7/1994 |

(Continued)

OTHER PUBLICATIONS

Adediran et al., The Synthesis and Evaluation of Benzofuranones as .beta.-Lactamase Substrates, Bioorganic & Medicinal Chemistry, 9, 2001, pp. 1175-1183.

(Continued)

*Primary Examiner*—Rebecca L Anderson
*Assistant Examiner*—Jason Nolan
(74) *Attorney, Agent, or Firm*—Fish & Richardson P.C.

(57) ABSTRACT

This invention provides chemical inhibitors of the activity of various phospholipase enzymes, particularly cytosolic phospholipase A$_2$ enzymes (cPLA$_2$), more particularly including inhibitors of cytosolic phospholipase A$_2$ alpha enzymes (cPLA$_2$α). In some embodiments, the inhibitors have the Formula I:

I

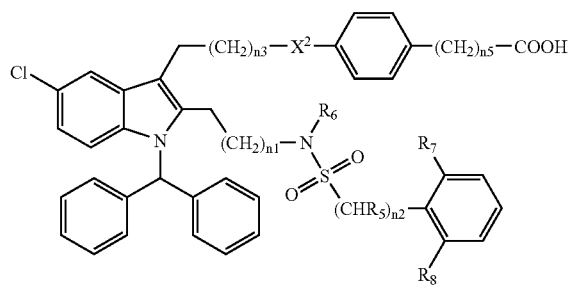

wherein the constituent variables are as defined herein.

2 Claims, 3 Drawing Sheets

FOREIGN PATENT DOCUMENTS

| | | | |
|---|---|---|---|
| EP | 0620215 A1 | | 10/1994 |
| EP | 922028 A1 | | 3/1998 |
| EP | 1583747 A2 | | 7/2004 |
| EP | 1648861 A1 | | 2/2005 |
| EP | 1697320 A1 | | 6/2005 |
| FR | 1492929 | | 7/1967 |
| PE | 000559-2006/OIN | * | 5/2006 |
| WO | WO 91/06537 A2 | | 5/1991 |
| WO | WO 93/23391 A1 | | 11/1993 |
| WO | WO 94/14434 A1 | | 7/1994 |
| WO | WO 95/13266 A1 | | 5/1995 |
| WO | WO 98/05637 A1 | | 2/1998 |
| WO | WO 98/08818 A1 | | 3/1998 |
| WO | WO 99/43651 A2 | | 9/1999 |
| WO | WO 99/43654 A2 | | 9/1999 |
| WO | WO 99/43672 A1 | | 9/1999 |
| WO | WO03/048122 | | 6/2003 |
| WO | WO 03/048122 | | 6/2003 |
| WO | WO 2004/060878 A2 | | 7/2004 |
| WO | WO 2004/060878 A3 | | 7/2004 |
| WO | WO 2005/012238 A1 | | 2/2005 |
| WO | WO 2005023201 A2 | | 3/2005 |
| WO | WO 2005023201 A3 | | 3/2005 |
| WO | WO 2005058820 A1 | | 6/2005 |
| WO | WO 2006023611 A1 | | 3/2006 |
| WO | WO2006/128142 | | 11/2006 |
| WO | WO 2006/128142 | | 11/2006 |

OTHER PUBLICATIONS

Bhatt et al., Nature Reviews, Drug Discovery vol. 2, 15-28, Jan. 2003.
Bonventure et al., et al., Nature 1997, 390: 622-625.
Burch et al., Proc. Natl. Acad. Sci. U.S.A., 84:6374-6378 (1989).
Chang et al, Biochem. Pharmacol., 36:2429-2436 (1987).
Chemical Abstract Service Registry No. 865200-20-0, "Benzoic acid, 4-[3-[5-chloro-1-(diphenylmethyl)-2-[2-[[[[2-(trifluoromethyl)phenyl]methyl]sulfonyl]amino]ethyl]-1H-indol-3-yl]propyl]-(9CI)," 1 page (Oct. 13, 2005).
Smith, Biochem. J., 259:315-324 (1989).
Uozumi et al. Role of Cytosolic Phospholipase $A_2$ in Allergic Response and Parturition, Nature, 390:618-622, (Dec. 11, 1997).
Wasserman, Hospital Practice, 15:49-58 (1988).
Xi et al., Functionalized Deep-Cavity Cavitands, J. Org. Chem. 1999, 64, pp. 9286-9288.
Written Opinion of the International Searching Authority and International Search Report for PCT/US2006/020847, 14 pages (Nov. 20, 2006).
Notification Concerning Transmittal of Copy of International Preliminary Report on Patentability for PCT/US2006/020847, 9 pages (Dec. 13, 2007).
Chung et al., Synthesis of 3-Fluoro-2-substituted amino-5,12-dihydro-5-oxobenzoxazolo[3,2-.alpha.]quinoline-6-carboxylic Acids Employing the Tandem Double Ring Closure Reaction of N-Acetyl-N-(2-hydroxyphenyl)anthranilic Acid as the Key Step, Tetrahedron vol. 51, No. 46, pp. 12549-12562, 1995, Elsevier Science Ltd, printed in Great Britain.
Clark et al., "Potential therapeutic uses of phospholipase $A_2$ inhibitors," *Expert Opin. Ther. Pat.*, 14:937-950 (2004).
Dennis, Drug Devel. Res., 10:205-220 (1987).
Dillard et al, Indole Inhibitors of Human Nonpancreatic Secretory Phospholipase A.sub.2. 1. Indole-3-acetamides, J. Med. Chem., 1996, vol. 39, No. 26, pp. 5119-5136.
Dillard et al., Indole Inhibitors of Human Nonpancreatic Secretory Phospholipase A.sub.2. 2. Indole-3-acetamides with Additional Functionality, J. Med.chem. 1996, vol. 39, No. 26, pp. 5137-5158.
Doebel et al., J. Med. Chem., 1972, vol. 15, No. 10, pp. 1081-1082.
Draheim et al., Indole Inhibitors of Human Nonpancreatic Secretory Phospholipase A.sub.2. 3 Indole-3-glyoxamides, J. Med. Chem 1996, vol. 39, No. 26, pp. 5159-5175.
Goodman et al., Self-Assembling, Chromogenic Receptors for the Recognition of Dicarboxylic Acid, J. Am. Chem. Soc., 1995, 117, pp. 8447-8455.
Jackson et al., Nature Reviews, Drug Discovery vol. 2, 1-15, Oct. 2003.
Kando et al, Biochem. Biophys. Res. Comm., 163:42-48 (1989).
Kramer et al, J. Biol. Chem., 264:5768-5775 (1989).
Langer et al., Synthesis of High-specific-radioactivity 4- and 6-[.sup.18F]fluorometaraminol-PET Tracers for the Adrenergic Nervous System of the Heart, Bioorganic & Medicinal Chemistry, 9, 2001, pp. 677-694.
Leslie et al, Biochem. Biophys. Acta., 963:476-492 (1988).
Nieswandt et al., J. Thrombosis and Haemostasis, 3: 1725-1736 (2005).
Roy et al., Further Studies on Anti-Inflammatory Activity of Two Potent Indan-1-Acetic Acids, Ind. J. Physiol. Pharmac., Jul.-Sep. 1982, vol. 28, No. 3, pp. 207-214.
Samuelson et al., Science, 237:1171-76 (1987).
Schevitz et al., Nature Structural Biology, vol. 2, No. 2, Jun. 1995, pp. 458-465.
Seilhamer et al, J. Biol. Chem., 264:5335-5338 (1989).
Clark, James D. et al., "Potential therapeutic uses of phospholipase $A_2$ inhibitors," *Expert Opin. Ther. Pat.*, 14:937-950 (2004).
International Search Report for PCT/US2006/020847, 5 pages (Nov. 20, 2006).
Written Opinion of the International Searching Authority for PCT/US2006/020847, 7 pages (Nov. 20, 2006).
Behnke, Mark L. et al., "Indole Based Inhibitors of $cPLA_2\alpha$: Phenylsulfonamides", (2005).
Clark, James D., "Discovery of Anti-Inflammatory $cPLA_2\alpha$ Inhibitors" FASEB Conference Phospholipid Metabolism, (Jul. 21, 2008).
"Discovery of Anti-Inflammaotry $cPLA_2\alpha$ Inhibitors", Inflammation & Immune Diseases Drug Discovery & Development Summit, (Mar. 14-15, 2005).
Lee, Katherine L. et al., "Indole Phenyl Sulfonamide $CPLA_2\alpha$ Inhibitors for the Treatment of Inflammation" Mar. 30, 2006).
Lee, Katherine L. et al., "The Discovery of $cPLA_2\alpha$ Inhibotors with Efficacy in Animal Models of Arthritis, Asthma, Multiple Sclerosis, Thrombosis and Atherosclerosis", (Aug. 2007).
McKew, John C. et al., "Discovery of a New Class of Anti-Inflammatory: Indole $cPLA_2\alpha$ Inhibitors", (May 2004).
McKew, John C. et al., "Indole Benzyl Sulfonamide $cPLA_2\alpha$ Inhibitors: Optimization and Efficacy in Inflammatory Models", (2006).
McKew, John et al., "The Discovery $cPLA_2\alpha$ Inhibitors that are Efficacious in In Vivo Models of Arthritis, Stroke, and Atherothrombosis", (2007).
McKew, John, "Discovery & Characterization of Giripladib: A first in Class cPLAα Inhibitor", (Nov. 2, 2007).
McKew, John, "Discovery & Characterization of Giripladib: A first in Class $cPLA_2\alpha$ Inhibitor", (Feb. 20, 2008).
Ramarao, Manjunath, "Characterization of $cPLA_2\alpha$ Inhibitors by Microcalorimetry", (2007).

* cited by examiner

Evaluation of Examples 14 and 25 in the
Rat Ferric Chloride Induced Arterial Thrombosis Model Rat FeCl$_3$ induced thrombosis: TXB$_2$ levels

INHIBITORS OF CYTOSOLIC PHOSPHOLIPASE $A_2$

CROSS REFERENCE TO RELATED APPLICATIONS

This application claims priority benefit of U.S. Provisional Application Ser. No. 60/685,564, filed May 27, 2005, the entire content of which is incorporated herein by reference.

FIELD OF THE INVENTION

The present invention relates to chemical inhibitors of the activity of various phospholipase enzymes, particularly cytosolic phospholipase $A_2$ enzymes ($cPLA_2$), more particularly including inhibitors of cytosolic phospholipase $A_2$ alpha enzymes ($cPLA_2\alpha$).

BACKGROUND OF THE INVENTION

Leukotrienes and prostaglandins are important mediators of inflammation, each of which contributes to the development of an inflammatory response in a different way. Leukotrienes recruit inflammatory cells such as neutrophils to an inflamed site, promote the extravasation of these cells and stimulate release of superoxide and proteases which damage the tissue. Leukotrienes also play a pathophysiological role in the hypersensitivity experienced by asthmatics [See, e.g. B. Samuelson et al., Science, 237:1171-76 (1987)]. Prostaglandins enhance inflammation by increasing blood flow and therefore infiltration of leukocytes to inflamed sites. Prostaglandins also potentiate the pain response induced by stimuli.

Prostaglandins and leukotrienes are unstable and are not stored in cells, but are instead synthesized [W. L. Smith, Biochem. J., 259:315-324 (1989)] from arachidonic acid in response to stimuli. Prostaglandins are produced from arachidonic acid by the action of COX-1 and COX-2 enzymes. Arachidonic acid is also the substrate for the distinct enzyme pathway leading to the production of leukotrienes.

Arachidonic acid, which is fed into these two distinct inflammatory pathways, is released from the sn-2 position of membrane phospholipids by phospholipase $A_2$ enzymes (hereinafter $PLA_2$). The reaction catalyzed by $PLA_2$ is believed to represent the rate-limiting step in the process of lipid mediator biosynthesis, including but not limited to the production of inflammatory prostaglandins and leukotrienes. When the phospholipid substrate of $PLA_2$ is of the phosphotidyl choline class with an ether linkage in the sn-1 position, the lysophospholipid produced is the immediate precursor of platelet activating factor (hereafter called PAF), another potent mediator of inflammation [S. I. Wasserman, Hospital Practice, 15:49-58 (1988)].

Most anti-inflammatory therapies have focused on preventing production of either prostaglandins or leukotrienes from these distinct pathways, but not on all of them. For example, ibuprofen, aspirin, and indomethacin are all NSAIDs which inhibit the production of prostaglandins by COX-1/COX-2 inhibition, but have no direct effect on the inflammatory production of leukotrienes from arachidonic acid in the other pathways. Conversely, zileuton inhibits only the pathway of conversion of arachidonic acid to leukotrienes, without directly affecting the production of prostaglandins. None of these widely-used anti-inflammatory agents affects the production of PAF.

Consequently the direct inhibition of the activity of $PLA_2$ has been suggested as a useful mechanism for a therapeutic agent, i.e., to interfere with the inflammatory response. [See, e.g., J. Chang et al, Biochem. Pharmacol., 36:2429-2436 (1987)].

A family of $PLA_2$ enzymes characterized by the presence of a secretion signal sequenced and ultimately secreted from the cell have been sequenced and structurally defined. These secreted $PLA_2$s have an approximately 14 kD molecular weight and contain seven disulfide bonds which are necessary for activity. These $PLA_2$ are found in large quantities in mammalian pancreas, bee venom, and various snake venom. [See, e.g., references 13-15 in Chang et al, cited above; and E. A. Dennis, Drug Devel. Res., 10:205-220 (1987).] However, the pancreatic enzyme is believed to serve a digestive function and, as such, should not be important in the production of the inflammatory mediators whose production must be tightly regulated.

The primary structure of the first human non-pancreatic $PLA_2$ has been determined. This non-pancreatic $PLA_2$ is found in platelets, synovial fluid, and spleen and is also a secreted enzyme. This enzyme is a member of the aforementioned family. [See, J. J. Seilhamer et al, J. Biol. Chem., 264:5335-5338 (1989); R. M. Kramer et al, J. Biol. Chem., 264:5768-5775 (1989); and A. Kando et al, Biochem. Biophys. Res. Comm., 163:42-48 (1989)]. However, it is doubtful that this enzyme is important in the synthesis of prostaglandins, leukotrienes and PAF, since the non-pancreatic $PLA_2$ is an extracellular protein which would be difficult to regulate, and the next enzymes in the biosynthetic pathways for these compounds are intracellular proteins. Moreover, there is evidence that $PLA_2$ is regulated by protein kinase C and G proteins [R. Burch and J. Axelrod, Proc. Natl. Acad. Sci. U.S.A., 84:6374-6378 (1989)] which are cytosolic proteins which must act on intracellular proteins. It would be impossible for the non-pancreatic $PLA_2$ to function in the cytosol, since the high reduction potential would reduce the disulfide bonds and inactivate the enzyme.

A murine $PLA_2$ has been identified in the murine macrophage cell line, designated RAW 264.7. A specific activity of 2 μmols/min/mg, resistant to reducing conditions, was reported to be associated with the approximately 60 kD molecule. However, this protein was not purified to homogeneity. [See, C. C. Leslie et al, Biochem. Biophys. Acta., 963:476-492 (1988)]. The references cited above are incorporated by reference herein for information pertaining to the function of the phospholipase enzymes, particularly $PLA_2$.

A cytosolic phospholipase $A_2$ alpha (hereinafter "$cPLA_2\alpha$") has also been identified and cloned. See, U.S. Pat. Nos. 5,322,776 and 5,354,677, which are incorporated herein by reference as if fully set forth. The enzyme of these patents is an intracellular $PLA_2$ enzyme, purified from its natural source or otherwise produced in purified form, which functions intracellularly to produce arachidonic acid in response to inflammatory stimuli.

Bioactive metabolites of arachidonic acid, the eicosanoids, are recognized as important modulators of platelet signaling. Inhibitors of the eicosaniod pathway (e.g., aspirin) reduce the formation of thromboxane $A_2$ ($TXA_2$), a labile and potent platelet agonist, resulting in depression of platelet function, thrombus formation, and proven clinical benefit in reducing morbidity and mortality.

Platelets play a central role in several biological processes, including thrombosis. [See S. P. Jackson and S. M. Schoenwaelder, Nature Reviews, Drug Discovery Vol. 2, 1-15, October 2003; D. L. Bhatt and E. J. Topol, Nature Reviews, Drug Discovery Vol. 2, 15-28, January 2003]. Accordingly, recent efforts have been made to characterize platelet receptors and signaling pathways. In addition, a number of rodent models have been developed to enable the study of potential therapeutics in thrombosis. [See B. Nieswandt et al., J. Thrombosis and Haemostasis, 3: 1725-1736 (2005).

Inhibitors of cytosolic phospholipase $A_2$ are disclosed in U.S. Pat. No. 6,797,708, which is incorporated herein by reference in its entirety.

Now that several phospholipase enzymes have been identified, it would be desirable to identify chemical inhibitors of the action of specific phospholipase enzymes, which inhibitors could be used to treat inflammatory conditions, particularly where inhibition of production of prostaglandins, leukotrienes and PAF are all desired results. There remains a need in the art for an identification of such anti-inflammatory agents for therapeutic use in a variety of disease states.

SUMMARY OF THE INVENTION

In some embodiments, the invention provides compounds having the Formula I:

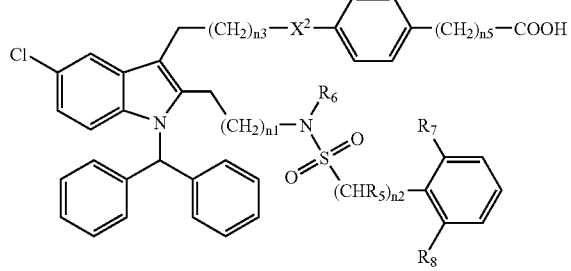

I wherein:
  $n_1$ is 1 or 2;
  $n_2$ is 1 or 2;
  $n_3$ is 1 or 2;
  $n_5$ is 0, 1 or 2;
  $X^2$ is a bond, O, —$CH_2$— or $SO_2$;
  each $R_5$ is independently H or $C_{1-3}$ alkyl;
  $R_6$ is H or $C_{1-6}$ alkyl;
  $R_7$ is selected from the group consisting of OH, benzyloxy, $CH_3$, $CF_3$, $OCF_3$, $C_{1-3}$ alkoxy, halogen, COH, CO($C_{1-3}$ alkyl), CO(O$C_{1-3}$ alkyl), quinoline-5-yl, quinoline-8-yl, 3,5-dimethylisoxazol-4-yl, thiophene-3-yl, pyridin-4-yl, pyridine-3-yl, —$CH_2$-Q, and phenyl optionally substituted by from one to three independently selected $R_{30}$ groups;
  $R_8$ is selected from the group consisting of H, OH, $NO_2$, $CF_3$, $OCF_3$, $C_{1-3}$ alkoxy, halogen, CO($C_{1-3}$ alkyl), CO(O$C_{1-3}$ alkyl), quinoline-5-yl, quinoline-8-yl, 3,5-dimethylisoxazol-4-yl, thiophene-3-yl, —$CH_2$-Q, and phenyl substituted by from one to three independently selected $R_{30}$ groups;
  Q is OH, dialkylamino,

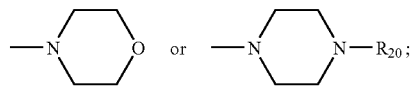

$R_{20}$ is selected from the group consisting of H, $C_{1-3}$ alkyl and CO($C_{1-3}$ alkyl); and
  $R_{30}$ is selected from the group consisting of dialkylamino, CN and $OCF_3$; provided that:

a) when each $R_5$ is H, $R_6$ is H, $n_5$ is 0, and $R_8$ is H, then $R_7$ cannot be chlorine;
b) when each $R_5$ is H, $R_6$ is H, $n_5$ is 0, $X^2$ is O or —$CH_2$—, and $R_8$ is H, then $R_7$ cannot be $CH_3$;
c) when each $R_5$ is H, and $R_6$ is H, then $R_7$ and $R_8$ cannot both be fluorine;
d) when each $R_5$ is H, $R_6$ is H, and $X^2$ is O, then $R_7$ and $R_8$ cannot both be chlorine;
e) when each $R_5$ is H, $R_6$ is H, $X^2$ is O, and $R_8$ is $NO_2$, then $R_7$ cannot be fluorine; and
f) when each $R_5$ is H, $R_6$ is H, $X^2$ is $SO_2$, and $R_8$ is H, then $R_7$ cannot be fluorine or chlorine.

In some preferred embodiments, compounds are provided having the Formula II:

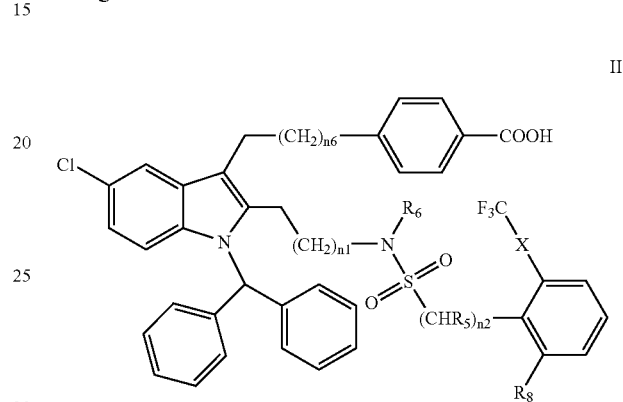

II wherein:
  X is a bond or O;
  $n_1$ is 1 or 2;
  $n_2$ is 1 or 2;
  $n_6$ is 1 or 2;
  $R_5$ is H or $CH_3$;
  $R_6$ is H or $C_{1-6}$ alkyl; and
  $R_8$ is selected from the group consisting of H, OH, $NO_2$, $CF_3$, $OCF_3$, $OCH_3$, halogen, $COCH_3$, $COOCH_3$, dimethylamino, diethylamino and CN.

The present invention also provides methods of treating inflammation caused or potentiated by prostaglandins, leukotrienes, or platelet activation factor, in a mammal, the method comprising administering to a mammal in need thereof a pharmaceutically acceptable amount of a compound of the invention, or a pharmaceutically acceptable salt thereof.

The present invention further provides methods of treating pain caused or potentiated by prostaglandins, leukotrienes, or platelet activation factor, in a mammal, the method comprising administering to a mammal in need thereof a pharmaceutically acceptable amount of a compound of the invention, or a pharmaceutically acceptable salt thereof.

The present invention further provides methods of treating or preventing a disease or disorder in a mammal, or preventing progression of symptoms such a disease or disorder, wherein the disease or disorder is selected from the group consisting of asthma, stroke, atherosclerosis, multiple sclerosis, Parkinson's disease, arthritic disorders, rheumatic disorders, central nervous system damage resulting from stroke, central nervous system damage resulting from ischemia, central nervous system damage resulting from trauma, inflammation caused or potentiated by prostaglandins, inflammation caused or potentiated by leukotrienes, pain, and inflammation caused or potentiated by platelet activation factor, in a mammal, the method comprising administering to a mammal in need thereof a pharmaceutically acceptable amount of a compound of the invention, or a pharmaceutically acceptable salt thereof.

The present invention also provides methods for treating or preventing venous or arterial thrombosis in a mammal, or preventing progression of symptoms of thrombosis, the method comprising administering to a mammal in need thereof a pharmaceutically acceptable amount of a compound of the invention, or a pharmaceutically acceptable salt thereof. In some embodiments, the thrombosis is atherothrombosis.

The present invention also provides pharmaceutical compositions comprising a compound of the invention, or a pharmaceutically acceptable salt thereof, and a pharmaceutically acceptable carrier.

Also provided in accordance with the present invention are pharmaceutically acceptable salts, and prodrugs, of the compounds disclosed herein.

DETAILED DESCRIPTION OF THE INVENTION

Figure 1:
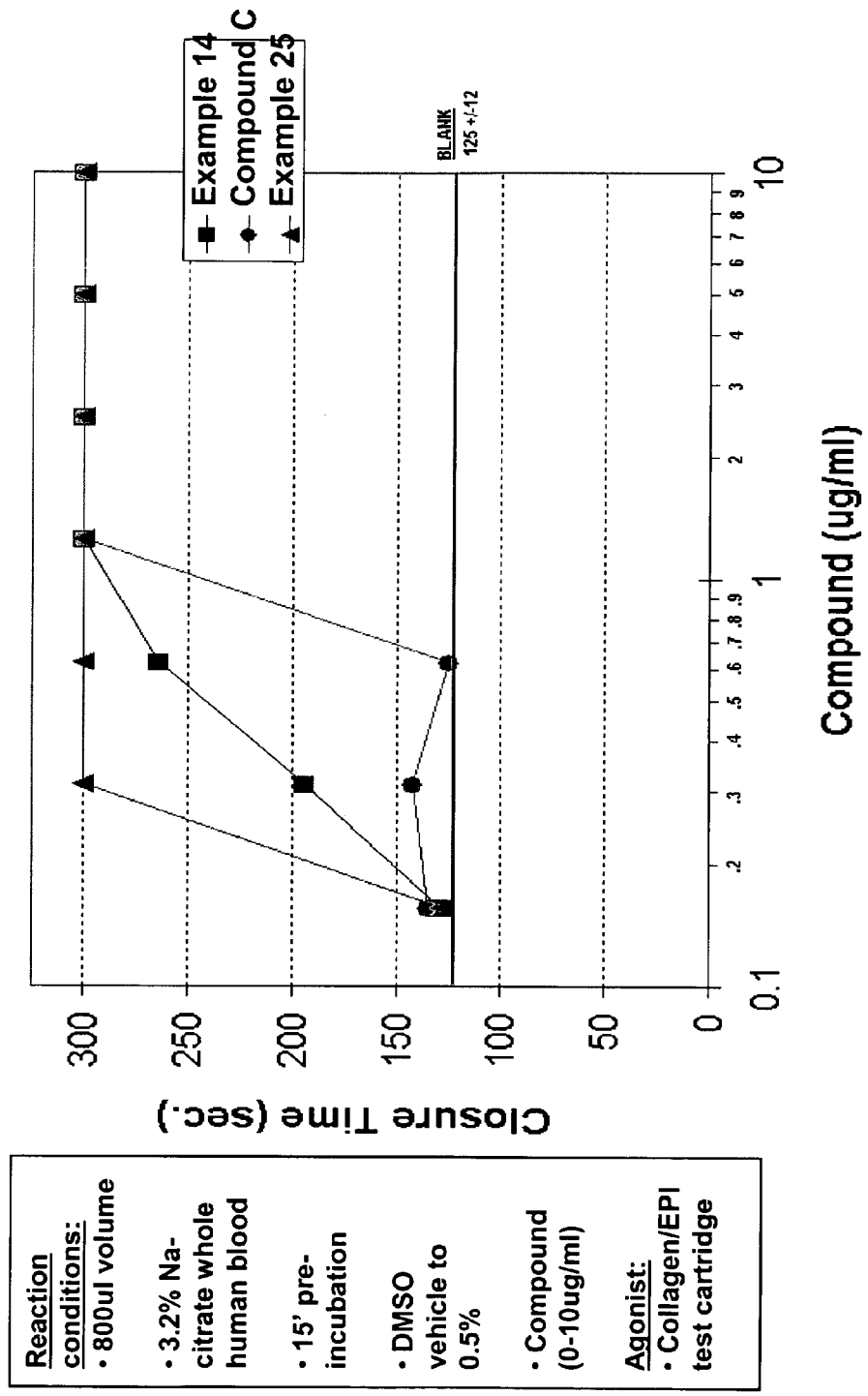
FIG. 1 shows the in vitro inhibition of platelet aggregation in human blood by the compounds of Examples 14 and 25, as determined by the platelet function analyzer (PFA-100®).

In some embodiments, the invention provides compounds having the Formula I:

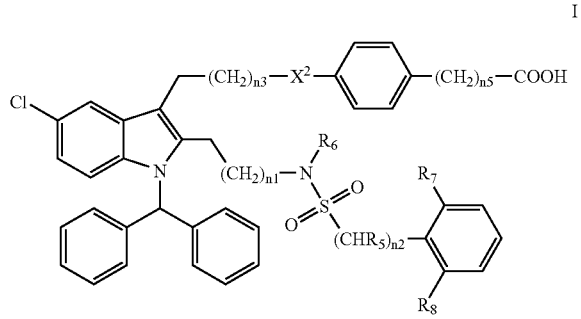

I wherein:
$n_1$ is 1 or 2;
$n_2$ is 1 or 2;
$n_3$ is 1 or 2;
$n_5$ is 0, 1 or 2;
$X^2$ is a bond, O, —$CH_2$— or $SO_2$;
each $R_5$ is independently H or $C_{1-3}$ alkyl;
$R_6$ is H or $C_{1-6}$ alkyl;
$R_7$ is selected from the group consisting of OH, benzyloxy, $CH_3$, $CF_3$, $OCF_3$, $C_{1-3}$ alkoxy, halogen, COH, CO($C_{1-3}$ alkyl), CO(O$C_{1-3}$ alkyl), quinoline -5-yl, quinoline-8-yl, 3,5-dimethylisoxazol-4-yl, thiophene-3-yl, pyridin-4-yl, pyridine-3-yl, —$CH_2$-Q, and phenyl optionally substituted by from one to three independently selected $R_{30}$ groups;

$R_8$ is selected from the group consisting of H, OH, $NO_2$, $CF_3$, $OCF_3$, $C_{1-3}$ alkoxy, halogen, CO($C_{1-3}$ alkyl), CO(O$C_{1-3}$ alkyl), quinoline-5-yl, quinoline-8-yl, 3,5-dimethylisoxazol-4-yl, thiophene-3-yl, —$CH_2$-Q, and phenyl substituted by from one to three independently selected $R_{30}$ groups;

Q is OH, alkylamino,

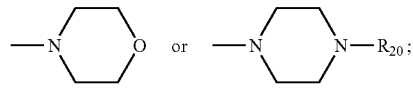

$R_{20}$ is selected from the group consisting of H, $C_{1-3}$ alkyl and CO($C_{1-3}$ alkyl); and
$R_{30}$ is selected from the group consisting of dialkylamino, CN and $OCF_3$;

provided that:
a) when each $R_5$ is H, $R_6$ is H, $n_5$ is 0, and $R_8$ is H, then $R_7$ cannot be chlorine;
b) when each $R_5$ is H, $R_6$ is H, $n_5$ is 0, $X^2$ is O or —$CH_2$—, and $R_8$ is H, then $R_7$ cannot be $CH_3$;
c) when each $R_5$ is H, and $R_6$ is H, then $R_7$ and $R_8$ cannot both be fluorine;
d) when each $R_5$ is H, $R_6$ is H, and $X^2$ is O, then $R_7$ and $R_8$ cannot both be chlorine;
e) when each $R_5$ is H, $R_6$ is H, $X^2$ is O, and $R_8$ is $NO_2$, then $R_7$ cannot be fluorine; and
f) when each $R_5$ is H, $R_6$ is H, $X^2$ is $SO_2$, and $R_8$ is H, then $R_7$ cannot be fluorine or chlorine.

In some embodiments, $X^2$ is $CH_2$. In some further embodiments, $n_3$ is 1. In some further embodiments, $n_1$ is 1. In still further embodiments, $n_2$ is 1.

In some embodiments, $n_3$ is 1; $n_1$ is 1; and $n_2$ is 1. In some such embodiments, $R_6$ is H. In some such embodiments, $n_3$ is 1; $n_1$ is 1; $n_2$ is 1; $R_6$ is H; $R_7$ is selected from the group consisting of $CH_3$, $CF_3$, $OCF_3$, halogen, $COOCH_3$, COH, $CH_2OH$, diethylaminomethyl, quinoline-5-yl, quinoline-8-yl, 3,5-dimethylisoxazol-4-yl, thiophene-3-yl, pyridin-4-yl, pyridine-3-yl, phenyl, 4-dimethylamino-phen-1-yl, 2-trifluoromethoxy-phen-1-yl, 2-cyano-phen-1-yl, morpholine-1-yl-methyl, piperazine-1-yl methyl, 4-acetyl-piperazine-1-yl methyl, and 4-methyl-piperazine-1-yl methyl; and $R_8$ is selected from the group consisting of H, halogen, $CF_3$ and $NO_2$. In some such embodiments, $R_5$ is H. In some further embodiments, $R_5$ is $CH_3$.

In some embodiments of the compounds of Formula I, $X^2$ is O. In some such embodiments, $n_3$ is 1. In some such embodiments, $n_1$ is 1. In some such embodiments, $n_2$ is 1. In some embodiments, $R_6$ is H. In some such embodiments, $n_3$ is 1; $n_1$ is 1; and $n_2$ is 1. In some such embodiments, $n_3$ is 1; $n_1$ is 1; $n_2$ is 1; $R_6$ is H; $R_7$ is selected from the group consisting of benzyloxy, OH, halogen, $CH_3$ and $CF_3$; and $R_8$ is selected from the group consisting of H, halogen, and $NO_2$. In some such embodiments, $R_5$ is H. In some further embodiments, $R_5$ is $CH_3$. In some preferred embodiments, $R_7$ is $CF_3$, and $R_8$ is H.

In some embodiments, $X^2$ is $SO_2$. In some such embodiments, $n_5$ is 2. In some further such embodiments, $n_3$ is 1. In some further such embodiments, $n_1$ is 1. In some further such embodiments, $n_2$ is 1. In some embodiments, $R_6$ is H. In some further such embodiments, $n_3$ is 1; $n_1$ is 1; and $n_2$ is 1. In some embodiments, $X^2$ is $SO_2$; $n_3$ is 1; $n_1$ is 1; $n_2$ is 1; $R_6$ is H; $R_7$ is $CF_3$; and $R_8$ is H.

In some embodiments, $n_1$ is 1; $n_2$ is 1 or 2; $n_3$ is 1, $n_5$ is 0; $X^2$ is $CH_2$, each $R_5$ and each $R_6$ is H; and $R_7$ and $R_8$ are independently selected from the group consisting of H, F, $CF_3$, $OCF_3$, OH, quinoline-5-yl and quinoline-8-yl, provided that $R_7$ and $R_8$ are not both H.

In some preferred embodiments, compounds are provided having the Formula II:

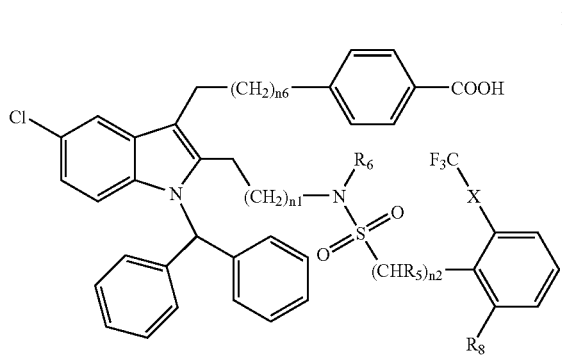

wherein:
X is a bond or O;
$n_1$ is 1 or 2;
$n_2$ is 1 or 2;
$n_6$ is 1 or 2;
$R_5$ is H or $CH_3$;
$R_6$ is H or $C_{1-6}$ alkyl; and
$R_8$ is selected from the group consisting of H, OH, $NO_2$, $CF_3$, $OCF_3$, $OCH_3$, halogen, $COCH_3$, $COOCH_3$, dimethylamino, diethylamino and CN.

In some embodiments, $n_1$ is 1. In some further embodiments, $n_2$ is 1. In some further embodiments, $n_6$ is 2. In some further embodiments, $R_5$ is H. In some further embodiments, $R_6$ is H. In some further embodiments, $n_1$ is 1; $n_2$ is 1; and $n_6$ is 2.

In some preferred embodiments, $R_5$ is H; $R_6$ is H; $n_1$ is 1, $n_2$ is 1; and $n_6$ is 2. In some such embodiments, $R_8$ is selected from the group consisting of H, $CF_3$, $OCF_3$ and halogen, preferably H.

The present invention also provides methods of treating inflammation caused or potentiated by prostaglandins, leukotrienes, or platelet activation factor, in a mammal, the method comprising administering to a mammal in need thereof a pharmaceutically acceptable amount of a compound of the invention, or a pharmaceutically acceptable salt thereof.

The present invention further provides methods of treating pain caused or potentiated by prostaglandins, leukotrienes, or platelet activation factor, in a mammal, the method comprising administering to a mammal in need thereof a pharmaceutically acceptable amount of a compound of the invention, or a pharmaceutically acceptable salt thereof.

The present invention also provides methods for treating or preventing venous or arterial thrombosis in a mammal, or preventing progression of symptoms of thrombosis, the method comprising administering to a mammal in need thereof a pharmaceutically acceptable amount of a compound of the invention, or a pharmaceutically acceptable salt thereof. In some embodiments, the thrombosis is atherothrombosis.

The present invention also provides pharmaceutical compositions comprising a compound of the invention, or a pharmaceutically acceptable salt thereof, and a pharmaceutically acceptable carrier.

Also provided in accordance with the present invention are pharmaceutically acceptable salts, and prodrugs, of the compounds disclosed herein.

Compounds of the present invention may be used in a pharmaceutical composition when combined with a pharmaceutically acceptable carrier. Such a composition may also contain (in addition to a compound or compounds of the present invention and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition may further contain other anti-inflammatory agents. Such additional factors and/or agents may be included in the pharmaceutical composition to produce a synergistic effect with compounds of the present invention, or to minimize side effects caused by the compound of the present invention.

The pharmaceutical compositions of the invention may be in the form of a liposome or micelles in which compounds of the present invention are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

As used herein, the terms "pharmaceutically effective amount" or "therapeutically effective amount" as used herein means the total amount of each active component of the pharmaceutical composition or method that is sufficient to show a meaningful patient benefit, i.e., treatment, healing, prevention, inhibition or amelioration of a physiological response or condition, such as an inflammatory condition or pain, or an increase in rate of treatment, healing, prevention, inhibition or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

Each of the methods of treatment or use of the present invention, as described herein, comprises administering to a mammal in need of such treatment or use a pharmaceutically or therapeutically effective amount of a compound of the present invention, or a pharmaceutically acceptable salt form thereof. Compounds of the present invention may be administered in accordance with the method of the invention either alone or in combination with other therapies such as treatments employing other anti-inflammatory agents, cytokines, lymphokines or other hematopoietic factors. When co-administered with one or more other anti-inflammatory agents, cytokines, lymphokines or other hematopoietic factors, compounds of the present invention may be administered either simultaneously with the other anti-inflammatory agent(s), cytokine(s), lymphokine(s), other hematopoietic factor(s), thrombolytic or anti-thrombotic factors, or sequentially. If administered sequentially, the attending physician will decide on the appropriate sequence of administering compounds of the present invention in combination with other anti-inflammatory agent(s), cytokine(s), lymphokine(s), other hematopoietic factor(s), thrombolytic or anti-thrombotic factors.

Administration of compounds of the present invention used in the pharmaceutical composition or to practice the method of the present invention can be carried out in a variety of conventional ways, such as oral ingestion, inhalation, or cutaneous, subcutaneous, or intravenous injection.

When a therapeutically effective amount of compounds of the present invention is administered orally, compounds of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% compound of the present invention, and preferably from about 10% to 90% compound of the present invention. When administered in liquid form, a liquid carrier such as water, petroleum, oils of animal or plant origin such as peanut oil, mineral oils, phospholipids, tweens, triglycerides, including medium chain triglycerides, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of compound of the present invention, and preferably from about 1 to 50% compound of the present invention.

When a therapeutically effective amount of compounds of the present invention is administered by intravenous, cutaneous or subcutaneous injection, compounds of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to compounds of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of compound(s) of the present invention in the pharmaceutical composition of the present invention will depend upon the nature and severity of the condition being treated, and on the nature of prior treatments the patient has undergone. Ultimately, the attending physician will decide the amount of compound of the present invention with which to treat each individual patient. Initially, the attending physician will administer low doses of compound of the present invention and observe the patient's response. Larger doses of compounds of the present invention may be administered until the optimal therapeutic effect is obtained for the patient, and at that point the dosage is not increased further. It is contemplated that the various pharmaceutical compositions used to practice the method of the present invention should contain about 0.1 µg to about 100 mg (preferably about 0.1 mg to about 50 mg, more preferably about 1 mg to about 2 mg) of compound of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the compounds of the present invention will be in the range of 12 to 24 hours of continuous intravenous administration. Ultimately the attending physician will decide on the appropriate duration of intravenous therapy using the pharmaceutical composition of the present invention.

A lipid based oral formulation of this invention has been prepared by blending 50% PHOSAL® 53MCT (American Lecithin Company), 5% Polysorbate 80, 15% LABRASOL® Caprylocaproyl macrogol-8 glycerides (Gattefosse Corp.), 15% Propylene Carbonate and 15% active cPLA2 inhibiting compound(s) of this invention, each percentage listed being by weight.

Pharmaceutically acceptable salts of the compounds of Formula (I) having an acidic moiety can be formed from organic and inorganic bases. Suitable salts with bases are, for example, metal salts, such as alkali metal or alkaline earth metal salts, for example sodium, potassium, or magnesium salts; or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethyl-propylamine, or a mono-, di-, or trihydroxy lower alkylamine, for example mono-, di- or triethanolamine.

The present invention also includes prodrugs of the compounds described herein. As used herein, "prodrug" refers to a moiety that releases a compound of the invention when administered to a mammalian subject. Prodrugs can be prepared by modifying functional groups present in the compounds in such a way that the modifications are cleaved, either in routine manipulation or in vivo, to the parent compounds. Examples of prodrugs include compounds of the invention as described herein that contain one or more molecular moieties appended to a hydroxyl, amino, sulfhydryl, or carboxyl group of the compound, and that when administered to a mammalian subject, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl) and the like. Alkyl groups can contain from 1 to about 20, 1 to about 10, 1 to about 8, 1 to about 6, 1 to about 4, or 1 to about 3 carbon atoms. In some embodiments, alkyl groups can be substituted with up to four substituent groups, as described below. As used herein, the term "lower alkyl" is intended to mean alkyl groups having up to six carbon atoms.

As used herein, "hydroxy" or "hydroxyl" refers to OH.

As used herein, "halo" or "halogen" includes fluoro, chloro, bromo, and iodo.

As used herein, "cyano" refers to CN.

As used herein, "alkoxy" refers to an —O-alkyl group. Example alkoxy groups include methoxy, ethoxy, propoxy (e.g., n-propoxy and isopropoxy), t-butoxy, and the like. An alkoxy group can contain from 1 to about 20, 1 to about 10, 1 to about 8, 1 to about 6, 1 to about 4, or 1 to about 3 carbon atoms.

As used herein, "benzyloxy" refers to an —O-benzyl group.

At various places in the present specification substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, propyl, isopropyl, n-butyl, sec-butyl, isobutyl, etc.

The compounds of the present invention can contain an asymmetric atom (also referred as a chiral center), and some of the compounds can contain one or more asymmetric atoms or centers, which can thus give rise to optical isomers (enantiomers) and diastereomers. The present invention includes such optical isomers (enantiomers) and diastereomers (geometric isomers); as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, and include, but are not limited to, diastereomeric salt formation, kinetic resolution, and asymmetric synthesis. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of present invention can be conveniently prepared in accordance with the procedures outlined in the schemes below, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds of the invention.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatograpy (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Although not wishing to be limited to any source, publications and literatures such as WO 200044723; Li, J. P.; Newlander, K. A.; Yellin, T. O. *Synthesis*, 1988, 73-76; Gilchrist, T. L.; Roberts, T. G. *J. Chem. Soc. Perkin. Trans* 1 1983, 1283-1292 are useful and recognized references of organic synthesis known to those in the art. Each of the foregoing is incorporated herein by reference in its entirety.

The invention compounds are prepared using conventional techniques known to those skilled in the art of organic synthesis. The starting materials used in preparing the compounds of the invention are known, made by known methods or are commercially available.

Those skilled in the art of organic synthesis will recognize that the nature and order of the synthetic steps presented may be varied for the purpose of optimizing the formation of the compounds of the invention.

EXAMPLES

Preparation of Compounds of the Invention

The following describes the preparation of representative compounds of this invention in greater detail. The following examples are offered for illustrative purposes, and are not intended to limit the invention in any manner. Those of skill in the art will readily recognize a variety of noncritical parameters which can be changed or modified to yield essentially the same results.

Mass spectral data is reported as the mass-to-charge ratio, m/z; and for high resolution mass spectral data, the calculated and experimentally found masses, [M+H]$^+$, for the neutral formulae M are reported. Nuclear magnetic resonance data is reported as δ in parts per million (ppm) downfield from the standard, tetramethylsilane; along with the solvent, nucleus, and field strength parameters. The spin-spin homonuclear coupling constants are reported as J values in hertz; and the multiplicities are reported as a: s, singlet; d, doublet; t, triplet; q, quartet; quintet; or br, broadened.

General Synthetic Scheme(s) for Preparation of Compounds

Compounds of the invention can be prepared by the procedures of Methods A-E, shown below:

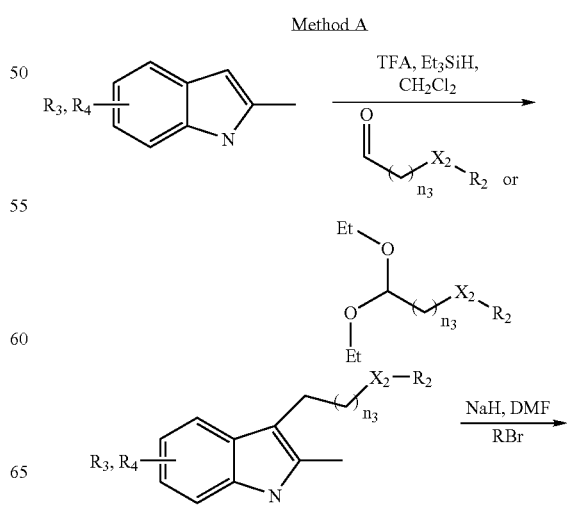

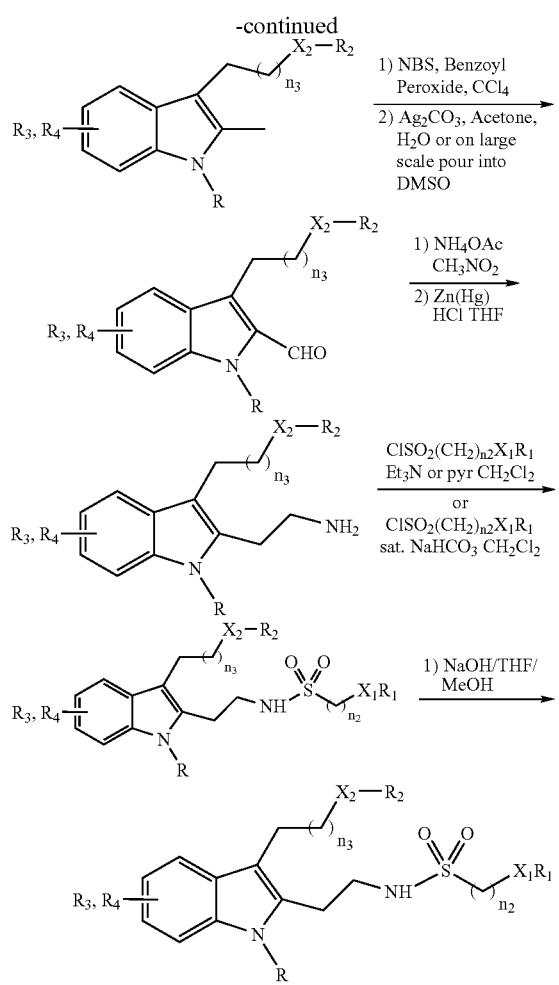

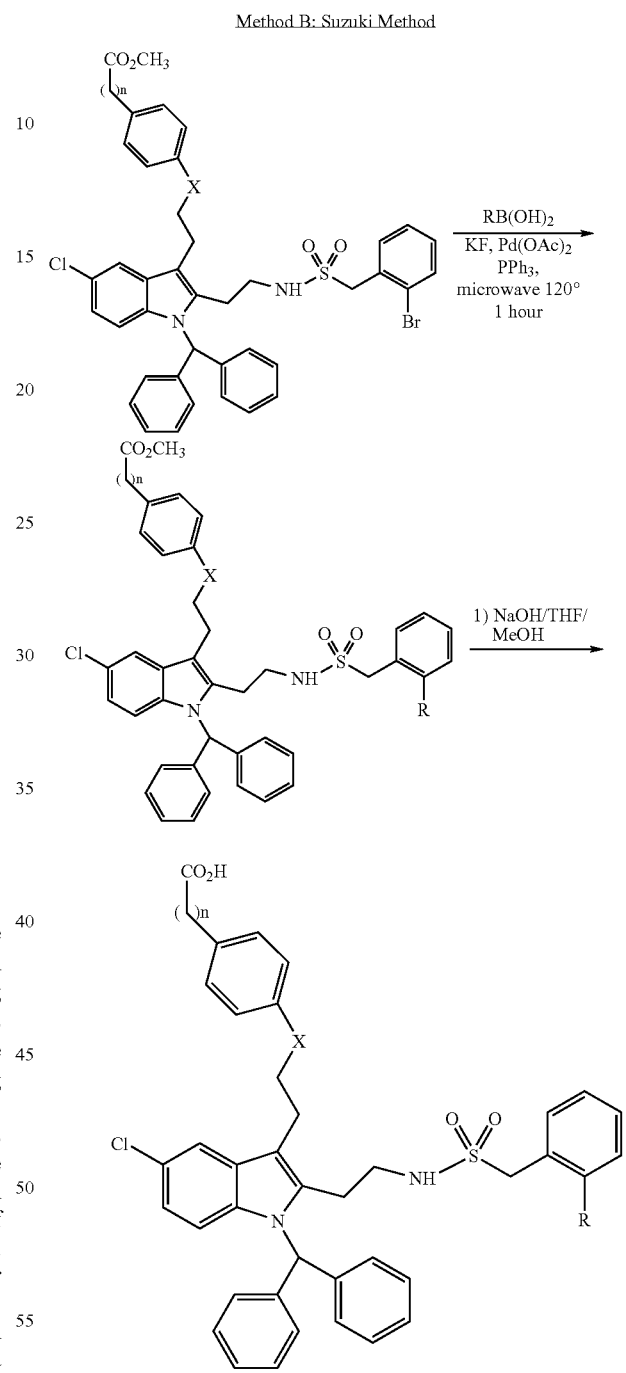

As shown above in Method A, an initial indole may be alkylated at the C3 position (the carbon atom at the 3-position of the indole moiety) with aldehydes or the corresponding acetals in the presence of a Lewis or Bronsted acid, such as boron triflouride etherate or trifluoroacetic acid. The indole nitrogen may then be alkylated by treatment with a strong base such as sodium bis(trimethylsilyl)amide, n-BuLi, sodium hydride or potassium hydride in a solvent such as DMF, DMSO or THF followed by exposure to the appropriate alkyl halide. The resulting product can be treated with carbon tetrabromide in carbon tetrachloride and a catalytic amount of benzoyl peroxide to effect dibromination of the C2 methyl group. The dibromide can then either be stirred with silver carbonate in acetone water or poured into DMSO and stirred. Both of these procedures generate the aldehyde which is then subjected to the nitro aldol reaction with nitromethane and ammonium acetate at reflux. The resulting vinyl nitro intermediate is reduced to the amine upon treatment with zinc mercury amalgam in a mixture of THF and conc. HCl at reflux. This amine can then be treated with the requisite sulfonyl chloride under biphasic conditions, aqueous sodium bicarbonate/dichloromethane, or in organic solvent with the addition of a hindered organic amine base. The final hydrolysis can be accomplished under basic conditions with sodium hydroxide in water and methanol and THF at room temperature or at elevated temperature. Alternatively it may be cleaved by treatment with sodium thiomethoxide in a solvent such as THF or DMF at elevated temperatures (50° C.-100° C.).

As shown above in Method B, a halide is placed in a vessel with a boronic acid, a base (for example KF), a palladium source (for example $Pd(OAc)_2$) a ligand (for example $PPh_3$), and a suitable degassed solvent, for example DMF, MeOH, water or a combination thereof. The mixture is then heated either thermally or in a microwave reactor. Standard workup yields the protected (ester) product, which is then hydrolyzed in base to afford the free acid product.

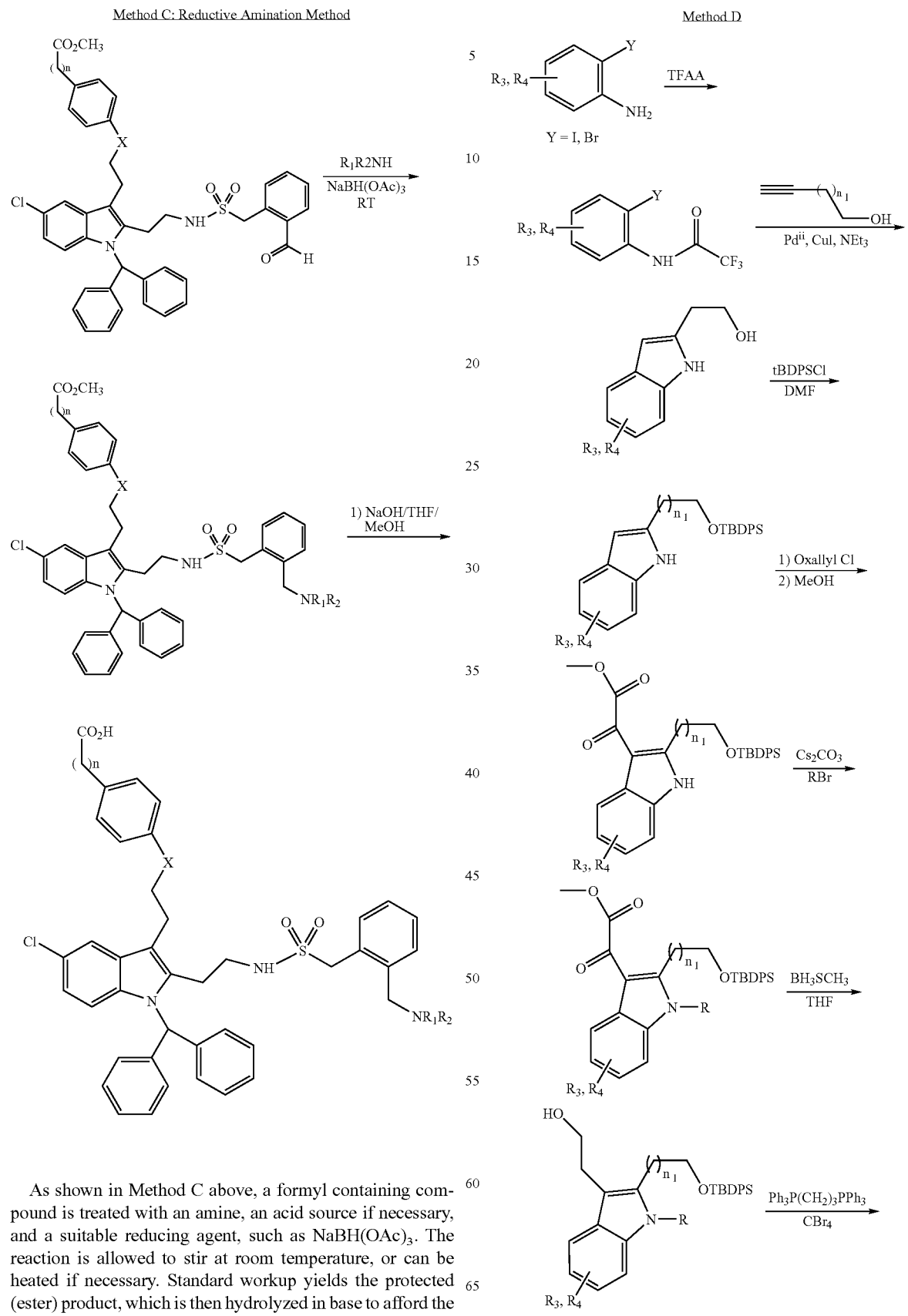
As shown in Method C above, a formyl containing compound is treated with an amine, an acid source if necessary, and a suitable reducing agent, such as NaBH(OAc)$_3$. The reaction is allowed to stir at room temperature, or can be heated if necessary. Standard workup yields the protected (ester) product, which is then hydrolyzed in base to afford the free acid product -continued

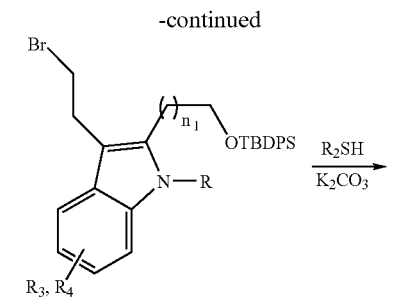

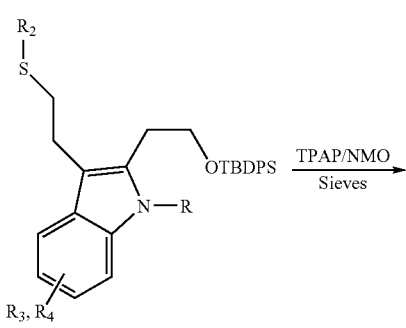

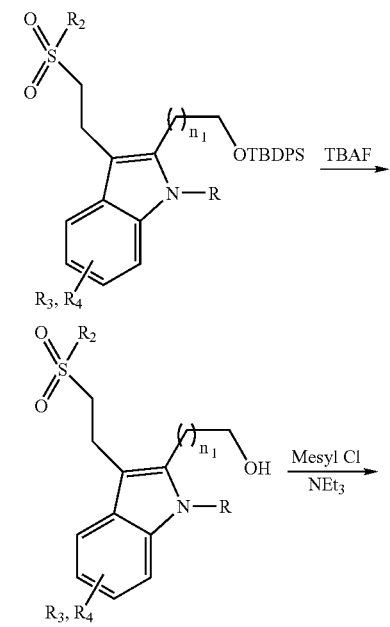

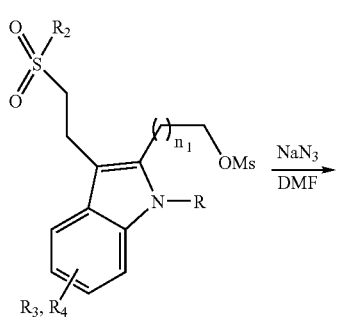

-continued

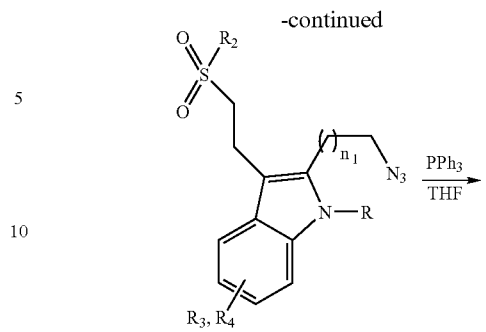

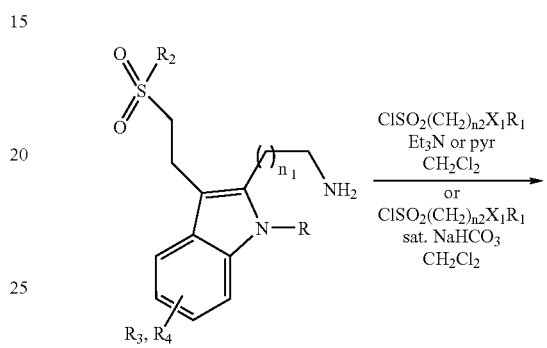

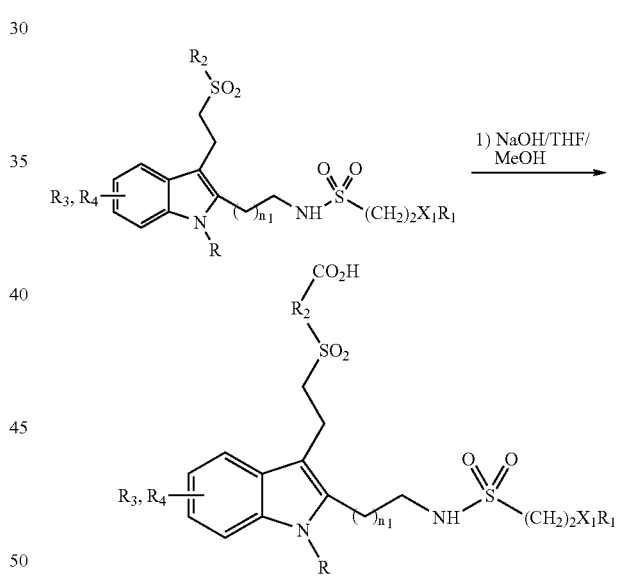

As shown in Method D above, an appropriately substituted halo amine is reacted with trifluoroacetic anhydride to yield an intermediate that could be treated with a Pd(II) catalyst in the presence of a base such as triethylamine, CuI and a suitable alkyne, under heat to yield the desired indole intermediate. The primary alcohol is protected as a silyl ether using a silyl chloride such as t-butyldiphenyl silyl chloride and a base such as imidazole. The protected indole is then treated with oxalyl chloride followed by methanol which produces the desired oxalate ester, the indole nitrogen of which can be alkylated using a suitable base such as cesium carbonate in refluxing acetonitrile and a halide. The oxalate can then be reduced via the action of a suitable reducing agent such as borane. The resulting primary alcohol is converted to a halide using, for example, CBr₄ and a phosphine, which can then be displaced with a nucleophile such as a thiophenol. The resulting thioether can be oxidized by a variety of oxidizing agents including oxone and TPAP/NMO. The resulting sulfone can be deprotected via the action of a flouride source such as TBAF, CsF or HF. The resulting alcohol can be converted to a halide or mesylate, for example using methane sulfonyl chloride and an organic base, which can then be displaced by sodium azide in DMF. The resulting alkyl azide can be reduced under the action of triphenyl phosphine and wet THF. The amine can be sulfonylated by the action of a sulfonyl chloride under either biphasic Schotten-Baumann conditions (aq. bicarbonate and dichloromethane) or under anhydrous conditions consisting of dichloromethane and an organic base such as Hunigs base. The resulting ester intermediate is hydrolyzed using a base, such as NaOH, KOH or LiOH, and a mixture of solvents including an alcoholic solvent, water and tetrahydrofuran.

Method E:

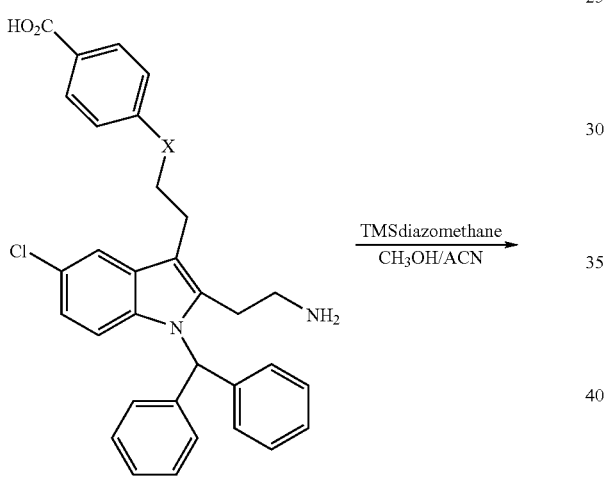

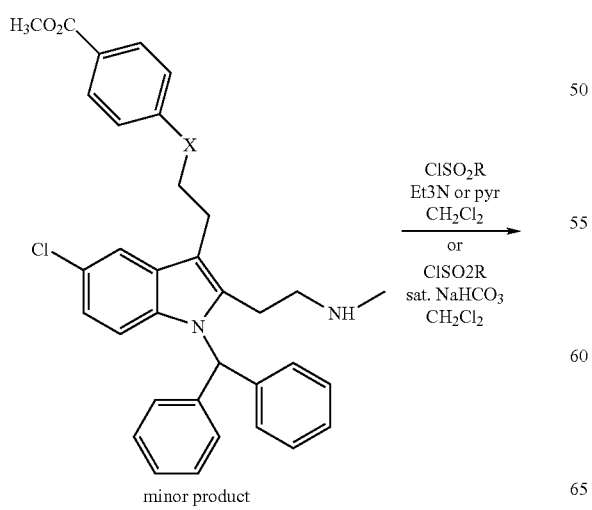

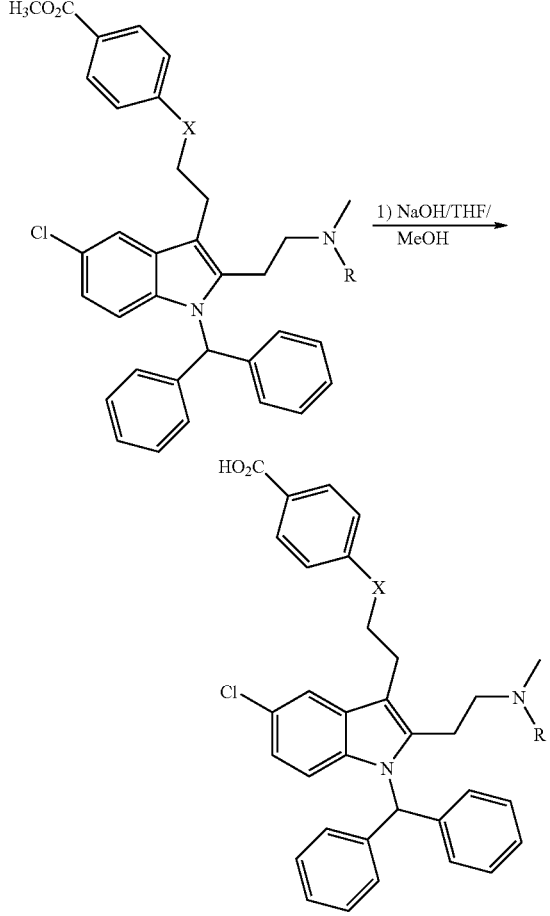

As shown in Method E above, a starting amino acid is esterified and N-alkylated in one pot (using for example a diazo reagent or trimethylsilyldiazo reagent). This N-alkyl ester is then sulfonylated with a sulfonyl chloride using either Schotten-Baumann conditions or organic solvents and organic bases. Finally, the N-alkyl ester is hydrolyzed to the desired product using a base, such as NaOH, and a suitable solvent system, such as THF and an alcohol.

The following compounds were prepared in accordance with Methods A-E above.

Example 1

4-{2-[2-[2-({[2-(benzyloxy)benzyl]sulfonyl}amino) ethyl]-5-chloro-1-(diphenylmethyl)-1H-indol-3-yl] ethoxy}benzoic acid Step 1: To 4-hydroxy-benzoic acid methyl ester (1.0 eq) in DMF (0.83 M) was added K₂CO₃ (2.0 eq) followed by 2-bromo-1,1-diethoxy-ethane and the reaction mixture was stirred at 110° C. for 2 days. TLC showed a new spot. The reaction mixture was diluted with ethyl acetate, washed with 1N NaOH, water, and brine, dried over sodium sulfate, and solvent was removed to afford desired product in 84% yield. This material was used in the next step without further purification.

Step 2: To the above product (1.0 eq) and 5-chloro-2-methyl indole (1.0 eq) in CH₂Cl₂ (0.12 M) was added triethylsilane (3.0 eq) followed by trifluoroacetic acid (3.0 eq).

After being stirred overnight at room temperature, water and trifluroacetic acid (1.0 eq) were added to the reaction mixture, which was stirred at room temperature for two days, diluted with CH$_2$Cl$_2$, washed with 1N NaOH, water, and brine, and dried over sodium sulfate. Trituration of the material with CH$_2$Cl$_2$ and hexanes afforded the C3 alkylated indole in 92% yield Step 3: To the indole from above (1.0 eq) in DMF (0.36 M) at 25° C. was added NaH (1.2 eq, 60% dispersion in oil). The brown solution was stirred at 0 to –5° C. for 1 h, and then bromodiphenylmethane was added (1.1 eq). The reaction mixture was stirred overnight, and then quenched with water, diluted with ethyl acetate, washed with water and brine, dried over sodium sulfate and purified by column chromatography to yield 72% of the desired product.

Step 4: To the N-alkylated indole from above (1.0 eq) in CCl$_4$ (0.2 M) was added N-bromosuccinimide (2.0 eq) and a catalytic amount of benzoyl peroxide. The solution was heated to reflux for 3 h, cooled to 25° C., filtered, and the solid was washed with CCl$_4$. The filtrate was concentrated to a foam which was dried in vacuo. The foam was dissolved in acetone, and Ag$_2$CO$_3$ (1.1 eq.) was added followed by water, and the reaction mixture was stirred overnight at room temperature, and then filtered and washed with acetone. The filtrate was concentrated to a residue, to which was added water. This mixture was extracted with ethyl acetate, washed with brine, and dried over sodium sulfate. Chromatographic purification of the residue gave the desired product in 85% yield.

Step 5: To the above aldehyde (1.0 equiv) in CH$_3$NO$_2$ (0.2 M) was added ammonium acetate (4 equiv) and the resulting mixture was heated to reflux for 4 h. The reaction mixture was then diluted with EtOAc and washed with brine. The aqueous phase was extracted with EtOAc. The combined organic extracts were washed with brine, dried over sodium sulfate, and concentrated until an orange crystalline solid precipitated. The mixture was refrigerated overnight and the nitroolefin (76% yield) was collected by filtration. Evaporation of the solution phase and purification of the residue by column chromatography (gradient elution 100% toluene→1% EtOAc-toluene) afforded an additional amount of the nitroolefin (23% yield).

Step 6: Zinc dust (20 equiv) was suspended in 5% aqueous HCl solution (8 M Zn/5% HCl). To this mixture was added HgCl$_2$ (0.28 equiv). The mixture was shaken for 10 min, the aqueous phase was decanted and replaced with fresh 5% HCl, and again the mixture was shaken for 5 min and the aqueous phase was removed. The zinc-mercury amalgam thus generated was then added to a mixture of the nitroolefin (1.0 equiv) and conc. HCl (80 equiv) in THF (0.04 M nitroolefin/THF). The mixture was maintained at a gentle reflux for 1 h. The formation of product was followed by TLC analysis. The mixture was cooled to room temperature and the solids were removed by filtration through Celite. Conc. NH$_4$OH was added to the solution phase and the mixture was concentrated on the rotary evaporator. The residue was dissolved in CH$_2$Cl$_2$ and conc. NH$_4$OH. The aqueous phase was extracted with CH$_2$Cl$_2$, and the organic phase was washed with brine, dried over sodium sulfate, and concentrated. Purification by column chromatography afforded the desired product (65% yield).

Step 7: Sodium sulfite (4.2 g) was added to a stirred mixture of 1-benzyloxy-2-bromomethyl-benzene (8.9 g), tetrabutylammonium iodide (59 mg) and water (150 ml). The mixture was warmed to reflux for overnight. As the mixture cooled to 0° C., it was acidified by 6N HCl. Extraction by ethyl acetate (100 ml×6) was performed (some remained in the aqueous layer). The combined organic phases were dried over MgSO$_4$. The filtrate was concentrated on vacuo. The product was triturated by ethyl ether to give (2-Benzyloxy-phenyl)-methanesulfonic acid (678 mg, 8%). $^1$H NMR (400 MHz, DMSO-D6): δ 3.82 (s, 2 H) 5.09 (s, 2 H) 6.86 (t, J=7.45 Hz, 1 H) 6.96 (d, J=8.08 Hz, 1 H) 7.14 (t, J=7.83 Hz, 1 H) 7.32 (d, J=7.33 Hz, 1 H) 7.38 (t, J=7.33 Hz, 2 H) 7.46 (d, J=9.09 Hz, 1 H) 7.52 (d, J=7.07 Hz, 2 H).

Step 8: Tetrahydrofuran (10 ml), (2-Benzyloxy-phenyl)-methanesulfonic acid (138 mg), and N,N-dimethylformamide (2 drops) was cooled to –78° C. and oxalyl chloride (315 mg) was added slowly. The reaction mixture was stirred for 3 h from –78° C. to 0° C. The reaction mixture was clarified by filtration. The filtrate was washed with iced-water and heptane, and dried to give (2-benzyloxy-phenyl)-methanesulfonyl chloride (114 mg, 77%). $^1$H NMR (400 MHz, CDCl$_3$): δ 5.06 (s, 2 H) 5.15 (s, 2 H) 7.04 (m, 2 H) 7.42 (m, 7 H).

Step 9: To methyl 4-{2-[2-(2-aminoethyl)-1-benzhydryl-5-chloro-1H-indol-3-yl]ethoxy}benzoate (1.0 equiv, Step 6) and sat. NaHCO$_3$ (0.14 M) in CH$_2$Cl$_2$ (0.07 M) was added (2-benzyloxy-phenyl)-methanesulfonyl chloride (1.0 equiv, step 8). After 16 h the mixture was poured into saturated sodium bicarbonate and extracted with CH$_2$Cl$_2$. The combined organic phase was washed with brine, dried over sodium sulfate and purified by column chromatography to afford 77% of the desired product.

Step 10. The resulting ester was hydrolyzed by stirring with 1N NaOH (5 equiv) in THF (0.07 M) and enough MeOH to produce a clear solution. The reaction was monitored by TLC (10% MeOH—CH$_2$Cl$_2$) for the disappearance of starting material. When the reaction was complete, the mixture was concentrated, diluted with H$_2$O, and acidified to pH 2-4 using 1 M HCl. The aqueous phase was extracted with EtOAc and the organic phase was washed with brine, dried over sodium sulfate, and concentrated to afford the title acid in 97% yield. $^1$H NMR (400 MHz, CDCl$_3$) δ 2.86 (d, J=14.40 Hz, 2 H) 2.92-3.04 (m, 2 H) 3.13 (t, J=6.69 Hz, 2 H) 4.12-4.23 (m, 2 H) 4.28 (s, 2 H) 4.34-4.45 (m, 1 H) 4.90 (s, 2 H) 6.47 (d, J=8.84 Hz, 1 H) 6.73-6.93 (m, 6 H) 6.95-7.08 (m, 4 H) 7.16-7.36 (m, 13 H) 7.53 (d, J=1.77 Hz, 1 H) 7.92-8.04 (m, 2 H); HRMS calc for [C$_{46}$H$_{41}$ClN$_2$O$_6$.S+H$^-$] 783.2301. found 783.2292; purity H$_2$O/MeOH 97%, H$_2$O/MeCN 95%.

Example 2

4-{2-[5-chloro-1-(diphenylmethyl)-2-(2-{[(2-hydroxybenzyl)sulfonyl]amino}ethyl)-1H-indol-3-yl]ethoxy}benzoic acid Step 1: To 4-{2-[2-[2-({[2-(benzyloxy)benzyl]sulfonyl}amino)ethyl]-5-chloro-1-(diphenylmethyl)-1H-indol-3-yl]ethoxy}benzoic acid (Step 9, Example 1, 109 mg, 0.14 mmol) was added THF and MeOH. 10% of Pd/C (11 mg) was added. The mixture was stirred at room temperature under H$_2$ (1 atm) overnight and filtered through celite, concentrated, and column chromatographed (35% EtOAc/hex) to give 4-(2-{1-benzhydryl-5-chloro-2-[2-(2-hydroxy-phenyl-methanesulfonylamino)-ethyl]-1H-indol-3-yl}-ethoxy)-benzoic acid methyl ester (74 mg, 76%), an off-white solid.

Step 2: The ester intermediate was hydrolyzed according to Step 10 Example 1 to afford the title acid in 85% yield. $^1$H NMR (400 MHz, CDCl$_3$) δ 2.87-3.01 (m, 2 H) 3.00-3.11 (m, 2 H) 3.18 (t, J=6.57 Hz, 2 H) 4.17 (s, 2 H) 4.19-4.30 (m, 2 H) 4.52 (t, J=5.81 Hz, 2 H) 6.52 (d, J=8.84 Hz, 1 H) 6.75-6.90 (m, 6 H) 6.99 (dd, J=7.45, 1.64 Hz, 1 H) 7.01-7.13 (m, 4 H)

7.13-7.22 (m, 1 H) 7.27-7.37 (m, 6 H) 7.53 (d, J=2.02 Hz, 1 H) 7.91-8.04 (m, 2 H); HRMS calc for [$C_{39}H_{35}ClN_2O_6.S+H^-$] 695.1977 found 695.1984.

Example 3

4-{2-[5-chloro-2-(2-{[(2,6-dibromobenzyl)sulfonyl]amino}ethyl)-1-(diphenylmethyl)-1H-indol-3-yl]ethoxy}benzoic acid Step 1. To a solution of 2,6-dibromotoluene (5.38 g, 21.53 mmol) in benzene (1.54 M) was added N-bromosuccinimide (4.21 g, 23.68 mmol) and benzoyl peroxide (0.52 g, 2.15 mmol). The mixture was then heated to reflux overnight. The mixture was cooled to rt, diluted with $H_2O$ and extracted with EtOAc. The combined organic phase was washed with brine, dried over $MgSO_4$ and concentrated to afford 7.65 g of the benzyl bromide, a brown solid. 1H NMR (400 MHz, $CDCl_3$) δ4.83 (s, 2 H), 7.01 (t, J=8.0 Hz, 1 H), 7.55 (d, J=8.1 Hz, 2 H).

Step 2. To a solution of the 2,6-dibromobenzyl bromide (1.0 equiv, Step 1) in DMF (1.30 M) was added potassium thioacetate (1.2 equiv.) and the mixture was allowed to stir at rt for 3-4 h. The reaction was monitored by LC/MS for disappearance of starting material. The mixture was diluted with $H_2O$ and extracted with EtOAc. The combined organic phase was washed with brine, dried over $MgSO_4$ and concentrated to afford 6.70 g (89%) of the benzyl thioacetate as a brown oil.

Step 3. To a solution of the thioacetate (1.0 equiv, 6.70 g, 20.7 mmol) in AcOH (0.19M) and $H_2O$ (0.91M) was added sodium acetate (6.7 equiv.). Chlorine was then bubbled through the reaction mixture vigorously for a period of 30-45 min. The mixture was then concentrated, diluted with ether, washed with $H_2O$ and brine, dried with $MgSO_4$ and concentrated to afford 5.30 g (74%) of the desired 2,6-dibromophenyl-methanesulfonyl chloride, a brown solid. $^1$H NMR (400 MHz, $CDCl_3$) δ 5.55 (s, 2 H), 7.17 (t, J=8.0 Hz, 1 H), 7.67 (d, J=8.1 Hz, 2 H)

Step 4. 4-{2-[2-(2-Amino-ethyl)-1-benzhydryl-5-chloro-1H-indol-3-yl]-ethoxy}-benzoic acid methyl ester (Example 1, Step 6, 126 mg, 0.23 mmol) was reacted with 2,6-dibromophenyl-methanesulfonyl chloride (Step 3) according to the procedure in Example 1, Step 9 to afford 203 mg of the desired sulfonamide as a white solid in quantitative yield.

Step 5. Using the procedure in Example 1, Step 10, the sulfonamide ester (175 mg, 0.206 mmol) was hydrolyzed to afford the 146 mg (85%) of the title product, a white solid. 1H NMR (400 MHz, $CDCl_3$) δ 2.87-3.03 (m, 2 H), 3.06-3.14 (m, 2 H), 3.22 (t, J=6.9 Hz, 2 H), 4.23 (t, J=6.4 Hz, 2 H), 4.53 (t, J=5.9 Hz, 1 H), 4.72 (s, 2 H), 6.51 (d, J=8.8 Hz, 1 H), 6.82 (dd, J=9.0, 2.1 Hz, 1 H), 6.87 (d, J=8.8 Hz, 2 H), 6.92 (s, 1 H), 6.97 (t, J=8.0 Hz, 1 H), 7.05-7.12 (m, J=6.2, 2.9 Hz, 4 H), 7.29-7.34 (m, 6 H), 7.49 (d, J=8.1 Hz, 2 H), 7.54 (d, J=2.0 Hz, 1 H), 8.00 (d, J=8.8 Hz, 2 H).

Example 4

4-(2-{1-benzhydryl-5-chloro-2-[2-methyl-6-nitrophenylmethanesulfonylamino)-ethyl-1-H-indol-3-yl}-ethoxy)-benzoic acid Step 1. To a solution of 2-methyl-6-nitrophenylbenzoic acid (3.02 g, 16.67 mmol) in thionyl chloride (0.56 M) was added DMF (cat.) and the mixture was heated to reflux for 5.5 h. The mixture was then cooled to room temperature and concentrated. The residue was then taken up in THF (30 mL) and added slowly over 20 min to a slurry of $NaBH_4$ in THF (30 mL) which pre-cooled to 0° C. The mixture was stirred at rt for 2 h and then quenched by addition of $H_2O$ followed by 4M HCl. The mixture was extracted with EtOAc. The combined organic phase was washed with sat. $NaHCO_3$ and brine, dried over $MgSO_4$ and concentrated to afford 2.52 g (90%) of the benzyl alcohol, an orange solid. $^1$H NMR (400 MHz, $CDCl_3$) δ 2.55 (s, 3 H), 4.70 (s, 2 H), 7.35 (t, J=7.8 Hz, 1 H), 7.48 (d, J=7.6 Hz, 1 H), 7.70 (d, J=8.3 Hz, 1 H).

Step 2. To a solution of the benzyl alcohol (2.52 g, 15.07 mmol) in $CH_2Cl_2$ (0.12M) cooled to −78° C. and under argon was slowly added $BBr_3$, 1.0M in $CH_2Cl_2$, (23 mL, 22.6 mmol). The mixture was stirred at room temperature overnight and then diluted with $H_2O$ (150 mL). The layers were separated and the organic phase was washed with brine, dried over $MgSO_4$ and concentrated to afford 2.97 g (86%) of 2-methyl-6-nitrobenzyl bromide, a brown solid. 1H NMR (400 MHz, $CDCl_3$) δ 2.53 (s, 3 H), 4.72 (s, 2 H), 7.36 (t, J=7.8 Hz, 1 H), 7.46 (d, J=7.6 Hz, 1 H), 7.75 (d, J=8.1 Hz, 1 H).

Step 3. 2-Methyl-6-nitrobenzyl bromide (Step 2, 1.5 g, 6.5 mmol) was reacted with potassium thioacetate according to the procedure in Example 3, Step 2, to afford 1.44 g of the benzyl thioacetate, a brown oil.

Step 4. Following the procedure in Example 3, Step 3, the benzyl thioacetate (1.44 g, 6.39 mmol) was oxidized to afford 1.35 g (84%) of (2-methyl-6-nitrophenyl)methanesulfonyl chloride, a orange solid. $^1$H NMR (400 MHz, $CDCl_3$) δ 2.62-2.65 (m, 3 H), 5.68 (s, 2 H) Broad, 7.54 (t, J=7.8 Hz, 1 H), 7.58-7.60 (m, 1 H), 7.91 (d, J=7.8 Hz, 1 H).

Step 5. Using the procedure in Example 1, Step 9, 4-{2-[2-(2-amino-ethyl)-1-benzhydryl-5-chloro-1H-indol-3-yl]-ethoxy}-benzoic acid methyl ester (Example 1, Step 6, 255 mg, 0.47 mmol) was reacted with the sulfonyl chloride from Step 4 to afford 318 mg of the sulfonamide, a yellow solid in 90% yield.

Step 6. The sulfonamide ester (101 mg, 0.13 mmol) was hydrolyzed according to Example 1, Step 10 to afford the 87 mg (91%) of the title product, a white solid. 1H NMR (400 MHz, $CDCl_3$) δ 2.48 (s, 3 H), 2.87-2.99 (m, 2 H), 3.03-3.10 (m, 2 H), 3.22 (t, J=6.6 Hz, 2 H), 4.23 (t, J=6.6 Hz, 2 H), 4.33 (t, J=5.9 Hz, 1 H), 4.77 (s, 2 H), 6.51 (d, J=8.8 Hz, 1 H), 6.82 (dd, J=8.8, 2.0 Hz, 1 H), 6.88 (d, J=8.8 Hz, 2 H), 6.91 (s, 1 H), 7.04-7.12 (m, 4 H), 7.29-7.35 (m, 7 H), 7.42 (d, J=7.3 Hz, 1 H), 7.54 (d, J=2.0 Hz, 1 H), 7.66 (d, J=7.6 Hz, 1 H), 7.99 (d, J=8.8 Hz, 2 H);

Example 5

4-(2-{5-chloro-1-(diphenylmethyl)-2-[2-({[2-(trifluoromethyl)benzyl]sulfonyl}amino)ethyl]-1H-indol-3-yl}ethoxy)benzoic acid Step 1: A mixture of 2-(trifluoromethyl)benzyl bromide (25 g, 0.14 mol) sodium sulfite (19.1 g, 0.15 mol), tetrabutylammonium iodide (0.224 g, 0.6 mmol) and $H_2O$ (930 mL) was heated to reflux for 2 d. The mixture was cooled to room temperature and the aqueous phase was decanted from the oily residue and concentrated on the rotovap to dryness to afford the desired sodium salt (22.2 g, 60%), as a white solid, which was used without further purification.

Step 2: (2-Trifluoromethylphenyl)methanesulfonic acid sodium salt (22.2 g, 84 mmol) was suspended in MeOH (950 mL) and cooled to −20° C. At that temp with continued cooling HCl (g) was bubbled through the mixture for 5 min. The resulting white suspension was stirred at room temperature for 1.5 h, then cooled in an ice-bath. The resulting suspension was filtered and the collected solid allowed to air-dry overnight to afford (2-trifluoromethylphenyl)methanesulfonic acid (20.3 g, ~100%), a white solid, which was used without further purification Step 3: To a suspension of (2-trifluoromethylphenyl)methanesulfonic acid (20.3 g, 84 mmol) in THF (1.9 L) and DMF (5.0 mL) at −20° C. was added oxalyl chloride (44.7 mL, 0.5 mol) slowly dropwise over 1 hr. The bath temperature was maintained below 0° C. for 4 h, at which point the reaction was evaporated to a volume of ~250 mL and diluted with 500 mL of ethyl acetate. This solution was washed with brine in a separatory funnel and dried over magnesium sulfate. The solution was then evaporated to a brown oil. This oil was taken up in 500 mL of pet ether (30-50°) and heated with a heat gun until the oil went into solution. The solution was then placed into a dry-ice acetone bath to cool resulting in formation of a white crystalline material. This material was collected via filtration and dried to afford 19 g (85%) of (2-trifluoromethylphenyl)methanesulfonyl chloride as a white solid.

Step 4: As outlined in Step 9, Example 1, methyl 4-{2-[2-(2-aminoethyl)-1-benzhydryl-5-chloro-1H-indol-3-yl]ethoxy}benzoate (Step 9, Example 1, 0.15 g, 0.28 mmol) was reacted with 2-(trifluoromethylphenyl)methanesulfonyl chloride (0.145 g, 0.50 mmol) to afford 0.220 g of the sulfonamide, a white foam, in 75% yield. $^1$H NMR (400 MHz, CDCl$_3$) δ 2.73-2.88 (m, 2 H), 2.96-3.09 (m, 2 H), 3.16 (t, J=6.6 Hz, 2 H), 3.88 (s, 3 H), 4.19 (t, J=6.6 Hz, 2 H), 4.23 (t, J=6.4 Hz, 1 H), 4.34 (s, 2 H), 6.51 (d, J=8.8 Hz, 1 H), 6.77-6.84 (m, 3 H), 6.86 (s, 1 H), 6.98-7.12 (m, 4 H), 7.27-7.35 (m, 6 H), 7.36-7.47 (m, 2 H), 7.53 (d, J=1.5 Hz, 1 H), 7.59-7.69 (m, 2 H), 7.95 (d, J=8.8 Hz, 2 H).

Step 5: Using the procedure in Step 10 Example 1, the sulfonamide ester (137 mg, 0.18 mmol) was hydrolyzed to afford 86 mg (64%) of the title product, a white powder. $^1$H NMR (400 MHz, DMSO-d$_6$) δ 3.04 (s, 4 H), 3.18 (t, J=6.6 Hz, 2 H), 4.23 (t, J=5.9 Hz, 2 H), 4.42 (s, 2 H), 6.48 (d, J=8.8 Hz, 1 H), 6.81 (dd, J=9.0, 2.1 Hz, 1 H), 6.98 (d, J=9.1 Hz, 2 H), 7.03-7.18 (m, 5 H), 7.29-7.42 (m, 6 H), 7.48-7.62 (m, 3 H), 7.66 (d, J=2.0 Hz, 2 H), 7.72 (d, J=7.8 Hz, 1 H), 7.85 (d, J=8.8 Hz, 2 H), 12.49 (s, 1 H); HRMS: calcd for C$_{40}$H$_{34}$ClF$_3$N$_2$O$_5$S+H+, 747.19018. found (ESI-FTMS, [M+H]$^{1+}$), 747.1886; HPLC purity H$_2$O/CH$_3$CN: 96.2%, H$_2$O/MeOH: 95.4%.

Example 6

4-(2-{5-chloro-1-(diphenylmethyl)-2-[2-({[2-fluoro-6-(trifluoromethyl)benzyl]sulfonyl}amino)ethyl]-1H-indol-3-yl}ethoxy)benzoic acid Step 1: Using the procedure described in Example 5, Step 1,2-fluoro-6-(trifluoromethylphenyl)benzyl bromide (15 g, 61 mmol) afforded 2-fluoro-6-(trifluoromethylphenyl)methanesulfonic acid sodium salt (15 g, 89%), a white solid. $^1$HNMR (400 MHz, DMSO-d$_6$) δ 4.02 (s, 2 H), 7.26-7.66 (m, 3 H).

Step 2: Using the procedure described in Example 5, Step 2,2-fluoro-6-(trifluoromethylphenyl)methanesulfonic sodium salt (15 g, 53 mmol) afforded 2-fluoro-6-(trifluoromethylphenyl)methanesulfonic acid (15 g), a pale orange oil which was used without further purification. $^1$H NMR (400 MHz, DMSO-d$_6$) δ 4.12 (s, 2 H), 7.39-7.73 (m, 3 H).

Step 3: Using the procedure described in Example 5, Step 3,2-fluoro-6-(trifluoromethylphenyl)methanesulfonic acid (15 g, 53 mmol) afforded 11 g of crude product which was purified by low-temperature crystallization from hexanes to afford 2-fluoro-6-(trifluoromethylphenyl)methanesulfonyl chloride (9.0 g, 62%). $^1$H NMR (400 MHz, CDCl$_3$) δ 5.31 (s, 2 H), 7.38-7.51 (m, 1 H), 7.58-7.68 (m, 2 H).

Step 4: As outlined in Step 9, Example 1, methyl 4-{2-[2-(2-aminoethyl)-1-benzhydryl-5-chloro-1H-indol-3-yl]ethoxy}benzoate (Step 6, Example 1, 0.12 g, 0.22 mmol) was reacted with 2-fluoro-6-(trifluoromethylphenyl)methanesulfonyl chloride (0.074 g, 0.27 mmol) to afford 0.164 g of the sulfonamide, a white foam, in 95% yield. $^1$H NMR (400 MHz, CDCl$_3$). δ 2.83-3.03 (m, 2 H), 3.07-3.17 (m, 2 H), 3.21 (t, J=6.6 Hz, 2 H), 3.88 (s, 3 H), 4.22 (t, J=6.6 Hz, 2 H), 4.31 (t, J=6.3 Hz, 1 H), 4.43 (s, 2 H), 6.52 (d, J=9.1 Hz, 1 H), 6.76-6.89 (m, 3 H), 6.92 (s, 1 H), 7.07 (dd, J=6.1, 4.3 Hz, 4 H), 7.23 (t, J=8.6 Hz, 2 H), 7.28-7.34 (m, 5 H), 7.38-7.52 (m, 2 H), 7.54 (d, J=1.8 Hz, 1 H), 7.95 (d, J=9.1 Hz, 2 H).

Step 5: Using the procedure in Step 10 Example 1, the sulfonamide ester (136 mg, 0.17 mmol) was hydrolyzed to afford 130 mg (97%) of the title product, a white powder. $^1$H NMR (400 MHz, DMSO-d$_6$) δ 3.00-3.15 (m, 4 H), 3.17 (t, J=6.4 Hz, 2 H), 4.22 (t, J=6.6 Hz, 2 H), 4.45 (s, 2 H), 6.46 (d, J=8.8 Hz, 1 H), 6.79 (dd, J=8.8, 2.3 Hz, 1 H), 6.97 (d, J=9.1 Hz, 2 H), 7.03-7.13 (m, 5 H), 7.16-7.41 (m, 6 H), 7.48-7.70 (m, 4 H), 7.74-7.90 (m, 3 H), 12.56 (s, 1 H); HRMS: calcd for C$_{40}$H$_{33}$ClF$_4$N$_2$O$_5$S+H+, 765.18076. found (ESI-FTMS, [M+H]$^{1+}$), 765.1814; HPLC purity H$_2$O/CH$_3$CN: 96.6%, H$_2$O/MeOH: 97.9%.

Example 7

4-{3-[5-chloro-2-(2-{[(2,6-dibromobenzyl)sulfonyl]amino}ethyl)-1-(diphenylmethyl)-1H-indol-3-yl]propyl}benzoic acid Step 1: A mixture of methyl-4-iodobenzoate (5.3 g, 20.2 mmol), allyl alcohol (1.78 g, 30.3 mmol), NaHCO$_3$ (4.24 g, 50.5 mmol), Pd(OAc)$_2$ (0.14 g, 0.60 mmol), (n-Bu)$_4$NBr (6.55 g, 20.2 mmol) and 4-Å molecular Sieves (4.1 g) in anhydrous DMF (69 mL) was stirred at room temperature for 4 days. The reaction mixture was filtered through celite and the filtrate poured onto water and extracted with EtOAc. The organic layer was washed with brine, dried (Na$_2$SO$_4$), and concentrated under vacuum. Flash chromatography (silica gel, 10-20% EtOAc-hexanes) gave 2.11 g (85% based on the recovered starting material) of the desired 4-(3-oxo-propyl)-benzoic acid methyl ester as a clear oil.

Step 2: To a solution of 5-chloro-2-methylindole (0.86 g, 5.2 mmol) and 4-(3-oxo-propyl)-benzoic acid methyl ester (1.0 g, 5.2 mmol) in methylene chloride (50 mL), was added TFA (1.78 g, 15.6 mmol), followed by triethylsilane (1.81 g, 15.6 mmol). The reaction mixture was stirred overnight, quenched with sat. NaHCO$_3$ solution (50 mL), and the organic layer was washed with sat. NaHCO$_3$ solution, water, brine, and dried (Na$_2$SO$_4$). The solvent was removed under reduced pressure, and the residue was purified by flash column chromatography with 10-20% EtOAc/hexanes to yield the desired product (1.67 g) in 94% yield.

Step 3: To a solution of the product from step 2 (1.66 g, 4.86 mmol) in DMF (20 mL) was added NaH (60% in mineral oil, 0.24 g, 5.83 mmol) under N$_2$ atmosphere. The mixture was stirred for 1 h at room temperature, followed by the dropwise addition of benzhydryl bromide (1.8 g, 7.29 mmol) in DMF (5 mL). This reaction mixture was stirred overnight at room temperature. Water (500 mL) was added, and the mixture was extracted with EtOAc, washed with brine, dried (Na$_2$SO$_4$), and concentrated under reduced pressure to a brown syrup, which was purified by silica-gel chromatography using 10% EtOAc/hexanes as eluent to isolate the N-benzhydrylindole as a white solid (1.47 g) in 59% yield.

Step 4: The product from above (1.46 g, 2.87 mmol) was dissolved in CCl$_4$ (14.5 mL), followed by the addition of NBS (1.02 g, 5.73 mmol) and benzoyl peroxide (2 mg). The reaction mixture was heated to reflux for 1 h (until all the starting material disappeared by TLC analysis). This mixture was cooled to room temperature, filtered and the solid was washed with CCl$_4$. The filtrate was evaporated to a brown residue, which was dissolved in acetone (40 mL) and water (4 mL). Ag$_2$CO$_3$ (1.75 g, 3.16 mmol) was then added to this solution and after being stirred overnight at room temperature, it was filtered through celite, the solvent was evaporated under reduced pressure, and water was added to the residue. It was extracted with EtOAc, washed with brine, dried (Na$_2$SO$_4$), and evaporated to a syrup, which was purified by 10% EtOAc/hexanes to isolate the 2-formyl indole (1.13 g) in 75% yield.

Step 5: To a solution of the 2 formyl indole from above (0.52 g, 1 mmol) in CH$_3$NO$_2$ (6.2 mL) was added NH$_4$OAc (0.077 g, 1 mmol), the mixture was heated to reflux for 1 h, NH$_4$OAc (0.077 g, 1 mmol) was then added, heating at reflux was continued for an additional 1 h, NH$_4$OAc (0.077 g, 1 mmol) was added again and the heating continued for further 1 h. The reaction mixture was allowed to cool to room temperature and EtOAc (50 mL) was added, followed by water (100 mL). The aqueous layer was extracted with EtOAc, and the combined organic layers were washed with brine, dried (Na$_2$SO$_4$), and evaporated to a yellow foam, which was subjected to chromatographic purification using 10% EtOAc/hexanes as an eluent to yield the nitroolefin as a yellow foam (0.38 g) in 68% yield.

Step 6: Zn(Hg) was prepared by adding HgCl$_2$ (3.4 g, 7.2 mmol) to a mixture of Zn-dust (34.7 g, 530.4 mmol) and 5% HCl (38 mL) in a 100 mL beaker. The mixture was stirred vigorously for 10 min. The aqueous phase was decanted, 38 mL of 5% HCl was added to the Zn(Hg) and the mixture was stirred for 10 min. The aqueous phase was decanted. The Zn(Hg) solid was added to the vinyl nitro compound from Step 5 (15 g, 26.57 mmol) in THF (660 mL) and conc. HCl (64.5 mL). This mixture was stirred at room temperature for 1 h, then heated to reflux for 15 min. The reaction mixture was cooled to room temperature and filtered through celite. Aq. NH$_4$OH solution (200 mL) was added to the filtrate, the resulting mixture was stirred for 15 min and the mixture was concentrated to remove THF. The aqueous layer was extracted with CH$_2$Cl$_2$ and the combined organic layer was washed with brine, dried (Na$_2$SO$_4$) and concentrated to a brown foam, which was purified by column chromatography by eluting the column with CHCl$_3$ in the beginning to remove non-polar impurities then with 2% MeOH/CHCl$_3$ to isolate the desired amine in 46% yield (6.1 g).

Step 7. As outlined in step 9 Example 1, methyl 4-{3-[2-(2-aminoethyl)-1-benzhydryl-5-chloro-1H-indol-3-yl]propyl}benzoate (Step 6, 128 mg, 0.24 mmol) was reacted with 2,6-dibromo-phenyl-methanesulfonyl chloride (Step 3, Example 3) to afford 203 mg of the sulfonamide, a tan solid in 100% yield.

Step 8. Using the procedure in step 10 Example 1, the sulfonamide ester (175 mg, 0.206 mmol) was hydrolyzed to afford the 133 mg (77%) of the title product, a yellow solid. 1H NMR (400 MHz, CDCl$_3$) δ1.91-2.02 (m, 2 H), 2.75 (t, J=8.1 Hz, 4 H), 2.86-2.94 (m, 2 H), 2.94-3.03 (m, 2 H), 4.46-4.54 (m, 1 H), 4.70 (s, 2 H), 6.49 (d, J=9.1 Hz, 1 H), 6.79 (dd, J=9.0, 1.9 Hz, 1 H), 6.87 (s, 1 H), 6.96 (t, J=8.1 Hz, 1 H), 7.04-7.11 (m, J=6.2, 2.4 Hz, 4 H), 7.25-7.34 (m, 8 H), 7.40 (d, J=1.8 Hz, 1 H), 7.48 (d, J=7.8 Hz, 2 H), 8.00 (d, J=7.8 Hz, 2 H).

Example 8

4-{3-[5-chloro-2-(2-{[(2,6-dichlorobenzyl)sulfonyl]amino}ethyl)-1-(diphenylmethyl)-1H-indol-3-yl]propyl}benzoic acid Step 1: Using the conditions in Example 3, Step 1, 2,6-dichlorobenzyl bromide (3.32 g, 13.84 mmol) was reacted with potassium thioacetate to afford 2.92 g (90%) of the benzyl thioacetate.

Step 2: Using the procedure in Example 3, Step 2, the benzyl thioacetate (2.90 g, 12.33 mmol) was oxidized to afford 1.7 g (53%) of the sulfonyl chloride, a white solid. 1H NMR (400 MHz, CDCl$_3$) δ 5.43 (s, 2 H), 7.32-7.39 (m, 1 H), 7.43-7.50 (m, 2 H).

Step 3: As outlined in Step 9, Example 1, methyl 4-{3-[2-(2-aminoethyl)-1-benzhydryl-5-chloro-1H-indol-3-yl]propyl}benzoate (Example 7, Step 6, 149 mg, 0.28 mmol) was reacted with 2,6-dichloro-phenyl-methanesulfonyl chloride to afford 170 mg of the sulfonamide, a yellow solid in 80% yield.

Step 4. Using the procedure in Step 10 Example 1, the sulfonamide ester (145 mg, 0.19 mmol) was hydrolyzed to afford the 140 mg (99%) of the title product, a tan solid. 1H NMR (400 MHz, CDCl$_3$) δ 1.89-2.01 (m, 2 H), 2.71-2.80 (m, 4 H), 2.84-2.92 (m, 2 H), 2.95-3.03 (m, 2 H), 4.31 (t, J=6.2 Hz, 1 H), 4.60 (s, 2 H), 6.49 (d, J=9.1 Hz, 1 H), 6.80 (dd, J=8.8, 2.0 Hz, 1 H), 6.87 (s, 1 H), 7.01-7.10 (m, 4 H), 7.12-7.19 (m, 1 H), 7.25-7.34 (m, 10 H), 7.41 (d, J=2.0 Hz, 1 H), 8.00 (d, J=8.1 Hz, 2 H);

Example 9

4-(3-{1-benzhydryl-5-chloro-2-[2-(2-methyl-6-nitro-phenylmethanesulfonylamino)-ethyl-1H-indol-3-yl}-propyl)-benzoic acid Step 1: As outlined in Step 9, Example 1, methyl 4-{3-[2-(2-aminoethyl)-1-benzhydryl-5-chloro-1H-indol-3-yl]propyl}benzoate (Example 7, Step 6, 255 mg, 0.47 mmol) was reacted with 2-methyl-6-nitro-phenyl-methanesulfonyl chloride (Example 4, Step 4) to afford 180 mg of the sulfonamide, a yellow solid in 51% yield.

Step 2: Using the procedure in Step 10 Example 1, the sulfonamide ester (60 mg, 0.080 mmol) was hydrolyzed to afford the 48 mg (81%) of the title product, a white solid. 1H NMR (400 MHz, CDCl$_3$) δ 1.89-2.01 (m, 2 H), 2.49 (s, 3 H), 2.75 (q, J=7.2 Hz, 4 H), 2.82-2.89 (m, 2 H), 2.90-2.98 (m, 2 H), 4.10-4.18 (m, 2 H), 4.76 (s, 2 H) broad, 6.48 (d, J=8.8 Hz, 1 H), 6.79 (dd, J=8.8, 2.3 Hz, 1 H), 6.86 (s, 1 H), 7.02-7.11 (m, J=6.6, 2.5 Hz, 4 H), 7.27-7.35 (m, 8 H), 7.38-7.47 (m, 2 H), 7.67 (d, J=7.8 Hz, 1 H), 8.00 (d, J=8.3 Hz, 2 H)

Example 10

4-(3-{5-chloro-1-(diphenylmethyl)-2-[2-({[2-(trifluoromethyl)benzyl]sulfonyl}amino)ethyl]-1H-indol-3-yl}propyl)benzoic acid Step 1: To a suspension of 4-{3-[2-(2-aminoethyl)-1-benzhydryl-5-chloro-1H-indol-3-yl]propyl}benzoic acid (prepared as described in U.S. Pat. No. 6,797,708 B2, incorporated herein by reference in its entirety) (10.0 g, 19 mmol) in CH$_3$CN (100 mL) and MeOH (25 mL) was added (trimethylsilyl)diazomethane (2.0 M soln. in hexanes, 9.6 mL, 19 mmol). After 16 h the mixture was filtered and concentrated to afford the methyl ester (8.8 g, ca. 86%), an orange foam, which was used without purification.

Step 2: As outlined in Step 9 Example 1, methyl 4-{3-[2-(2-aminoethyl)-1-benzhydryl-5-chloro-1H-indol-3-yl]propyl}benzoate (Example 1, Step 1, 9.1 g, 17 mmol) was reacted with (2-trifluoromethylphenyl)methanesulfonyl chloride (Example 5, Step 3, 4.8 g, 17 mmol) to afford 6.1 g of the sulfonamide, a white foam in 47% yield. $^1$H NMR (400 MHz, CDCl$_3$) δ 1.88-2.00 (m, 2 H), 2.64-2.77 (m, 6 H), 2.83-2.95 (m, 2 H), 3.90 (s, 3 H), 4.05 (t, J=5.9 Hz, 1 H), 4.33 (s, 2 H), 6.49 (d, J=8.8 Hz, 1 H), 6.70-6.88 (m, 2 H), 7.04 (dd, J=6.4, 2.7 Hz, 4 H), 7.24 (s, 1 H), 7.28-7.35 (m, 7 H), 7.36-7.49 (m, 3 H), 7.55-7.71 (m, 2 H), 7.95 (d, J=8.1 Hz, 2 H). In addition, the N-methyl sulfonamide byproduct (0.70 g, 5%) was obtained as a pale yellow foam. $^1$H NMR (400 MHz, CDCl$_3$) δ 1.82-2.02 (m, 2 H), 2.56 (s, 3 H), 2.63-2.78 (m, 4 H), 2.79-2.89 (m, 2 H), 2.89-3.01 (m, 2 H), 3.90 (s, 3 H), 4.29 (s, 2 H), 6.42 (d, J=8.8 Hz, 1 H), 6.77 (dd, J=8.8, 2.0 Hz, 1 H), 6.84 (s, 1 H), 6.98-7.11 (m, 4 H), 7.21-7.28 (m, 2 H), 7.28-7.35 (m, 6 H), 7.37-7.51 (m, 3 H), 7.63 (d, J=7.1 Hz, 1 H), 7.70 (d, J=8.6 Hz, 1 H), 7.95 (d, J=8.3 Hz, 2 H).

Step 3: Using the procedure in Step 10 Example 1, the methyl ester (2.6 g, 3.4 mmol) was hydrolyzed to afford 2.25 g (88%) of the title product, a yellow solid.

$^1$H NMR (400 MHz, DMSO-d$_6$) δ 1.81-1.97 (m, 2 H), 2.66-2.79 (m, 4 H), 2.95 (s, 4 H), 4.41 (s, 2 H), 6.45 (d, J=8.8 Hz, 1 H), 6.78 (dd, J=8.8, 2.0 Hz, 1 H), 7.01-7.14 (m, 5 H), 7.24-7.42 (m, 8 H), 7.46 (d, J=2.0 Hz, 1 H), 7.50-7.66 (m, 4 H), 7.73 (d, J=7.8 Hz, 1 H), 7.85 (d, J=8.3 Hz, 2 H), 12.77 (s, 1 H); HRMS: calcd for C$_{41}$H$_{36}$ClF$_3$N$_2$O$_4$S+H+, 745.21092. found (ESI-FTMS, [M+H]$^{1+}$), 745.2132; Anal. Calcd for C$_{41}$H$_{36}$ClF$_3$N$_2$O$_4$S: C, 66.08; H, 4.87; N, 3.76. Found: C, 66.07; H, 4.57; N, 3.67.

Example 11

4-(3-{5-chloro-1-(diphenylmethyl)-2-[2-(methyl{[2-(trifluoromethyl)benzyl]sulfonyl}amino)ethyl]-1H-indol-3-yl}propyl)benzoic acid Step 1: Using the procedure in Step 10 Example 1, the N-Me sulfonamide ester isolated from Example 10, Step 2 as a side product (0.66 g, 0.85 mmol) was hydrolyzed to afford 0.30 g (46%) of the title product, a pale yellow powder. $^1$H NMR (400 MHz, DMSO-d$_6$) δ 1.76-1.93 (m, 2 H), 2.63-2.81 (m, 9H), 3.31 (s, 2 H), 4.46 (s, 2 H), 6.46 (d, J=8.8 Hz, 1 H), 6.78 (dd, J=8.8, 2.3 Hz, 1 H), 6.98-7.13 (m, 5 H), 7.23-7.43 (m, 8 H), 7.46 (d, J=2.0 Hz, 1 H), 7.51-7.66 (m, 3 H), 7.72 (d, J=7.8 Hz, 1 H), 7.86 (d, J=8.3 Hz, 2 H), 12.75 (br s, 1 H); HRMS: calcd for C$_{42}$H$_{38}$ClF$_3$N$_2$O$_4$S+H+, 759.22657. found (ESI-FTMS, [M+H]$^{1+}$), 759.2269; HPLC purity H$_2$O/CH$_3$CN: 96.2%, H$_2$O/MeOH: 95.7%.

Example 12

4-{3-[2-[2-({[2,6-bis(trifluoromethyl)benzyl]sulfonyl}amino)ethyl]-5-chloro-1-(diphenylmethyl)-1H-indol-3-yl]propyl}benzoic acid Step 1: 2,6-Bis(trifluoromethyl)benzoyl fluoride. Using the procedure described by W. Dmowski and K. Piasecka-Maciejewska, *Tetrahedron Lett.* 1998, 54, 6781-6792, incorporated herein by reference in its entirety, 7.0 g of 2,6-bis(trifluoromethyl)benzoic acid was converted to the acid fluoride (7.0 g, 100%), an orange solid. $^1$H NMR (400 MHz, DMSO-d$_6$) δ 8.17 (t, J=8.0 Hz, 1 H), 8.40 (d, J=8.0 Hz, 2 H).

Step 2: 2,6-Bis(trifluoromethylphenyl)benzyl alcohol. Using the procedure described by W. Dmowski and K. Piasecka-Maciejewska, *Tetrahedron Lett.* 1998, 54, 6781-6792, incorporated herein by reference in its entirety, 7.0 g of 2,6-bis(trifluoromethyl)benzoyl fluoride was converted to the alcohol (6.6 g, 100%), a pale yellow oil. $^1$H NMR (400 MHz, CDCl$_3$) δ 4.95 (s, 2 H), 7.59 (t, J=8.0 Hz, 1 H), 7.94 (d, J=7.8 Hz, 2 H).

Step 3: 2,6-Bis(trifluoromethylphenyl)benzyl bromide. To a solution of 2,6-bis(trifluoromethylphenyl)benzyl alcohol (6.6 g, 28 mmol) and 1,3-bis(diphenylphosphino)propane (6.9 g, 17 mmol) in CH$_2$Cl$_2$ (50 mL) at 0° C. was slowly added carbon tetrabromide (11 g, 33 mmol). The mixture was stirred overnight at room temperature then added via pipette to 200 mL Et$_2$O. The mixture was filtered through Celite and concentrated. The yellow oil was suspended in 2% EtOAc-hex and filtered through a pad of SiO$_2$ to afford the bromide (7.2 g, 84%), a colorless oil. $^1$HNMR (400 MHz, CDCl$_3$), δ 4.78 (s, 2 H), 7.59 (t, J=7.9 Hz, 1 H), 7.92 (d, J=7.9 Hz, 2 H).

Step 4: 2,6-Bis(trifluoromethylphenyl)methanesulfonic acid sodium salt. A mixture of bis(trifluoromethylphenyl)benzyl bromide (7.2 g, 23 mmol), sodium sulfite (3.1 g, 25 mmol), tetrabutylammonium iodide (0.043 g, 0.1 mmol) and H$_2$O (20 mL) was heated to reflux for 2 d. The mixture was cooled to room temperature and the aqueous phase was decanted from the oily residue and concentrated on the rotovap to dryness to afford 2,6-bis(trifluoromethylphenyl)methanesulfonic acid sodium salt hydrobromide (3.2 g, 32%), a white solid, which was used without purification.

Step 5: 2,6-Bis(trifluoromethylphenyl)methanesulfonic acid. 2,6-Bis(trifluoromethylphenyl)methanesulfonic acid sodium salt (0.19 g, 0.44 mmol) was suspended in MeOH (5 mL) and cooled at −20° C. while HCl was bubbled through the mixture for 5 min. The resulting white suspension was stirred at room temperature for 1.5 h, filtered through Celite, and concentrated to afford 2,6-bis(trifluoromethylphenyl)methanesulfonic acid (0.14 g, 100%), an orange solid which was used without further purification. $^1$H NMR (400 MHz, DMSO-d$_6$) δ 4.25 (s, 2 H), 7.64 (t, J=8.5 Hz, 1 H), 7.96 (d, J=7.8 Hz, 2 H).

Step 6: 2,6-Bis(trifluoromethylphenyl)methanesulfonyl chloride. To a suspension of 2,6-bis(trifluoromethylphenyl)methanesulfonic acid (0.14 g, 0.44 mmol) in THF (10 mL) and DMF (0.05 mL) at −20° C. was added oxalyl chloride (0.24 mL, 2.7 mmol) slowly dropwise. The bath temperature was maintained below 0° C. for 4 h, then the reaction mixture was filtered through Celite and washed with THF (10 mL) and concentrated to ~5 mL total volume. The mixture was cooled to −40° C. and H$_2$O (0.3 mL) was added slowly. The mixture was extracted with EtOAc (2×10 mL), washed with sat. NaHCO$_3$ (20 mL), H$_2$O (20 mL), and brine (20 mL), dried (Na$_2$SO$_4$) and concentrated to afford 99 mg of crude product which was purified by low-temperature crystallization from hexanes to afford 2,6-bis(trifluoromethylphenyl)methanesulfonyl chloride (33 mg, 23%), a white powder. Concentration of the mother liquors afforded additional product (57 mg, 40%). $^1$H NMR (400 MHz, CDCl$_3$) δ 5.56 (s, 2 H), 7.70 (t, J=8.0 Hz, 1 H), 7.97 (d, J=8.0 Hz, 2 H).

Step 7: As outlined in Step 9 Example 1, methyl 4-{3-[2-(2-aminoethyl)-1-benzhydryl-5-chloro-1H-indol-3-yl]propyl}benzoate (Example 5, Step 6, 148 mg, 0.27 mmol) was reacted with 2,6-bis(trifluoromethylphenyl)methanesulfonyl chloride (90 mg, 0.27 mmol) to afford 137 mg of the sulfonamide, a pale yellow foam in 60% yield. $^1$H NMR (400 MHz, CDCl$_3$) δ 1.83-2.03 (m, 2 H), 2.68-2.78 (m, 4 H), 2.79-2.91 (m, 2 H), 2.92-3.03 (m, 2 H), 3.89 (s, 3 H), 4.21 (t, J=6.4 Hz, 1 H), 4.66 (s, 2 H), 6.51 (d, J=9.1 Hz, 1 H), 6.81 (dd, J=8.7, 2.1 Hz, 1 H), 6.87 (s, 1 H), 7.00-7.11 (m, 4 H), 7.21-7.28 (m, 4 H), 7.28-7.35 (m, 4 H), 7.41 (d, J=1.5 Hz, 1 H), 7.59 (t, J=7.7 Hz, 1 H), 7.89 (d, J=7.8 Hz, 2 H), 7.95 (d, J=8.1 Hz, 2 H).

Step 8: Using the procedure in Step 10 Example 1, the sulfonamide ester (119 mg, 0.14 mmol) was hydrolyzed to afford 97 mg (83%) of the title product, a yellow solid. $^1$H NMR (400 MHz, DMSO-$d_6$) δ 1.75-1.95 (m, 2 H), 2.73 (q, J=7.5 Hz, 4 H), 2.97 (s, 4 H), 4.67 (s, 2 H), 6.45 (d, J=8.8 Hz, 1 H), 6.79 (dd, J=8.8, 2.0 Hz, 1 H), 7.04 (s, 1 H), 7.06-7.16 (m, 4 H), 7.27-7.43 (m, 8 H), 7.47 (d, J=2.0 Hz, 1 H), 7.75 (t, J=5.2 Hz, 1 H), 7.77-7.91 (m, 3 H), 8.10 (d, J=8.1 Hz, 2 H), 12.78 (s, 1 H); HRMS: calcd for $C_{42}H_{35}ClF_6N_2O_4S+H+$, 813.19830. found (ESI-FTMS, [M+H]$^{1+}$), 813.1965. HPLC purity $H_2O$/$CH_3CN$: 95.5%, $H_2O$/MeOH: 96.8%.

Example 13

4-(3-{5-chloro-1-(diphenylmethyl)-2-[2-({[2-(methoxycarbonyl)benzyl]sulfonyl}amino)ethyl]-1H-indol-3-yl}propyl)benzoic acid Step 1: To a mixture of methyl 2-methylbenzoate (5.0 g, 0.033 mmol) and N-bromosuccinimide (5.9 g, 0.033 mmol) in $CCl_4$ (50 mL) was added benzoyl peroxide (0.04 g, 0.00016 mmol). The mixture was heated to reflux for 1.5 h, cooled to room temperature, filtered through Celite, and concentrated to afford methyl 2-(bromomethyl)benzoate (7.2 g, ca. 94% mass recovery), which was contaminated with ca. 14% unreacted starting material and was used without purification.

Step 2: A mixture of the crude bromide from Step 1 (7.2 g, 0.031 mmol) and thiourea (2.6 g, 35 mmol) in MeOH (40 mL) was heated to reflux for 4 h, cooled to room temperature, and concentrated to afford methyl 2-({[amino(imino)methyl]thio}methyl)benzoate hydrobromide (10 g, ca. 100%), which was used without purification.

Step 3: The isothiouronium salt from Step 2 (10 g, 0.031 mmol) was suspended in $H_2O$ (100 mL) and cooled to 0° C. Chlorine gas was bubbled into the mixture for 30 min. The ice bath was removed and the reaction mixture was poured into a separatory funnel and diluted with EtOAc (250 mL). The organic phase was separated and washed with sat. $NaHCO_3$ (100 mL), $H_2O$ (100 mL), and brine (100 mL), dried ($MgSO_4$) and concentrated to afford an orange solid (6.48 g). The crude product was recrystallized from 20% EtOAc-hexanes at −78° C. to afford 3.63 g (47%) of methyl 2-[(chlorosulfonyl)methyl]benzoate, as pale yellow crystals.

Step 4: To a suspension of 4-{3-[2-(2-aminoethyl)-1-benzhydryl-5-chloro-1H-indol-3-yl]propyl}benzoic acid (0.40 g, 0.76 mmol) in $CH_2Cl_2$ (5 mL) was added bis(trimethylsilyl)trifluoroacetamide (0.30 mL, 0.29 g, 1.1 mmol). The mixture was heated to reflux for 30 min, then cooled to 35° C. Pyridine (0.16 mL, 0.15 g, 2.0 mmol) was added, followed by a solution of methyl 2-[(chlorosulfonyl)methyl]benzoate from Step 3 (0.29 g, 1.1 mmol) in $CH_2Cl_2$ (2 mL). After 5 h, the mixture was cooled to room temperature. A solution of conc. HCl (0.17 mL) in $H_2O$ (5 mL) was added and the mixture was stirred for 45 min. The aqueous phase was separated and extracted with $CH_2Cl_2$ (50 mL). The combined organic extracts were washed with $H_2O$ (25 mL) and brine (25 mL), dried ($MgSO_4$) and concentrated to afford a gold foam (0.40 g). Purification by prep HPLC afforded the title compound (70 mg, 12%), a pale yellow foam. $^1$H NMR (400 MHz, DMSO-$d_6$) δ 1.87-2.10 (m, 2 H), 2.85 (t, J=6.6 Hz, 4 H), 3.03 (s, 2 H), 3.48 (s, 2 H), 3.86 (s, 3 H), 4.94 (s, 2 H), 6.57 (d, J=8.8 Hz, 1 H), 6.92 (dd, J=8.8, 2.3 Hz, 1 H), 7.14 (s, 1 H), 7.17-7.29 (m, 4 H), 7.43-7.57 (m, 10 H), 7.57-7.69 (m, 3 H), 7.90-7.97 (m, 1 H), 8.00 (d, J=8.3 Hz, 2 H), 12.93 (s, 1 H), HRMS: calcd for $[C_{42}H_{39}ClN_2O_6S_1—H]^{1-}$, 733.2144. found (ESI-FTMS, [M−H]$^{1-}$), 733.2141; HPLC purity $H_2O$/$CH_3CN$: 95.3%, $H_2O$/MeOH: 100%.

Example 14

4-(3-{5-chloro-1-(diphenylmethyl)-2-[2-({[2-fluoro-6-(trifluoromethyl)benzyl]sulfonyl}amino)ethyl]-1H-indol-3-yl}propyl)benzoic acid Step 1: Using the procedure described in Example 5, Step 1,2-fluoro-6-(trifluoromethylphenyl)benzyl bromide (15 g, 61 mmol) afforded 2-fluoro-6-(trifluoromethylphenyl)methanesulfonic acid sodium salt (15 g, 89%), a white solid. $^1$HNMR (400 MHz, DMSO-$d_6$) δ 4.02 (s, 2 H), 7.26-7.66 (m, 3 H).

Step 2: Using the procedure described in Example 5, Step 2,2-fluoro-6-(trifluoromethylphenyl)methanesulfonic sodium salt (15 g, 53 mmol) afforded 2-fluoro-6-(trifluoromethylphenyl)methanesulfonic acid (15 g), a pale orange oil which was used without further purification. $^1$H NMR (400 MHz, DMSO-$d_6$) δ 4.12 (s, 2 H), 7.39-7.73 (m, 3 H).

Step 3: Using the procedure described in Example 5, Step 3,2-fluoro-6-(trifluoromethylphenyl)methanesulfonic acid (15 g, 53 mmol) afforded 11 g of crude product which was purified by low-temperature crystallization from hexanes to afford 2-fluoro-6-(trifluoromethylphenyl)methanesulfonyl chloride (9.0 g, 62%). $^1$H NMR (400 MHz, $CDCl_3$) δ 5.31 (s, 2 H), 7.38-7.51 (m, 1 H), 7.58-7.68 (m, 2 H).

Step 4: As outlined in Step 9 Example 1, methyl 4-{3-[2-(2-aminoethyl)-1-benzhydryl-5-chloro-1H-indol-3-yl]propyl}benzoate (Example 7, Step 6, 0.12 g, 0.22 mmol) was reacted with 2-fluoro-6-(trifluoromethylphenyl)methanesulfonyl chloride, 0.074 g, 0.27 mmol) to afford 0.127 g of the sulfonamide, a pale yellow foam, in 73% yield. $^1$H NMR (400 MHz, $CDCl_3$) δ 1.79-2.02 (m, 2 H), 2.74 (t, J=8.0 Hz, 4 H), 2.82-2.92 (m, 2 H), 2.92-3.02 (m, 2 H), 3.89 (s, 3 H), 4.15 (t, J=5.8 Hz, 1 H), 4.42 (d, 2 H), 6.50 (d, J=8.6 Hz, 1 H), 6.80 (dd, J=8.8, 2.0 Hz, 1 H), 6.87 (s, 1 H), 7.07 (dd, J=6.4, 2.7 Hz, 4 H), 7.19-7.28 (m, 5 H), 7.29-7.35 (m, 5 H), 7.39-7.56 (m, 2 H), 7.95 (d, J=8.3 Hz, 2 H).

Step 4: Using the procedure in Step 10 Example 1, the sulfonamide ester (115 mg, 0.15 mmol) was hydrolyzed to afford 101 mg (89%) of the title product, a pale yellow powder. $^1$H NMR (400 MHz, DMSO-$d_6$) δ 1.80-1.95 (m, 2 H), 2.63-2.78 (m, 4 H), 2.88-3.14 (m, 4 H), 4.45 (s, 2 H), 6.43 (d, J=8.8 Hz, 1 H), 6.76 (dd, J=8.8, 2.3 Hz, 1 H), 6.96-7.15 (m, 5 H), 7.20-7.41 (m, 8 H), 7.45 (d, J=2.3 Hz, 1 H), 7.50-7.59 (m, 1 H), 7.59-7.66 (m, 2 H), 7.71 (t, J=5.6 Hz, 1 H), 7.83 (d, J=8.3 Hz, 2 H), 12.73 (s, 1 H); HRMS: calcd for $C_{41}H_{35}ClF_4N_2O_4S+H+$, 763.20149. found (ESI-FTMS, [M+H]$^{1+}$), 763.1998; HPLC purity $H_2O$/$CH_3CN$: 95.4%, $H_2O$/MeOH: 96.4%.

Example 15

4-[3-(5-chloro-1-(diphenylmethyl)-2-{2-[({2-[2-(trifluoromethyl)phenyl]ethyl}sulfonyl)amino]ethyl}-1H-indol-3-yl)propyl]benzoic acid Step 1: 2-(Trifluoromethyl)phenethyl alcohol (5.0 g, 26 mmol) was treated with $CBr_4$ as in Example 12, Step 3 to afford the bromide (6.6 g, 100%) which was used without purification.

Step 2: The bromide from Step 1 (1.5 g, 5.9 mmol) was treated with thiourea as in Example 13, Step 2 to afford the isothiouronium salt (2.2 g) a wet white solid, which was used without purification.

Step 3: The isothiouronium salt from Step 2 (2.2 g, ~5.9 mmol) was suspended in $H_2O$ and treated with $Cl_2$ gas as in Example 13, Step 3 and an orange oil (1.15 g) was obtained. To the crude product was added hexanes (75 mL) and the mixture was heated at 60° C. for 4 h. The hexanes soluble fraction was decanted and cooled to −78° C. to afford a white solid (0.13 g, ca. 7% yield, 2 steps) which was used without purification.

Step 4: As outlined in Step 9 Example 1, methyl 4-{3-[2-(2-aminoethyl)-1-benzhydryl-5-chloro-1H-indol-3-yl]propyl}benzoate (Example 7, Step 6, 98 mg, 0.18 mmol) was reacted with (2-trifluoromethylphenyl)ethanesulfonyl chloride from Step 3, (75 mg, 0.28 mmol) to afford 70 mg of the sulfonamide, a white foam in 50% yield. $^1H$ NMR (400 MHz, $CDCl_3$) δ 1.88-2.03 (m, 2 H), 2.70-2.83 (m, 4 H), 2.88-3.07 (m, 6 H), 3.07-3.23 (m, 2 H), 3.90 (s, 3 H), 4.07 (t, J=6.2 Hz, 1 H), 6.51 (d, J=8.8 Hz, 1 H), 6.72-6.86 (m, 1 H), 6.90 (s, 1 H), 7.07 (d, J=6.8 Hz, 4 H), 7.17-7.32 (m, 9H), 7.35 (t, J=7.6 Hz, 1 H), 7.41 (d, J=2.0 Hz, 1 H), 7.48 (t, J=6.9 Hz, 1 H), 7.63 (d, J=7.8 Hz, 1 H), 7.95 (d, J=8.3 Hz, 2 H).

Step 5: Using the procedure in Step 10 Example 1, the sulfonamide ester (70 mg, 0.09 mmol) was hydrolyzed to afford 54 mg (78%) of the title product, a white powder. $^1H$ NMR (400 MHz, DMSO-$d_6$) δ 1.82-2.22 (m, 2 H), 2.68-2.90 (m, 4 H), 2.99-3.24 (m, 8 H), 6.50 (d, J=8.8 Hz, 1 H), 6.83 (dd, J=8.8, 2.3 Hz, 1 H), 7.15 (appar d, J=6.8 Hz, 5 H), 7.32-7.44 (m, 8 H), 7.45-7.55 (m, 3 H), 7.59 (t, J=5.7 Hz, 1 H), 7.65 (t, J=7.3 Hz, 1 H), 7.75 (d, J=7.8 Hz, 1 H), 7.83-7.98 (m, J=8.3 Hz, 2 H), 12.83 (s, 1 H); HRMS: calcd for $C_{42}H_{38}ClF_3N_2O_4S$+H+, 759.22657. found (ESI-FTMS, [M+H]$^{1+}$), 759.2277; HPLC purity $H_2O/CH_3CN$: 96.0%, $H_2O/MeOH$: 98.0%.

Example 16

4-{3-[5-chloro-1-(diphenylmethyl)-2-(2-{[(2-formyl-benzyl)sulfonyl]amino}ethyl)-1H-indol-3-yl]propyl}benzoic acid Step 1: To α-bromo-o-tolunitrile (10 g, 51 mmol) in $CH_2Cl_2$ at 0° C. was added DIBAL-H (1M in hexane, 55 mL, 55 mmol) and the reaction mixture was stirred at the same temperature for 3.5 h, then poured into a solution of cold 5% HBr at 0° C. The mixture was stirred for 15 min, then the layers were separated and the aqueous layer was extracted with $CH_2Cl_2$ and the combined organic layers were washed with $NaHCO_3$ and water, dried over $MgSO_4$ and evaporated to yield a dark liquid (9.4 g). The material was used directly in the next step without further purification.

Step 2: (2-Formyl-phenyl)-methanesulfonic acid sodium salt: Using the procedure described in Example 5, Step 1,2-bromomethyl-benzaldehyde (1.58 g, 7.94 mol) afforded (2-formyl-phenyl)-methanesulfonic acid sodium salt (1.40 g, 80%), an off white solid.

Step 3: (2-Formyl-phenyl)-methanesulfonic acid: Using the procedure described in Example 5, Step 3, (2-formyl-phenyl)-methanesulfonic acid sodium salt (1.40 g, 6.30 mmol) afforded (2-formyl-phenyl)-methanesulfonic acid (418 mg, 33%), a pale yellow solid.

Step 4: (2-Formyl-phenyl)-methanesulfonyl chloride: Using the procedure described in Example 5, Step 4, (2-formyl-phenyl)methanesulfonic acid (418 mg, 2.09 mmol) afforded (2-formyl-phenyl)-methanesulfonyl chloride (367 mg, 80%). $^1HNMR$ (400 MHz, $CDCl_3$) δ 10.15 (s, 1 H), 7.92 (dd, 1 H), 7.74-7.61 (m, 3 H), 5.67 (s, 2 H).

Step 5: As outlined in Step 9 Example 1, methyl 4-{3-[2-(2-aminoethyl)-1-benzhydryl-5-chloro-1H-indol-3-yl]propyl}benzoate (Example 7, Step 6, 63 mg, 0.12 mmol) was reacted with (2-formyl-phenyl)-methanesulfonyl chloride (36 mg, 0.16 mmol) to afford 34 mg (40%) of the sulfonamide, a yellow solid.

Step 6: Using the procedure in Step 10 Example 1, the sulfonamide ester (28 mg, 0.039 mmol) was hydrolyzed to afford the 17 mg (62%) of the title product, a white solid.

Example 17

4-(3-{5-chloro-1-(diphenylmethyl)-2-[2-({[2-(morpholin-4-ylmethyl)benzyl]sulfonyl}amino)ethyl]-1H-indol-3-yl}propyl)benzoic acid Step 1: To methyl 4-{3-[5-chloro-1-(diphenylmethyl)-2-(2-{[(2-formylbenzyl)sulfonyl]amino}ethyl)-1H-indol-3-yl]propyl}benzoate (Example 16, Step 5, 58 mg, 0.081 mmol) in DCE (2 mL) at 0° C. were added morpholine (0.0092 mL, 0.105 mmol) and NaBH(OAc)$_3$ (27 mg, 0.13 mmol) and the reaction mixture was allowed to warm to rt overnight. The reaction was quenched with sat. $NaHCO_3$, extracted with EtOAc, and dried over $MgSO_4$. Purification by silica gel chromatography (35% to 50% EtOAc/hexanes) gave the desired product as a white solid (41 mg, 64%).

Step 2. Using the procedure in Step 10 Example 1, the sulfonamide ester (18 mg, 0.039 mmol) was hydrolyzed to afford the 15 mg (83%) of the title product, a white solid.

Example 18

4-{3-[5-chloro-2-{2-[({2-[(diethylamino)methyl]benzyl}sulfonyl)amino]ethyl}-1-(diphenylmethyl)-1H-indol-3-yl]propyl}benzoic acid Step 1: As outlined in Example 17, Step 1 methyl 4-{3-[5-chloro-1-(diphenylmethyl)-2-(2-{[(2-formylbenzyl)sulfonyl]amino}ethyl)-1H-indol-3-yl]propyl}benzoate (Example 16, Step 5, 58 mg, 0.081 mmol) was reacted with $HNEt_2$ (0.022 mL, 0.21 mmol) and NaBH(OAc)$_3$ (56 mg, 0.26 mmol) in DCE (2 mL) to afford methyl 4-{3-[5-chloro-2-{2-[({2-[(diethylamino)methyl]benzyl}sulfonyl)amino]ethyl}-1-(diphenylmethyl)-1H-indol-3-yl]propyl}benzoate (26 mg, 41%) and the side product methyl 4-(3-{5-chloro-1-(diphenylmethyl)-2-[2-({[2-(hydroxymethyl)benzyl]sulfonyl}amino)ethyl]-1H-indol-3-yl}propyl)benzoate (8.6 mg, 15%), both as white solids.

Step 2. Using the procedure in Step 10 Example 1, methyl 4-{3-[5-chloro-2-{2-[({2-[(diethylamino)methyl]benzyl}sulfonyl)amino]ethyl}-1-(diphenylmethyl)-1H-indol-3-yl]propyl}benzoate (20 mg, 0.026 mmol) was hydrolyzed to afford the 13 mg (66%) of the title product, a white solid.

Example 19

4-(3-{5-chloro-1-(diphenylmethyl)-2-[2-({[2-(hydroxymethyl)benzyl]sulfonyl}amino)ethyl]-1H-indol-3-yl}propyl)benzoic acid Step 1. Using the procedure in Step 10 Example 1, the side product from Example 18 Step 1, methyl 4-(3-{5-chloro-1-(diphenylmethyl)-2-[2-({[2-(hydroxymethyl)benzyl]sulfonyl}amino)ethyl]-1H-indol-3-yl}propyl)benzoate (8.4 mg, 0.0012 mmol) was hydrolyzed to afford the 5.0 mg (61%) of the title product, a white solid.

Example 20

4-(3-{5-chloro-1-(diphenylmethyl)-2-[2-({[2-(piperazin-1-ylmethyl)benzyl]sulfonyl}amino)ethyl]-1H-indol-3-yl}propyl)benzoic acid and Example 21 4-{3-[2-{2-[({2-[(4-acetylpiperazin-1-yl)methyl]benzyl}sulfonyl)amino]ethyl}-5-chloro-1-(diphenylmethyl)-1H-indol-3-yl]propyl}benzoic acid Step 1: As outlined in Example 17, Step 1, methyl 4-{3-[5-chloro-1-(diphenylmethyl)-2-(2-{[(2-formylbenzyl)sulfonyl]amino}ethyl)-1H-indol-3-yl]propyl}benzoate (Example 16, Step 5, 45 mg, 0.063 mmol) was reacted with 1-acetylpiperazine (28 mg, 0.22 mmol) and NaBH(OAc)$_3$ (26 mg, 0.12 mmol) in DCE (3 mL) to afford the sulfonamide (39 mg, 75%) as a white foam.

Step 2. Using the procedure in Step 10 Example 1, the sulfonamide (37 mg, 0.045 mmol) was hydrolyzed to afford, after preparative HPLC separation, methyl 4-(3-{5-chloro-1-(diphenylmethyl)-2-[2-({[2-(piperazin-1-ylmethyl)benzyl]sulfonyl}amino)ethyl]-1H-indol-3-yl}propyl)benzoate (7.4 mg, 21%) and methyl 4-{3-[2-{2-[({2-[(4-acetylpiperazin-1-yl)methyl]benzyl}sulfonyl)amino]ethyl}-5-chloro-1-(diphenylmethyl)-1H-indol-3-yl]propyl}benzoate (7.7 mg, 21%), both as solids.

Example 22

4-[3-(5-chloro-1-(diphenylmethyl)-2-{2-[({2-[(4-methylpiperazin-1-yl)methyl]benzyl}sulfonyl)amino]ethyl}-1H-indol-3-yl)propyl]benzoic acid Step 1: As outlined in Example 17, Step 1, methyl 4-{3-[5-chloro-1-(diphenylmethyl)-2-(2-{[(2-formylbenzyl)sulfonyl]amino}ethyl)-1H-indol-3-yl]propyl}benzoate (Example 16, Step 5, 44 mg, 0.061 mmol) was reacted with 1-methylpiperazine (0.026 mL, 0.23 mmol) and NaBH(OAc)$_3$ (34 mg, 0.16 mmol) in DCE (3 mL) to afford the sulfonamide (41 mg, 84%) as white solid.

Step 2: Using the procedure in Step 10 Example 1, the sulfonamide (39 mg, 0.026 mmol) was hydrolyzed to afford the 27 mg (69%) of the title product, a white solid.

Example 23

4-[3-(5-chloro-1-(diphenylmethyl)-2-{2-[({1-[2-(trifluoromethyl)phenyl]ethyl}sulfonyl)amino]ethyl}-1H-indol-3-yl)propyl]benzoic acid Step 1: To α-methyl-2-triflouromethyl benzyl bromide (10.0 g, 39.5 mmol) in DMF (50 mL) added potassium thioacetate (8.1 g, 71.1 mmol) according to the procedure outlined in Example 3, Step 2. This afforded the thioacetate as an orange oil (10.49 g, 91%).

Step 2: The thioacetate from Step 1 (10.49 g, 36.1 mmol) and sodium acetate (21.5 g, 155.4 mmol) was dissolved in a mixture of acetic acid (137 mL) and water (31 mL) and chlorine gas was bubbled in according to the procedure in Example 3, Step 3. This yielded upon concentration and low-temperature recrystallization from hexanes an off white solid that later melted into a pale orange oil (4.9 g, 47%). $^1$H NMR (400 MHz, CDCl$_3$) δ 2.01 (d, J=6.8 Hz, 3 H) 5.32 (q, J=7.1 Hz, 1 H) 7.56 (t, J=6.7 Hz, 1 H) 7.67 (t, J=7.8 Hz, 1 H) 7.77 (d, J=7.8 Hz, 1 H) 7.91 (d, J=8.1 Hz, 1 H)

Step 3: Using the procedure in Example 1, Step 9, 4-{3-[2-(2-amino-ethyl)-1-benzhydryl-5-chloro-1H-indol-3-yl]-propyl}-benzoic acid methyl ester (Example 7, Step 6, 0.123 g, 0.23 mmol) was reacted with 1-(2-trifluoromethyl-phenyl)-ethanesulfonyl chloride (0.79 g, 0.29 mmol) to afford 0.042 g of a racemic mixture of sulfonamides in 24% yield.

Step 4: The sulfonamide ester (0.042 g, 0.054 mmol) was hydrolyzed according to Example 1, Step 10, to afford 0.035 g (85%) of the title product, a pale orange solid.

1H NMR (400 MHz, CDCl$_3$) δ 1.68 (d, J=7.1 Hz, 3 H) 1.93 (t, J=5.4 Hz, 2 H) 2.02-2.08 (m, 1 H) 2.63-2.77 (m, 6 H) 2.86 (t, J=7.6 Hz, 2 H) 6.47 (d, J=8.8 Hz, 1 H) 7.01-7.07 (m, 4 H) 7.24-7.40 (m, 12H) 7.44 (t, J=7.5 Hz, 1 H) 7.60 (d, J=7.6 Hz, 1 H) 7.85 (d, J=8.1 Hz, 1 H) 8.00 (d, J=8.1 Hz, 2 H)

Example 24

4-{3-[2-(2-{[(2-bromobenzyl)sulfonyl]amino}ethyl)-5-chloro-1-(diphenylmethyl)-1H-indol-3-yl]propyl}benzoic acid Step 1: Using the procedure in Step 9 Example 1, methyl 4-{3-[2-(2-aminoethyl)-1-benzhydryl-5-chloro-1H-indol-3-yl]propyl}benzoate (Example 7, Step 6, 1.51 g, 2.81 mmol) was reacted with 2-bromo-phenyl-methanesulfonyl chloride to afford 1.06 g of the sulfonamide, a white solid, in 49% yield.

Step 2: As described in example 1, step 10, the sulfonamide ester (90 mg, 0.117 mmol) was hydrolyzed to afford the 81 mg (91%) of the title product, a white solid. 1H NMR (400 MHz, CDCl$_3$) δ 1.89-2.02 (m, 2 H), 2.68-2.78 (m, 4 H), 2.78-2.87 (m, 2 H), 2.89-2.97 (m, 2 H), 4.21 (t, J=5.1 Hz, 1 H), 4.37 (s, 2 H), 6.48 (d, J=8.8 Hz, 1 H), 6.79 (dd, J=8.8, 2.0 Hz, 1 H), 6.84 (s, 1 H), 7.00-7.08 (m, 4 H), 7.09-7.17 (m, 1 H), 7.17-7.24 (m, 1 H), 7.25-7.34 (m, 8 H), 7.36-7.45 (m, 2 H), 7.49 (dd, J=8.1, 1.3 Hz, 1 H), 8.01 (d, J=8.3 Hz, 2 H). HRMS: calcd for $C_{40}H_{36}BrClN_2O_4S+H+$, 755.13404. found (ESI-FTMS, [M+H]$^{1+}$), 755.1341.

Example 25

4-(3-{5-chloro-1-(diphenylmethyl)-2-[2-({[2-(trifluoromethoxy)benzyl]sulfonyl}amino)ethyl]-1H-indol-3-yl}propyl)benzoic acid Step 1: Using the procedure in Example 1, Step 9, methyl 4-{3-[2-(2-aminoethyl)-1-benzhydryl-5-chloro-1H-indol-3-yl]propyl}benzoate (Example 7, Step 6, 164 mg, 0.305 mmol) was reacted with 2-trifluoromethoxy-phenyl-methanesulfonyl chloride to afford 109 mg of the sulfonamide, a white solid in 46% yield.

Step 2: As described in Example 1, Step 10, the sulfonamide ester (83 mg, 0.107 mmol) was hydrolyzed to afford the 80 mg (98%) of the title product, a white solid. 1H NMR (400 MHz, CDCl$_3$) δ 1.86-2.03 (m, 2 H), 2.74 (q, J=7.6 Hz, 4 H), 2.76-2.86 (m, 2 H), 2.90-3.00 (m, 2 H), 4.12 (t, J=6.2 Hz, 1 H), 4.19 (s, 1 H), 6.49 (d, J=8.8 Hz, 1 H), 6.80 (dd, J=8.8, 2.3 Hz, 1 H), 6.85 (s, 1 H), 7.00-7.11 (m, 4 H), 7.16-7.23 (m, 2 H), 7.24-7.28 (m, 2 H), 7.28-7.37 (m, 8 H), 7.39-7.44 (m, 2 H), 8.00 (d, 2 H). HRMS: calcd for $C_{41}H_{36}ClF_3N_2O_5S+H+$, 761.20583. found (ESI-FTMS, [M+H]$^{1+}$), 761.2057.

Example 26

4-{3-[5-chloro-2-(2-{[(3-chloro-6-fluoro-2-methyl-benzyl)sulfonyl]amino}ethyl)-1-(diphenylmethyl)-1H-indol-3-yl]propyl}benzoic acid Step 1: 2,6-Difluoro-N-(2-hydroxy-1,1-dimethyl-ethyl)-benzamide. To a 0° C. solution of 2-amino-2-methylpropanol (10.1 g, 113.3 mmol) in $CH_2Cl_2$ (75 mL) under nitrogen was added dropwise a solution of 2,6-difluorobenzoyl chloride (10.0 g, 56.6 mmol) in $CH_2Cl_2$ (50 mL). The reaction mixture was then warmed to room temperature and stirred overnight. The reaction mixture was diluted with $H_2O$, and the aqueous phase was extracted with $CH_2Cl_2$, dried ($MgSO_4$) and concentrated. Purification via trituration with hexanes afforded 12.05 g (93%) of the amide, a white solid. $^1H$ NMR (400 MHz, $CDCl_3$) δ 1.41 (s, 6 H), 3.66-3.75 (m, 2 H), 3.77-3.87 (m, 1 H), 5.94 (s, 1 H), 6.90-6.99 (m, 2 H), 7.31-7.41 (m, 1 H).

Step 2: 2-(2,6-Difluorophenyl)-4,4-dimethyl-4,5-dihydro-oxazole. To a 0° C. solution of the amide from Step 1 (11.9 g, 51.9 mmol) in $CH_2Cl_2$ (50 mL) was added thionyl chloride (6.4 ml, 88.3 mmol). The reaction mixture was allowed to warm to room temperature. After 4 h, the reaction mixture was concentrated and triturated with $Et_2O$. The residue was taken up in $H_2O$, basified with 6N NaOH and extracted with EtOAc. The combined organic phase was washed with brine, dried ($MgSO_4$) and concentrated to afford 9.42 g (86%) of the dihydrooxazole, a white solid. $^1H$ NMR (400 MHz, $CDCl_3$) δ 1.42 (s, 6 H), 4.13 (s, 2 H), 6.90-7.02 (m, 2 H), 7.32-7.44 (m, 1 H).

Step 3: 2-(2-Fluoro-6-methyl-phenyl)-4,4-dimethyl-4,5-dihydro-oxazole. To a 0° C. solution of the dihydrooxazole from Step 2 (9.18 g, 43.5 mmol) in THF (140 mL) under argon was added dropwise methylmagnesium chloride (3.0 M solution in THF, 43.5 mL, 130 mmol). After 2 h the ice bath was removed and the mixture was stirred overnight at room temperature. The reaction mixture was quenched with a saturated aq. $NH_4Cl$ solution and extracted with EtOAc. The combined organic phase was washed with brine, dried ($MgSO_4$) and concentrated to afford 8.64 g (96%) of the dihydrooxazole, a clear colorless oil. $^1H$ NMR (400 MHz, $CDCl_3$) δ 1.42 (s, 6 H), 2.40 (s, 3 H), 4.11 (s, 2 H), 6.92 (t, J=9.0 Hz, 1 H), 6.99 (d, J=7.6 Hz, 1 H), 7.21-7.30 (m, 1 H).

Step 4: 2-Fluoro-6-methyl-benzoic acid. To a solution of the dihydrooxazole from Step 3 (8.43 g, 40.7 mmol) in $CH_3CN$ (70 mL) was added methyl iodide (9.2 mL, 146 mmol) and the mixture was heated to reflux for 6 h. The reaction mixture was then cooled to room temperature and stirred overnight. The reaction mixture was concentrated and the residue was triturated with $Et_2O$. The residue was taken up in equal parts 20% NaOH and methanol and heated to reflux for 6 h. The reaction mixture was cooled to room temperature and concentrated to remove organic solvents. The aqueous phase was washed several times with EtOAc and acidfied to pH 1. The aqueous phase was extracted with EtOAc. The combined organic phase was washed with brine, dried ($MgSO_4$) and concentrated to afford 3.67 g (58%) of the benzoic acid, a white solid. $^1H$ NMR (400 MHz, $CDCl_3$) δ 2.52 (s, 3 H) 6.99 (t, J=9.09 Hz, 1 H) 7.05 (d, J=7.83 Hz, 1 H) 7.31-7.41 (m, 1 H).

Step 5: To a solution of the acid from Step 4 (3.60 g, 23.4 mmol) in thionyl chloride (40 mL) was added DMF (0.42 mL) and the mixture was heated to reflux for 5.5 h. The mixture was cooled to room temperature and concentrated. The residue was taken up in THF (40 mL) and added over 20 min to a 0° C. slurry of $NaBH_4$ (3.53 g, 93.4 mmol) in THF (40 mL). The mixture was stirred at room temperature for 2 h and then quenched by the addition of $H_2O$ and 4 M HCl and extracted with EtOAc. The combined organic phase was washed with sat. $NaHCO_3$ and brine, dried ($MgSO_4$) and concentrated to afford 2.67 g (~75%) of the benzyl alcohol, a pale yellow solid. $^1H$ NMR (400 MHz, $CDCl_3$) δ 2.42 (s, 3 H), 4.72 (s, 2 H), 6.88 (t, J=9.0 Hz, 1 H), 6.96 (d, J=7.6 Hz, 1 H), 7.07-7.20 (m, 1 H).

Step 6: To a solution of the benzyl alcohol from Step 5 (2.65 g, 18.9 mmol) in $CH_2Cl_2$ (15 mL) was added 1,3-bis(diphenylphosphino)propane (4.7 g, 11 mmol). The mixture was cooled to 0° C. and $CBr_4$ (7.4 g, 22 mmol) was added slowly. The mixture was stirred overnight at room temperature. The mixture was diluted with $CH_2Cl_2$ (50 mL) and poured into $Et_2O$ (75 mL). The mixture was filtered and the solution phase was concentrated. The resulting product was again dissolved in $CH_2Cl_2$ (75 mL) and poured into $Et_2O$ (100 mL). Filtration and concentration afforded 3.27 g (85%) of the bromide, an orange oil. $^1H$ NMR (400 MHz, $CDCl_3$) δ 2.42 (s, 3 H), 4.56 (d, J=1.5 Hz, 2 H), 6.91 (t, J=9.1 Hz, 1 H), 6.97 (d, J=7.6 Hz, 1 H), 7.08-7.24 (m, 1 H).

Step 7: Using the procedure from Example 3, Step 2, the benzyl bromide from Step 6 (3.27 g, 16.1 mmol) was reacted with potassium thioacetate to afford 3.17 g (98%) of the benzyl thioacetate, a brown oil. $^1H$ NMR (400 MHz, $CDCl_3$) δ 2.35 (s, 6 H), 4.22 (d, J=1.5 Hz, 2 H), 6.88 (t, J=9.0 Hz, 1 H), 6.95 (d, J=7.6 Hz, 1 H), 7.06-7.21 (m, 1 H).

Step 8: Using the procedure from Example 3, Step 3, the benzyl thioacetate (3.17 g, 16.0 mmol) was oxidized to afford 3.30 g (80%) of (3-chloro-6-fluoro-2-methyl-phenyl)-methanesulfonyl chloride, a tan solid. $^1H$ NMR (400 MHz, $CDCl_3$) δ 2.52 (s, 3 H), 5.10 (d, J=1.3 Hz, 2 H), 7.02 (t, J=9.0 Hz, 1 H), 7.48 (dd, J=9.1, 5.3 Hz, 1 H).

Step 9: Using the procedure in Step 9, Example 1, methyl 4-{3-[2-(2-aminoethyl)-1-benzhydryl-5-chloro-1H-indol-3-yl]propyl}benzoate (Example 7, Step 6, 163 mg, 0.303 mmol) was reacted with (3-chloro-6-fluoro-2-methyl-phenyl)-methanesulfonyl chloride from Step 8 to afford 102 mg of the sulfonamide, a white solid in 44% yield.

Step 10: As described in Example 1, Step 10, the sulfonamide ester (74 mg, 0.097 mmol) was hydrolyzed to afford the 65 mg (90%) of the title product, a white solid. 1H NMR (400 MHz, $CDCl_3$) δ 1.89-2.05 (m, 2 H), 2.41 (s, 3 H), 2.75 (q, J=7.6 Hz, 4 H), 2.83-2.93 (m, 2 H), 2.92-3.02 (m, 2 H), 4.21-4.31 (m, 3 H), 6.49 (d, J=8.8 Hz, 1 H), 6.72-6.83 (m, 2 H), 6.87 (s, 1 H), 7.01-7.13 (m, 4 H), 7.24-7.35 (m, 9H), 7.41 (d, J=2.0 Hz, 1 H), 8.00 (d, J=8.1 Hz, 2 H). HRMS: calcd for $C_{41}H_{37}Cl_2FN_2O_4S+H+$, 743.19079. found (ESI-FTMS, $[M+H]^{1+}$), 743.1907.

Example 27

4-(3-{5-chloro-1-(diphenylmethyl)-2-[2-({[2-nitro-6-(trifluoromethyl)benzyl]sulfonyl}amino)ethyl]-1H-indol-3-yl}propyl)benzoic acid Step 1: 2-Bromomethyl-1-nitro-3-trifluoromethyl-benzene. To a solution of 2-methyl-1-nitro-3-trifluoromethyl-benzene (5.0 g, 24.4 mmol) in $CCl_4$ (300 mL) was added N-bromosuccinimide (4.35 g, 24.4 mmol) and benzoyl peroxide (0.11 g, 0.45 mmol). The mixture was heated to reflux and exposed to light (300 W) for 20 h. The mixture was cooled to room temperature, filtered and concentrated. Purification by column chromatography (EtOAc-hexanes) afforded 3.03 g (44%) of the benzyl bromide, a yellow oil. $^1H$ NMR (400 MHz, $CDCl_3$) δ 4.93 (s, 2 H), 7.63 (t, J=8.1 Hz, 1 H), 7.94 (d, J=7.8 Hz, 1 H), 8.06 (d, J=8.1 Hz, 1 H).

Step 2: Using the procedure from Example 3, Step 2, the benzyl bromide Step 1 (3.02 g, 10.6 mmol) was reacted with potassium thioacetate to afford 2.71 g (91%) of the benzyl thioacetate as a brown oil. $^1$H NMR (400 MHz, CDCl$_3$) δ 2.34 (s, 3 H), 4.55 (s, 2 H), 7.58 (t, J=7.7 Hz, 1 H), 7.93 (d, J=7.8 Hz, 1 H), 7.98 (d, J=8.1 Hz, 1 H).

Step 3: (2-Nitro-6-trifluoromethylphenyl)methanesulfonyl chloride. Using the procedure from Example 3, Step 3, the benzyl thioacetate (2.71 g, 9.70 mmol) was oxidized to afford 2.42 g (82%) of the title product as a brown oil. $^1$H NMR (400 MHz, CDCl$_3$) δ 5.82 (s, 2 H) broad, 7.84 (t, J=8.1 Hz, 1 H), 8.11 (d, J=7.8 Hz, 1 H), 8.27 (d, J=8.1 Hz, 1 H).

Step 4: Using the procedure in Step 9, Example 1, methyl 4-{3-[2-(2-aminoethyl)-1-benzhydryl-5-chloro-1H-indol-3-yl]propyl}benzoate (Example 7, Step 6, 164 mg, 0.305 mmol) was reacted with (2-Nitro-6-trifluoromethylphenyl)methanesulfonyl chloride from Step 3 to afford 119 mg of the sulfonamide as a yellow solid in 49% yield.

Step 5: As described in Example 1, Step 10, the sulfonamide ester (94 mg, 0.117 mmol) was hydrolyzed to afford the 90 mg (92%) of the title product, a white solid. 1H NMR (400 MHz, CDCl$_3$) δ 1.90-2.04 (m, 2 H), 2.76 (q, J=7.5 Hz, 4 H), 2.80-2.90 (m, 2 H), 2.93-3.01 (m, 2 H), 4.24 (t, J=6.2 Hz, 1 H), 4.87 (s, 2 H) broad, 6.51 (d, J=8.8 Hz, 1 H), 6.81 (dd, J=9.0, 2.1 Hz, 1 H), 6.86 (s, 1 H), 7.08 (dd, J=6.8, 2.5 Hz, 4 H), 7.23-7.36 (m, 9H), 7.42 (d, J=2.0 Hz, 1 H), 7.61 (t, J=8.1 Hz, 1 H), 7.89-8.09 (m, 3 H). HRMS: calcd for C$_{41}$H$_{35}$ClF$_3$N$_3$O$_6$S+H+, 790.19599. found (ESI-FTMS, [M+H]$^{1+}$), 790.1944.

Example 28

4-{3-[5-chloro-1-(diphenylmethyl)-2-(2-{[(2-fluorobenzyl)sulfonyl]amino}ethyl)-1H-indol-3-yl]propyl}benzoic acid Step 1. Using the procedure in Step 9, Example 1, methyl 4-{3-[2-(2-aminoethyl)-1-benzhydryl-5-chloro-1H-indol-3-yl]propyl}benzoate (Example 7, Step 6, 163 mg, 0.303 mmol) was reacted with (2-nitro-6-trifluoromethyl-phenyl)-methanesulfonyl chloride to afford 15 mg of the sulfonamide, a white solid in 7% yield.

Step 2. As described in Example 1, Step 10, the sulfonamide ester (14 mg, 0.020 mmol) was hydrolyzed to afford the 12 mg (88%) of the title product, a white solid. $^1$H NMR (400 MHz, CDCl$_3$) δ 1.88-2.03 (m, 2 H), 2.66-2.78 (m, 4 H), 2.81-2.90 (m, 2 H), 2.90-3.00 (m, 2 H), 4.12-4.20 (m, 3 H), 6.49 (d, J=8.8 Hz, 1 H), 6.80 (dd, J=8.8, 2.3 Hz, 1 H), 6.86 (s, 1 H), 6.94-7.01 (m, 1 H), 7.02-7.12 (m, 5 H), 7.23-7.36 (m, 10 H), 7.40 (d, J=2.0 Hz, 1 H), 8.00 (d, J=8.3 Hz, 2 H). HRMS: calcd for C$_{40}$H$_{36}$ClFN$_2$O$_4$S+H+, 695.21411. found (ESI-FTMS, [M+H]$^{1+}$), 695.2128.

Example 29

4-{3-[2-(2-{[(biphenyl-2-ylmethyl)sulfonyl]amino}ethyl)-5-chloro-1-(diphenylmethyl)-1H-indol-3-yl]propyl}benzoic acid Step 1. The bromide from Example 24, Step 1 (83 mg, 0.108 mmol) was placed in a microwave reaction vessel with phenylboronic acid (19.8 mg, 0.162 mmol), KF (9.4 mg, 0.162 mmol), Pd(OAc)$_2$ (3.4 mg, 0.015 mmol) and PPh$_3$ (11.8 mg, 0.045 mmol). DME (0.12 M), MeOH (0.42 M), H$_2$O (0.42 M) was added to the vessel and the mixture was degassed under a stream of argon, capped, and heated in the Smith Creator microwave at 120° C. for 1 h. The reaction mixture was cooled to room temperature, filtered through celite (washing with EtOAc), and diluted with H$_2$O. The aqueous layer was extracted with EtOAc. The combined organic phase was washed with H$_2$O and brine, dried over MgSO$_4$ and concentrated. Purification of the crude product by column chromatography (EtOAc-Hex.) afforded 75 mg (91%) of the Suzuki product, a yellow solid.

Step 2. As described in Example 1, Step 10, the ester (70 mg, 0.091 mmol) was hydrolyzed to afford 46 mg (67%) of the title compound, a white solid. $^1$H NMR (400 MHz, CDCl$_3$) δ 1.85-1.98 (m, 2 H), 2.45-2.55 (m, 2 H), 2.64-2.78 (m, 4 H), 2.82-2.90 (m, 2 H), 3.99 (t, J=6.3 Hz, 1 H), 4.18 (s, 2 H), 6.47 (d, J=8.8 Hz, 1 H), 6.71-6.84 (m, 2 H), 6.97-7.08 (m, 4 H), 7.15-7.24 (m, 3 H), 7.25-7.28 (m, 4 H), 7.28-7.36 (m, 9H), 7.40 (d, J=2.0 Hz, 1 H), 7.47 (dd, J=7.7, 1.1 Hz, 1 H), 8.01 (d, J=8.3 Hz, 2 H). HRMS: calcd for C$_{46}$H$_{41}$ClN$_2$O$_4$S+H+, 753.25483. found (ESI-FTMS, [M+H]$^{1+}$), 753.253.

Example 30

4-{3-[5-chloro-1-(diphenylmethyl)-2-(2-{[(2-pyridin-4-ylbenzyl)sulfonyl]amino}ethyl)-1H-indol-3-yl]propyl}benzoic acid Step 1. The bromide from Example 24, Step 1 (77 mg, 0.10 mmol) was reacted with pyridine-4-boronic acid according to the procedure in Example 29, Step 1 to afford 33 mg (43%) of the Suzuki product, a white solid.

Step 2. As described in Example 1, Step 10, the ester (33 mg, 0.043 mmol) was hydrolyzed to afford 30 mg (91%) of the title compound, a white solid. $^1$H NMR (400 MHz, CDCl$_3$) δ 1.90-2.01 (m, 2 H), 2.62-2.78 (m, 6 H), 2.90 (t, J=7.5 Hz, 2 H), 4.02 (s, 2 H), 4.56 (s, 1 H) broad, 6.48 (d, J=8.8 Hz, 1 H), 6.79 (dd, J=8.8, 2.0 Hz, 1 H), 6.83 (s, 1 H), 6.99-7.10 (m, 4 H), 7.19 (dd, J=7.6, 1.3 Hz, 1 H), 7.22 (dd, J=4.5, 1.5 Hz, 2 H), 7.24-7.28 (m, 2 H), 7.28-7.34 (m, 7 H), 7.36-7.46 (m, 3 H), 7.98 (d, J=8.3 Hz, 2 H), 8.55 (d, J=5.8 Hz, 2 H). HRMS: calcd for C$_{45}$H$_{40}$ClN$_3$O$_4$S+H+, 754.25008. found (ESI-FTMS, [M+H]$^{1+}$), 754.2505.

Example 31

4-{3-[5-chloro-1-(diphenylmethyl)-2-(2-{[(2-pyridin-3-ylbenzyl)sulfonyl]amino}ethyl)-1H-indol-3-yl]propyl}benzoic acid Step 1. The bromide from Example 24, Step 1 (77 mg, 0.10 mmol) was reacted with pyridine-3-boronic acid according to the procedure in Example 29, Step 1 to afford 59 mg (77%) of the Suzuki product, a yellow solid.

Step 2. As described in Example 1, Step 10, the ester (54 mg, 0.070 mmol) was hydrolyzed to afford 44 mg (83%) of the title compound, a white solid. 1H NMR (400 MHz, CDCl$_3$) δ 1.80-1.93 (m, 2 H), 2.53-2.62 (m, 2 H), 2.67 (t, J=7.5 Hz, 2 H), 2.82 (s, 2 H) broad, 2.95-3.03 (m, 2 H), 4.09 (s, 2 H), 5.61 (dd, J=4.9, 3.4 Hz, 1 H), 6.41 (d, J=8.8 Hz, 1 H), 6.76 (dd, J=9.0, 2.1 Hz, 1 H), 6.89 (s, 1 H), 7.01-7.12 (m, 5 H), 7.22-7.36 (m, 9H), 7.36-7.47 (m, 3 H), 7.55-7.62 (m, 1 H), 7.68-7.74 (m, 1 H), 7.89 (d, J=8.3 Hz, 2 H), 8.60 (dd, J=5.1, 1.5 Hz, 1 H), 8.90 (d, J=2.3 Hz, 1 H). HRMS: calcd for C$_{45}$H$_{40}$ClN$_3$O$_4$S+H+, 754.25008. found (ESI-FTMS, [M+H]$^{1+}$), 754.2505.

Example 32

4-(3-{5-chloro-1-(diphenylmethyl)-2-[2-({[2-(3-thienyl)benzyl]sulfonyl}amino)ethyl]-1H-indol-3-yl}propyl)benzoic acid Step 1. The bromide from Example 24, Step 1 (77 mg, 0.10 mmol) was reacted with thiophene-3-boronic acid according to the procedure in Example 29, Step 1 to afford 67 mg (87%) of the Suzuki product, a yellow solid.

Step 2. As described in Example 1, Step 10, the ester (62 mg, 0.080 mmol) was hydrolyzed to afford 51 mg (83%) of the title compound, a white solid. 1H NMR (400 MHz, CDCl$_3$) δ 1.88-2.00 (m, 2 H), 2.54-2.64 (m, 2 H), 2.68-2.81 (m, 4 H), 2.88-2.99 (m, 2 H), 4.11 (t, J=6.3 Hz, 1 H), 4.20 (s, 2 H), 6.49 (d, J=8.6 Hz, 1 H), 6.80 (dd, J=8.8, 2.0 Hz, 1 H), 6.82 (s, 1 H), 7.00 (dd, J=4.9, 1.4 Hz, 1 H), 7.05 (dd, J=6.7, 2.4 Hz, 4 H), 7.13 (dd, J=3.0, 1.3 Hz, 1 H), 7.20-7.28 (m, 4 H), 7.28-7.34 (m, 8 H), 7.38-7.44 (m, 2 H), 7.97-8.04 (m, 2 H). HRMS: calcd for C$_{44}$H$_{39}$ClN$_2$O$_4$S$_2$+H+, 759.21125. found (ESI-FTMS, [M+H]$^{1+}$), 759.2099

Example 33

4-{3-[5-chloro-2-[2-({[2-(3,5-dimethylisoxazol-4-yl)benzyl]sulfonyl}amino)ethyl]-1-(diphenylmethyl)-1H-indol-3-yl]propyl}benzoic acid Step 1. The bromide from Example 24, Step 1, (77 mg, 0.10 mmol) was reacted with 3,5-dimethylisooxazole-4-boronic acid according to the procedure in Example 29, Step 1 to afford 36 mg (46%) of the Suzuki product, a yellow solid.

Step 2. As described in Example 1, Step 10, the ester (36 mg, 0.046 mmol) was hydrolyzed to afford 32 mg (90%) of the title compound, a white solid. 1H NMR (400 MHz, CDCl$_3$) δ 1.88-2.04 (m, 5 H), 2.14 (s, 3 H), 2.68-2.78 (m, 4 H), 2.78-2.85 (m, 2 H), 2.96 (t, J=7.5 Hz, 2 H), 3.82-3.97 (m, 2 H), 4.18-4.27 (m, 1 H), 6.49 (d, J=8.8 Hz, 1 H), 6.80 (dd, J=8.8, 2.0 Hz, 1 H), 6.83 (d, J=11.4 Hz, 1 H), 7.06 (dd, J=3.7, 1.6 Hz, 4 H), 7.12 (dd, J=7.5, 1.1 Hz, 1 H), 7.26-7.34 (m, 10 H), 7.34-7.40 (m, 1 H), 7.41 (d, J=2.0 Hz, 1 H), 7.99 (d, J=8.3 Hz, 2 H). HRMS: calcd for C$_{45}$H$_{42}$ClN$_3$O$_5$S+H+, 772.26065. found (ESI-FTMS, [M+H]$^{1+}$), 772.2595.

Example 34

4-{3-[5-chloro-1-(diphenylmethyl)-2-(2-{[(2-quinolin-8-ylbenzyl)sulfonyl]amino}ethyl)-1H-indol-3-yl]propyl}benzoic acid Step 1. The bromide from Example 24, Step 1, (77 mg, 0.10 mmol) was reacted with 8-quinolineboronic acid according to the procedure in Example 29, Step 1 to afford 67 mg (82%) of the Suzuki product, a white solid.

Step 2. As described in Example 1, Step 10, the ester (60 mg, 0.073 mmol) was hydrolyzed to afford 42 mg (72%) of the title compound, a yellow solid. 1H NMR (400 MHz, CDCl$_3$) δ 1.68-1.85 (m, 1 H), 1.99-2.13 (m, 1 H), 2.23-2.37 (m, 1 H), 2.43-2.53 (m, 3 H), 2.56-2.85 (m, 4 H), 3.91 (d, J=14.1 Hz, 1 H), 4.28 (d, J=14.1 Hz, 1 H), 4.83 (t, J=4.7 Hz, 1 H), 6.39 (d, J=8.8 Hz, 1 H), 6.72-6.80 (m, 2 H), 6.94-7.01 (m, 2 H), 7.01-7.09 (m, 2 H), 7.19-7.27 (m, 4 H), 7.27-7.31 (m, 4 H), 7.32-7.37 (m, 1 H), 7.37-7.44 (m, 4 H), 7.47-7.56 (m, 3 H), 7.75-7.91 (m, 3 H), 8.22 (dd, J=8.3, 1.8 Hz, 1 H), 8.94 (dd, J=4.3, 1.8 Hz, 1 H). HRMS: calcd for C$_{49}$H$_{42}$ClN$_3$O$_4$S+H+, 804.26573. found (ESI-FTMS, [M+H]$^{1+}$), 804.2641.

Example 35

4-{3-[5-chloro-2-{2-[({[4'-(dimethylamino)biphenyl-2-yl]methyl}sulfonyl)amino]ethyl}-1-(diphenylmethyl)-1H-indol-3-yl]propyl}benzoic acid Step 1. The bromide from Example 24, Step 1 (77 mg, 0.10 mmol) was reacted with 4-(dimethylamino)-phenylboronic acid according to the procedure in Example 29, Step 1 to afford 51 mg (ca. 52%) of the Suzuki product, a white solid.

Step 2. As described in Example 1, Step 10, the ester (51 mg, 0.063 mmol) was hydrolyzed to afford 17 mg (ca. 41%) of the title compound, a white solid. 1H NMR (400 MHz, CDCl$_3$) δ 1.87-1.98 (m, 2 H), 2.44-2.53 (m, 2 H), 2.64-2.70 (m, 2 H), 2.70-2.77 (m, 2 H), 2.79-2.89 (m, 8 H), 4.01-4.07 (m, 1 H), 4.28 (s, 2 H), 6.46 (d, J=8.8 Hz, 1 H), 6.59 (d, J=8.8 Hz, 2 H), 6.76-6.81 (m, 2 H), 6.99-7.07 (m, 6 H), 7.16-7.23 (m, 2 H), 7.25-7.33 (m, 9H), 7.39 (d, J=2.3 Hz, 1 H), 7.44-7.49 (m, 1 H), 8.00 (d, J=8.3 Hz, 2 H). HRMS: calcd for (C$_{48}$H$_{46}$ClN$_3$O$_4$S+2 H+)/2, 398.65215. found (ESI-FTMS, [M+2 H]$^{2+}$), 398.6504

Example 36

4-[3-(5-chloro-1-(diphenylmethyl)-2-{2-[({[2'-(trifluoromethoxy)biphenyl-2-yl]methyl}sulfonyl)amino]ethyl}-1H-indol-3-yl)propyl]benzoic acid Step 1. The bromide from Example 24, Step 1 (77 mg, 0.10 mmol) was reacted with 2-(trifluoromethoxy)phenylboronic acid according to the procedure in Example 29, Step 1 to afford 36 mg (ca. 36%) of the Suzuki product, a white solid.

Step 2. As described in Example 1, Step 10, the ester (36 mg, 0.042 mmol) was hydrolyzed to afford 23 mg (ca. 75%) of the title compound, a white solid. 1H NMR (400 MHz, CDCl$_3$) δ 1.80-1.91 (m, 2 H), 2.54 (q, J=7.2 Hz, 2 H), 2.59-2.70 (m, 4 H), 2.78-2.87 (m, 2 H), 3.90 (q, J=14.1 Hz, 2 H), 4.05-4.11 (m, 1 H), 6.40 (d, J=8.8 Hz, 1 H), 6.67-6.76 (m, 2 H), 6.92-7.02 (m, 4 H), 7.07-7.16 (m, 3 H), 7.16-7.30 (m, 12H), 7.31-7.36 (m, 2 H), 7.93 (d, J=8.3 Hz, 2 H). HRMS: calcd for C$_{47}$H$_{40}$ClF$_3$N$_2$O$_5$S+H+, 837.23713. found (ESI-FTMS, [M+H]$^{1+}$), 837.2375.

Example 37

4-{3-[5-chloro-2-[2-({[(2'-cyanobiphenyl-2-yl)methyl]sulfonyl}amino)ethyl]-1-(diphenylmethyl)-1H-indol-3-yl]propyl}benzoic acid Step 1. The bromide from Example 24, Step 1 (73 mg, 0.095 mmol) was reacted with 2-cyanophenylboronic acid to afford 23 mg (30%) of the Suzuki product, a yellow solid.

Step 2. As described in Example 1, Step 10, the ester (19 mg, 0.024 mmol) was hydrolyzed to afford 10 mg (53%) of the title compound, a white solid. $^1$H NMR (400 MHz, CDCl$_3$) δ 1.87-2.01 (m, 2 H), 2.62-2.79 (m, 6 H), 2.92 (t, J=7.6 Hz, 2 H), 3.91-4.14 (m, 3 H), 6.47 (d, J=8.8 Hz, 1 H), 6.75-6.85 (m, 2 H), 7.01-7.08 (m, 4 H), 7.22-7.28 (m, 3 H), 7.28-7.36 (m, 8 H), 7.36-7.44 (m, 4 H), 7.49-7.59 (m, 1 H), 7.63-7.69 (m, 1 H), 8.00 (d, J=8.3 Hz, 2 H). HRMS: calcd for C$_{47}$H$_{40}$ClN$_3$O$_4$S+H+, 778.25008. found (ESI-FTMS, [M+H]$^{1+}$), 778.2489.

Example 38

3-{4-[(2-{5-chloro-1-(diphenylmethyl)-2-[2-({[2-(trifluoromethyl)benzyl]sulfonyl}amino)ethyl]-1H-indol-3-yl}ethyl)sulfonyl]phenyl}propanoic acid Step 1: 2-Bromo-4-chloroaniline (1.0 eq) was dissolved in $CH_2Cl_2$ (0.25 M), then triethylamine and trifluoroacetyl anhydride (1.1 eq each) were added. The resulting mixture was stirred at room temperature for 1 hour. The solvent was evaporated and the residue was purified by flash chromatography with $CH_2Cl_2$ as eluent to give the amide in 97% yield. m/z (M−H)⁻ 300.0.

Step 2: N-(2-Bromo-4-chlorophenyl)-2,2,2-trifluoroacetamide (Step 1, 1.0 eq) was mixed with 3-butyn-1-ol (2.0 eq), dichlorobis(triphenylphosphine)palladium(II) (2.5% eq), triethylamine (3.0 eq), CuI (5% eq) in DMF (0.2 M) in a sealed vessel under $N_2$ and heated to 120° C. for 4 hours. The reaction mixture was then diluted with ethyl acetate, washed with brine and dried over $Na_2SO_4$. Purification by flash column chromatography with 2% MeOH/$CH_2Cl_2$ afforded the alkyne in 67% yield. m/z (M−H)⁻ 194.09

Step 3: 2-(5-Chloro-1H-indol-2-yl)ethanol (step 2, 1.0 eq) and imidazole (2.0 eq) were dissolved in DMF (0.3 M) at room temperature with stirring before tert-butylchlorodiphenylsilane (1.2 eq) was added. The resulting mixture was stirred overnight at room temperature before it was quenched with a saturated aqueous sodium bicarbonate solution and extracted with ethyl acetate. The organic phase was washed with water and brine and dried over $Na_2SO_4$. Purification by flash chromatography with $CH_2Cl_2$ as eluent afforded the silyl ether as a brown gum in over 90% yield. m/z (M−H)⁻ 433.0

Step 4: 2-({[tert-Butyl(diphenyl)silyl]oxy}ethyl)-5-chloro-1H-indole (Step 3, 1.0 eq) was dissolved in ether (0.4 M) and the solution was cooled to 0° C. Oxalyl chloride (1.2 eq) was added to the above cold solution with vigorous stirring. The reaction mixture was stirred at 0° C. for 1 hour before EtOH was added, followed by $NEt_3$. The resulting mixture was then diluted with more EtOH before it was poured into water and extracted with EtOAc. The organic phase washed with brine, dried over $Na_2SO_4$, and concentrated to give the ketoester as yellow solid in 70% yield. m/z (M−H)⁻ 533.0

Step 5: Ethyl [2-({[tert-butyl(diphenyl)silyl]oxy}ethyl)-5-chloro-1H-indol-3-yl](oxo)acetate (Step 4, 1 eq), $Ph_2CHBr$ (1.5 eq) and $Cs_2CO_3$ (1.5 eq) were mixed in dry acetonitrile (0.1M). The mixture was heated to reflux for 2 hours. The reaction mixture was cooled to room temperature, diluted with water and extracted with EtOAc. The organic phase was concentrated and the residue was chromatographed with $CH_2Cl_2$ as eluent to give the N-benzhydryl indole as an orange gum in 45% yield. m/z (M+H)⁺ 701.3

Step 6: To a solution of ethyl [1-benzhydryl-2-({[tert-butyl(diphenyl)silyl]oxy}ethyl)-5-chloro-1H-indol-3-yl](oxo)acetate (Step 5, 1 eq) in THF (0.1M) was added $BH_3Me_2S$ (2M in THF) (2 eq). The resulting mixture was heated to reflux overnight under $N_2$. The reaction mixture was cooled to room temperature, then quenched slowly with 1N NaOH, extracted with EtOAc, and washed with brine. Concentration afforded the alcohol in 65% yield. m/z (M+H)⁺ 645.0

Step 7: To a solution of 2-[1-benzhydryl-2-({[tert-butyl(diphenyl)silyl]oxy}ethyl)-5-chloro-1H-indol-3-yl]ethanol (Step 6, 1 eq) in $CH_2Cl_2$ (0.08M) was added 1,3-bis(diphenylphosphino)-propane (DPPP, 0.75 eq). The solution was cooled to 0° C. under $N_2$, then $CBr_4$ (1.25 eq) was added. The reaction temperature was allowed to return to room temperature over 2 h. The solvent was evaporated, and the residue was purified using a short silica gel column with $CH_2Cl_2$ as eluent to give the bromide in quantitative yield. m/z (M+H)⁺ 708.0

Step 8: 1-Benzhydryl-3-(2-bromoethyl)-2-({[tert-butyl(diphenyl)silyl]oxy}ethyl)-5-chloro-1H-indole (Step 7, 1 eq) was mixed with methyl-3-(4-mercaptolphenyl)propionate (1.5 eq) and $K_2CO_3$ (1.5 eq) in DMF (0.1 M). The resulting mixture was stirred at room temperature under $N_2$ for 2 h, then diluted with water and extracted with EtOAc. The organic extract was washed with brine, concentrated, and purified by flash chromatography ($CH_2Cl_2$ as eluent) to give the thioether as a brownish gum in 80% yield. m/z (M+H) 823.0

Step 9: Methyl 3-[4-({2-[1-benzhydryl-2-({[tert-butyl(diphenyl)silyl]oxy}ethyl)-5-chloro-1H-indol-3-yl]ethyl}sulfanyl)phenyl]propanoate (Step 8, 1 eq) was dissolved in acetonitrile (0.1 M), then molecular sieves (powder, 4 A,) and 4-methylmorpholine N-oxide (NMO) (4 eq) were added under $N_2$. After 5 min, n-$Pr_4NRuO_4$ (TPAP) (5% eq) was added. The resulting mixture was heated at 40° C. for 1.5 h. The mixture was concentrated and the residue was purified by flash chromatography with $CH_2Cl_2$, then 1% EtOAc/$CH_2Cl_2$ as eluent to give the sulfone as a white foam in 44% yield. m/z (M+H)⁺ 855.1

Step 10: Methyl 3-(4-{2-[1-benzhydryl-2-({[tert-butyl(diphenyl)silyl]oxy}ethyl)-5-chloro-1H-indol-3-yl]ethoxy}phenyl)propanoate (Step 9, 1 eq) was dissolved in THF (0.1 M) and cooled to 0° C. then treated with $nBu_4NF$ (1 M in THF) (1.2 eq). The resulting mixture was stirred at 0° C. for 5 min, then warmed to room temperature and stirred for 30 min. The solvent was evaporated and the residue was purified by flash chromatography with EtOAc/$CH_2Cl_2$ (1:9 to 1:4) as eluent to give the alcohol as a white foam in 90% yield. m/z (M+H)⁺ 616.20

Step 11: Methyl 3-[4-{2-[1-benzhydryl-5-chloro-2-(hydroxyethyl)-1H-indol-3-yl]ethyl}-sulfonyl)phenyl]propanoate (Step 10, 1 eq) in $CH_2Cl_2$ (0.02 M) was treated at 0° C. with $MeSO_2Cl$ (2.0 eq) and $Et_3N$ (2.5 eq) and stirred for 1 hour. The ice-bath was removed and the reaction mixture was stirred for 1 hour at room temperature before it was diluted with $CH_2Cl_2$, washed with $NaH_2PO_4$, brine and dried over $Na_2SO_4$. Evaporation of the solvent afforded the mesylate in quantitative yield. m/z (M+H)⁺ 695.0

Step 12: Methyl 3-(4-{[2-(1-benzhydryl-5-chloro-2-{2-[(methylsulfonyl)oxy]ethyl}-1H-indol-3-yl)ethyl]sulfonyl}phenyl)propanoate (Step 11, 1.0 eq) was dissolved in DMF (0.03 M) and treated with $NaN_3$ (3.0 eq). The resulting mixture was heated to 60° C. and stirred for 2 hours, then cooled to room temperature, diluted with water, extracted with ethyl acetate, washed with brine and dried with $Na_2SO_4$. Evaporation of solvent afforded the azide in quantitative yield. m/z (M+H)⁺ 641.1

Step 13: Methyl 3-[4-({2-[2-(2-azidoethyl)-1-benzhydryl-5-chloro-1H-indol-3-yl]ethyl}sulfonyl)phenyl]propanoate (Step 12, 1 eq) was dissolved in THF (0.1 M), and treated with triphenylphosphine (1.1 eq). After 2 days water was added, and the mixture was stirred overnight, concentrated, and purified by flash chromatography using 4% MeOH:$CH_2Cl_2$ as eluent to give the amine in 71% yield. m/z (M+H)⁺ 615.2

Step 14: As outlined in Step 9, Example 1, ethyl 3-[4-({2-[2-(2-aminoethyl)-1-benzhydryl-5-chloro-1H-indol-3-yl]ethyl}sulfonyl)phenyl]propanoate (Step 13, 200 mg, 0.32 mmol) was reacted with (2-trifluoromethylphenyl)methanesulfonyl chloride (Example 5, Step 3, 110 mg, 0.42 mmol) to afford 250 mg of the sulfonamide, a pale yellow foam, in 93% yield. ¹HNMR (400 MHz, $CDCl_3$) δ 1.23 (t, J=7.2 Hz, 3 H), 2.62-2.71 (m, 2 H), 2.76-2.93 (m, 4 H), 2.98-3.17 (m, 4 H), 3.27-3.38 (m, 2 H), 4.11 (q, J=7.2 Hz, 2 H), 4.35 (s, 2 H), 4.57

(t, J=5.3 Hz, 1 H), 6.43 (d, J=9.1 Hz, 1 H), 6.77 (dd, J=8.8, 2.0 Hz, 1 H), 6.81 (s, 1 H), 7.18 (d, J=2.0 Hz, 1 H), 7.24-7.35 (m, 10 H), 7.41 (d, J=8.6 Hz, 3 H), 7.49 (t, J=8.3 Hz, 1 H), 7.60-7.77 (m, 2 H), 7.88 (d, J=8.6 Hz, 2 H).

Step 15: Using the procedure in Step 10 Example 1, the sulfonamide ester (220 mg, 0.26 mmol) was hydrolyzed to afford 200 mg (92%) of the title product, a white foam. $^1$H NMR (400 MHz, DMSO-$d_6$) δ 2.65 (t, J=7.6 Hz, 2 H), 2.91-3.13 (m, 8 H), 3.60 (dd, J=9.7, 5.4 Hz, 2 H), 4.46 (s, 2 H), 6.48 (d, J=8.8 Hz, 1 H), 6.83 (dd, J=8.7, 2.1 Hz, 1 H), 7.05-7.16 (m, 5 H), 7.19 (d, J=2.3 Hz, 1 H), 7.33-7.47 (m, 6 H), 7.53-7.72 (m, 6 H), 7.80 (d, J=7.6 Hz, 1 H), 7.94 (d, J=8.3 Hz, 2 H), 12.26 (s, 1 H); HRMS: calcd for $C_{42}H_{38}ClF_3N_2O_6S_2$+H+, 823.18847. found (ESI-FTMS, [M+H]$^{1+}$), 823.1887; HPLC purity H$_2$O/CH$_3$CN: 100%, H$_2$O/MeOH: 100%.

Example 39

3-(4-{[2-(5-chloro-1-(diphenylmethyl)-2-{2-[({1-[2-(trifluoromethyl)phenyl]ethyl}sulfonyl)amino]ethyl}-1H-indol-3-yl)ethyl]sulfonyl}phenyl)propanoic acid Step 1: Using the procedure in Example 1, Step 9, ethyl 3-[4-({2-[2-(2-aminoethyl)-5-chloro-1-(diphenylmethyl)-1H-indol-3-yl]ethyl}sulfonyl)phenyl]propanoate (Example 38, Step 14) was reacted with 1-(2-trifluoromethyl-phenyl)-ethanesulfonyl chloride (0.13 g, 0.46 mmol) to afford 3-{4-[2-(1-benzhydryl-5-chloro-2-{2-[1-(2-trifluoromethyl-phenyl)-ethanesulfonylamino]-ethyl}-1H-indol-3-yl)-ethanesulfonyl]-phenyl}-propionic acid ethyl ester (0.110 g, 40%).

Step 2: The sulfonamide ester (0.11 g, 0.13 mmol) was hydrolyzed according to Example 1, Step 10 to afford 0.068 g (64%) of the title product, a white solid.

1H NMR (400 MHz, CDCl$_3$) δ 1.67 (d, J=6.8 Hz, 3 H) 2.57-2.72 (m, 4 H) 2.80 (t, J=6.8 Hz, 2 H) 2.84-2.94 (m, 2 H) 3.03 (t, J=6.4 Hz, 2 H) 3.20-3.31 (m, 2 H) 5.82-5.88 (m, 1 H) 6.37 (s, 1 H) 6.73-6.81 (m, 2 H) 6.98 (d, J=4.4 Hz, 2 H) 7.05 (d, J=5.4 Hz, 2 H) 7.24-7.49 (m, 11 H) 7.63 (d, J=7.8 Hz, 1 H) 7.80 (d, J=7.8 Hz, 1 H) 7.88 (d, J=8.6 Hz, 2 H).

Example 40

4-{3-[5-chloro-1-(diphenylmethyl)-2-(2-{[(2-hydroxybenzyl)sulfonyl]amino}ethyl)-1H-indol-3-yl]propyl}benzoic acid Step 1: Using the procedure described in Example 5, Step 1, 2-benzyloxybenzylbromide (ref. *J. Med. Chem.* 2006, 49, 31-34, R. V. Somu et al.) (32.2 g, 116 mmol) afforded (2-benzyloxy-phenyl)-methanesulfonic acid sodium salt (30 g, 86%), a white solid. $^1$H NMR (400 MHz, DMSO-$d_6$) δ 3.82 (s, 2 H) 5.09 (s, 2 H) 6.81-6.91 (m, 1 H) 6.96 (d, J=7.58 Hz, 1 H) 7.08-7.18 (m, 1 H) 7.26-7.34 (m, 1 H) 7.34-7.41 (m, 2 H) 7.45 (dd, J=1.77 Hz, 1 H) 7.52 (d, J=7.07 Hz, 2 H).

Step 2: Using the procedure described in Example 5, Step 2, (2-benzyloxy-phenyl)-methanesulfonic acid sodium salt (30 g, 99 mmol) afforded (2-benzyloxy-phenyl)-methanesulfonic acid (15 g), a white solid which was used without further purification. $^1$H NMR (400 MHz, DMSO-$d_6$) δ 3.81 (s, 2 H) 5.08 (s, 2 H) 6.80-6.92 (m, 1 H) 6.95 (d, J=7.83 Hz, 1 H) 7.07-7.17 (m, 1 H) 7.31 (d, J=6.82 Hz, 1 H) 7.34-7.42 (m, 2 H) 7.45 (dd, 1 H) 7.52 (d, J=7.33 Hz, 2 H).

Step 3: Using the procedure described in Example 5, Step 3, (2-benzyloxy-phenyl)-methanesulfonic acid (7 g, 25.15 mmol) afforded (2-benzyloxy-phenyl)-methanesulfonyl chloride (2.6 g, 35%). $^1$H NMR (400 MHz, CDCl$_3$) δ 5.06 (s, 2 H) 5.15 (s, 2 H) 7.00-7.10 (m, 2 H) 7.30-7.50 (m, 7 H).

Step 4: As outlined in Step 9 Example 1, methyl 4-{3-[2-(2-aminoethyl)-1-benzhydryl-5-chloro-1H-indol-3-yl]propyl}benzoate (Example 7, Step 6, 3.92 g, 7.3 mmol) was reacted with (2-benzyloxy-phenyl)-methanesulfonyl chloride (2.6 g, 8.76 mmol) to afford 4.1 g of methyl 4-{3-[2-[2-({[2-(benzyloxy)benzyl]sulfonyl}amino)ethyl]-5-chloro-1-(diphenylmethyl)-1H-indol-3-yl]propyl}benzoate, a white foam, in 59% yield. $^1$H NMR (400 MHz, CDCl$_3$) δ 1.80-1.99 (m, 2 H) 2.49-2.78 (m, 6 H) 2.85 (t, J=8.84 Hz, 2 H) 3.89 (s, 3 H) 3.96-4.05 (m, 1 H) 4.26 (s, 2 H) 4.90 (s, 2 H) 6.45 (d, J=8.84 Hz, 1 H) 6.73-6.82 (m, 2 H) 6.83-6.93 (m, 2 H) 6.94-7.08 (m, 4 H) 7.16-7.34 (m, 15 H) 7.39 (d, J=2.02 Hz, 1 H) 7.85-7.98 (m, 2 H).

Step 5: Methyl 4-{3-[2-[2-({[2-(benzyloxy)benzyl]sulfonyl}amino)ethyl]-5-chloro-1-(diphenylmethyl)-1H-indol-3-yl]propyl}benzoate (5.1 g, 6.4 mmol) was reacted with hydrogen in the presence of palladium on carbon (0.5 g) to afford a mixture of methyl 4-{3-[5-chloro-1-(diphenylmethyl)-2-(2-{[(2-hydroxybenzyl)sulfonyl]amino}ethyl)-1H-indol-3-yl]propyl}benzoate and methyl 4-{3-[1-(diphenylmethyl)-2-(2-{[(2-hydroxybenzyl)sulfonyl]amino}ethyl)-1H-indol-3-yl]propyl}benzoate (3:1) as a white foam in 74% overall yield.

Step 6: Using the procedure in Step 10, Example 1, the sulfonamide ester mixture (3.35 g) was hydrolyzed and purified by preparative HPLC to afford 1.18 g (36%) of the title product, a white solid. $^1$H NMR (400 MHz, CDCl$_3$) δ 1.89-2.01 (m, 2 H) 2.64-2.96 (m, 8 H) 4.16 (s, 2 H) 4.17-4.25 (m, 1 H) 6.50 (d, J=8.84 Hz, 1 H) 6.74-6.89 (m, 4 H) 6.95 (dd, J=1.64 Hz, 1 H) 7.01-7.13 (m, 4 H) 7.11-7.23 (m, 1 H) 7.23-7.38 (m, 8 H) 7.41 (d, J=2.02 Hz, 1 H) 7.90-8.04 (m, 2 H); HRMS: calcd for $C_{40}H_{37}ClN_2O_5S$+H+, 693.21845. found (ESI-FTMS, [M+H]$^{1+}$), 693.21709; HPLC purity (CH$_3$CN—H$_2$O): 7.24 min, 100.0%. HPLC purity (MeOH—H$_2$O): 8.12 min, 100.0%.

Example 41

4-{3-[5-chloro-1-(diphenylmethyl)-2-(2-{[(2-quinolin-5-ylbenzyl)sulfonyl]amino}ethyl)-1H-indol-3-yl]propyl}benzoic acid Step 1. The bromide from Example 24, Step 1 was reacted with 5-quinolineboronic acid according to the procedure in Example 29, Step 1 to afford the Suzuki product.

Step 2. As described in Example 1, Step 10, the ester was hydrolyzed and the product purified by preparative HPLC to afford the title compound, a white solid. $^1$H NMR (400 MHz, CDCl$_3$) δ $^1$H NMR (400 MHz, CDCl$_3$) δ 1.77-1.91 (m, 2 H), 2.35-2.70 (m, 6 H), 2.76 (t, J=7.2 Hz, 2 H), 3.65 (d, J=13.9 Hz, 1 H), 3.89 (d, J=13.9 Hz, 1 H), 4.00 (t, J=5.3 Hz, 1 H), 6.39 (d, J=9.1 Hz, 1 H), 6.63-6.79 (m, 2 H), 6.86-7.04 (m, 4 H), 7.08-7.24 (m, 10 H), 7.24-7.40 (m, 4 H), 7.43-7.51 (m, 1 H), 7.55 (dd, J=8.6, 7.1 Hz, 1 H), 7.62 (d, J=8.3 Hz, 1 H), 7.84-7.94 (m, 2 H), 8.05 (d, J=8.6 Hz, 1 H), 8.83 (dd, J=4.3, 1.8 Hz, 1 H). HRMS: calcd for $C_{49}H_{42}ClN_3O_4S$+H+, 804.26573. found (ESI-FTMS, [M+H]$^{1+}$), 804.2663.

An alternative method for preparing intermediate compounds of the general formula:

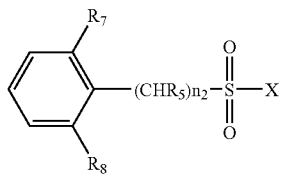

where X is halogen, preferably chlorine, is disclosed in U.S. patent application Ser. No. 11/064,241, filed Feb. 23, 2005, which is incorporated by reference herein in its entirety. Briefly, the method involves the formation of sulfonic acid prior to conversion to the sulfonyl halide, according to the general scheme below:

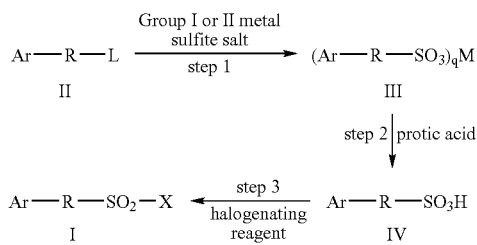

wherein L is a leaving group; Ar represents a 2,6-disubstituted phenyl moiety; R represents a $(CHR_5)_{n2}$ moiety, and M is a group I or group II metal ion. In accordance with the scheme, sulfonic acids of Formula IV can be converted to sulfonyl halides by reaction with a halogen substitution reagent (i.e., a reagent that can convert a non-halogen substituent such as, for example, H or OH, to a halogen substituent; i.e., convert a sulfonic acid moiety to a sulfonyl halide moiety), for example $SOCl_2$, $POCl_3$, $CCl_4$/triphenylphosphine, oxalyl chloride or oxalyl bromide, preferably oxalyl chloride. The halogen substitution agent is preferably used in excess quantity, particularly if there is residual solvent in either the starting material, solvents or both. When oxalyl chloride is used as the halogen substitution agent, it can be used in a range from about 1 to about 6 equivalents; about 2 to about 4 equivalents or about 3 to about 3.5 equivalents with respect to the amount of sulfonic acid reagent (compound of Formula IV). One skilled in the art will recognize that the amount of halogen substitution agent used will depend, inter alia, on the amount of water in the starting material or solvent and the nature and reactivity of the starting material and solvents.

Suitable solvents for the halogen substitution reaction (step 3 of the scheme above) include any organic solvent that can at least partially dissolve the compound of Formula IV. Preferred solvents include non-polar or weakly polar solvents, including acetonitrile, aromatic hydrocarbons such as benzene and toluene, and halogenated solvents such as 1,2-dichloroethane and methylene chloride. More preferred solvents are ethers. Suitable ethers include tetrahydrofuran, dioxane, diethyl ether, dibutyl ether, diisopropyl ether or mixtures thereof and the like. A more preferred ether is tetrahydrofuran.

The halogen substitution reaction can be carried out at any suitable temperature, for example at about −40° C. to about room temperature, preferably below about −10° C.

The sulfonyl halide-forming step (step 3 of the scheme above) can also be carried out in the presence of an acyl transfer catalyst, such as a tertiary amide (e.g., dimethylformamide). The acyl transfer catalyst can be provided in an amount sufficient to accelerate the reaction rate. The acyl transfer catalyst is present in less than about one equivalent relative to the amount of sulfonic acid reagent, preferably in an amount of about 0.01 to about 0.5 equivalents; even more preferred, about 0.1 to about 0.2 equivalents, relative to the amount of sulfonic acid reagent.

The compounds of Formula I can be isolated from the reaction mixture by precipitation and filtration. Any of numerous well known methods for inducing precipitation can be used. In some preferred embodiments, an anti-solvent such as water or a solvent containing water can be added to the reaction mixture to induce precipitation. Use of water as an anti-solvent can reduce decomposition rate of the sulfonyl halide product relative to the decomposition rate observed when an organic solvent such as heptane is used, resulting in improved yields. Precipitation can be facilitated by lowering the temperature of the reaction mixture to, for example, to below about −20° C.

As shown in the scheme above, sulfonic acids of Formula IV can be prepared by reacting sulfonic acid salts (sulfonate salts) of Formula III with a protic acid. Suitable protic acids are of sufficient strength so as to be capable of converting a sulfonate salt to its corresponding acid according to the processes of the invention. For example, the protic acid can be a strong inorganic acid such as HCl, HBr, $H_3PO_4$, $HNO_3$, $HClO_4$, $H_2SO_4$, and the like. Alternatively, the protic acid can be an organic acid, such as formic, methanesulfonic acid, p-toluene sulfonic acid, benzenesulfonic acid, trifluoroacetic acid and other strong organic acids. The protic acid can be provided in gaseous form. Preferably, the inorganic acid is HCl, more preferably gaseous HCl that is added to the reaction solvent containing the sulfonate salt. The protic acid is advantageously provided in excess molar equivalents relative to the sulfonic acid salt of Formula III.

Formation of the sulfonic acid compound of Formula IV can be carried out in any suitable solvent. For example, organic solvents in which the compound of Formula III is at least partially soluble are suitable. The solvent can be chosen such that it poorly dissolves metal halide salts, such as NaCl or KCl, thereby thermodynamically driving the reaction by precipitation of metal halide salt. The solvent can contain an alcohol, such as methanol, ethanol, isopropanol, and the like, or a mixture thereof, preferably methanol. The solvent can also contain water. Reaction temperature can be readily determined by the skilled artisan. For example, the reaction can be carried out at a temperature below room temperature, such as about −20 to about 10° C., preferably at about 0 or below about 10° C.

The sulfonic acid compound of Formula IV can be isolated according to routine methods, such as precipitating the product from the reaction mixture.

The sulfonic acid salt (sulfonate salt) compound of Formula III can be prepared by reacting a compound of Formula II: Ar—R-L (wherein Ar, R and L are defined hereinabove) with a Group I or II metal sulfite salt optionally in the presence of a phase transfer catalyst as shown in step 1 of the scheme above. Any Group I or II metal sulfite salt is suitable, for example, $Li_2SO_3$, $Na_2SO_3$, $K_2SO_3$, $MgSO_3$, $CaSO_3$, and the like. Group I or II metal sulfite salts can be provided in molar excess of, for example, about 2 eq, to about 1 eq, relative to the amount of compound of Formula II. Suitable metal salts include $Na_2SO_3$, $K_2SO_3$ and $Na_2SO_3$.

The formation of the sulfonate salt compounds of Formula III can be carried out in the presence of a phase transfer catalyst, for example a quaternary ammonium halide, such as tetrabutyl ammonium iodide. The phase transfer catalyst can be provided in an amount suitable to accelerate the reaction rate, for example in about 0.1 to 2% or more preferably 0.5 to 1% by weight.

Any suitable solvent can be employed, such as solvent that can at least partially dissolve Group I or II metal sulfite salts, such as water, in an amount of from about 50%, more preferably about 75%, even more preferably more than about 90%, still more preferably more than about 95%, and yet more preferably more than about 99% water. The reaction can also be carried out at any suitable temperature, preferably an elevated temperature, for example about 100° C.

Isolation of the compound of Formula III from the reaction mixture can be carried out by any routine method, such as precipitation from the reaction mixture by, for example, treatment of the reaction mixture with a water-soluble inorganic salt such as NaCl or KCl, more preferably NaCl. Isolation of the compound of Formula III can be further facilitated by the addition to the reaction mixture of an organic solvent that is not substantially miscible with water, such as ethyl acetate, ethers (e.g. ethyl ether and the like), alkanes (e.g., hexanes, petroleum ether, etc.), aromatics (e.g., benzene, toluene, xylene, etc.), and the like, with ethyl acetate being most preferred. The reaction mixture can also be cooled (e.g., less than about 10° C.) to help induce precipitation.

Biological Test Procedures

GLU Micelle Assay

The assay was carried in a 96-well format using a fluorescent plate reader with a 355 nM excitation filter and a 460 nM emission filter (Lab Systems Fluoroscan II, Helsinki, Finland). The assay buffer contained 940 μM Triton X-100, 50 mM Hepes pH 7.4, 0.3 mM EDTA, 1 mM $CaCl_2$ and 300 mM KCl. DTPC (1,2-O-tetradecyl-sn-glycero-3-phosphocholine, Avanti) at a final concentration of 120 μM was added the day of the experiment and GLU (7-Hydroxycoumarinyl-γ-linolenate, Biomol Research Lab, Inc.) at a final concentration of 90 μM was added immediately prior to each assay.

Compounds (10 μL) dissolved in DMSO were placed in duplicate wells of a black 96-well plate. Wells corresponding to the positive and negative controls contained DMSO without inhibitors. Just prior to the experiment, 200 μL assay buffer containing 90 μM GLU and 120 μM DTPC was added to all wells in the assay plate. Assay buffer (50 μL) was added to the negative, and 50 μL $cPLA_2\alpha$ solution (5 mg/mL in assay buffer) was added to all other wells to initiate the reaction. The final concentration of enzyme was 1 μg/ml. The content of each well was mixed gently during the addition of the enzyme, and the plate was rapidly transferred to the fluorescent plate reader. The increase in fluorescence was read every 4 min for 84 min. The slope of the resulting line was determined and the inhibition was calculated using the equation below:

Percent Inhibition=[1−(slope with inhibitor−slope negative control)/(slope positive control−slope negative control)]×100

Rat Whole Blood Assay

Fresh blood was collected in heparinized tubes by cardiac puncture of male Sprague-Dawley rats. Aliquots of blood (0.6 mL) were incubated with either 6 μL solvent (DMSO), or 6 μL of test compounds at various concentrations for 15 minutes at 37° C. This was followed by incubation of the blood with 6 μL of calcium ionophore, A23187 (Sigma C-7522) diluted in DMSO for 10 min at 37° C. The final concentration of A23187 was 5 μM. DMSO (6 μL) was added in the unstimulated controls. The reactions were stopped by mixing 60 μL cold EDTA to give a final concentration of 20 mM. The blood was centrifuged at 6,500 rpm for 10 min on a microcentrifuge to obtain plasma. A 70 μL aliquot of plasma was mixed with 400 μL cold methanol for protein precipitation. After incubation at −80° C. for 30 min, the supernatant was obtained by centrifuging at 6,500 rpm for 10 min, and was assayed for $TXB_2$ according to the manufacturer's procedure (Assay Designs, Inc.'s ELISA kit #900-002).

Results of the GLU Micelle Assay and the Rat Whole Blood Assay for compounds of the invention is shown in Table 1, below:

| Example # | GLU Micelle $IC_{50}$ (uM) | Rat Whole Blood $TXB_2$ $IC_{50}$ (uM) |
| --- | --- | --- |
| 1 | 0.26 | 0.14 |
| 2 | 0.19 | 0.12 |
| 3 | 0.054 | 0.06 |
| 4 | 0.054 | 0.02 |
| 5 | 0.026 | 0.02 |
| 6 | 0.092 | 0.08 |
| 7 | 0.018 | 0.03 |
| 8 | 0.024 | 0.02 |
| 9 | 0.022 | 0.02 |
| 10 | 0.009 | 0.02 |
| 11 | 0.28 | 0.38 |
| 12 | 0.021 | 0.04 |
| 13 | 0.026 | 0.03 |
| 14 | 0.03 | 0.02 |
| 15 | 0.068 | 0.12 |
| 16 | 0.023 | 0.05 |
| 17 | 0.01 | 0.02 |
| 18 | 0.025 | 0.04 |
| 19 | 0.022 | 0.03 |
| 20 | 0.014 | 0.17 |
| 21 | 0.0059 | 0.03 |
| 22 | 0.021 | 0.08 |
| 23 | 0.105 | 0.04 |
| 24 | 0.008 | 0.03 |
| 25 | 0.013 | 0.03 |
| 26 | 0.022 | 0.03 |
| 27 | 0.038 | 0.03 |
| 28 | 0.03 | 0.03 |
| 29 | 0.018 | 0.05 |
| 30 | 0.021 | 0.06 |
| 31 | 0.016 | 0.04 |
| 32 | 0.013 | 0.05 |
| 33 | 0.022 | 0.02 |
| 34 | 0.016 | 0.03 |
| 35 | 0.027 | 0.05 |
| 36 | 0.031 | 0.07 |
| 37 | 0.025 | 0.03 |
| 38 | 0.007 | 0.01 |
| 39 | 0.068 | 0.02 |
| 40 | 0.072 | 0.06 |
| 41 | 0.022 | — |

Effect of $cPLA_2$ Inhibitor in Models of Thrombosis

The effect of administration of $cPLA_2$ inhibitors in models for thrombosis was determined by the following procedures.

Platelet Function Analyzer (PFA-100®) Study

Human platelet aggregation was studied using the platelet function analyzer (PFA-100®). Human blood was collected from volunteers who had denied taking any platelet inhibitory medications over the previous two weeks. Blood was collected in 3.2% sodium citrate Vacutainer tubes (Becton Dickinson). Tubes were inverted 5 times and the blood was transferred to 15 ml polypropylene conical tubes. 5 μl of respective inhibitor dissolved in 100% DMSO (4-(3-{5-chloro-1-

(diphenylmethyl)-2-[2-({[2-fluoro-6-(trifluoromethyl)benzyl]sulfonyl}amino)ethyl]-1H-indol-3-yl}propyl)benzoic acid, Example 14; 4-(3-{5-chloro-1-(diphenylmethyl)-2-[2-({[2-(trifluoromethoxy)benzyl]sulfonyl}amino) ethyl]-1H-indol-3-yl}propyl)benzoic acid, Example 25; 4-{3-[1-benzhydryl-5-chloro-2-(2-{[(3,4-dichlorobenzyl)sulfonyl]amino}ethyl)-1H-indol-3-yl]propyl}benzoic acid, Compound C) was added to 1 ml aliquot of whole human blood, to give the respective inhibitor concentration and a final DMSO concentration of 0.5%. Tubes were inverted 10 times to mix, and allowed to sit at room temperature for 10 minutes prior to run in PFA-100. The manufacturers protocol was followed for the PFA-100 using Collagen/Epinephrine cartridges (0.5% DMSO alone in whole blood gave closure times of 125+/−13.9 seconds). Maximum closure time is 300 seconds, as set by the manufacturer.

The results are shown in FIG. 1. Compound C or the compound of Example 14 or Example 25 was allowed to incubate with whole human blood prior to challenge testing in the PFA-100. All compounds were efficacious in the platelet function assay. At a concentration of 1.25 µg/ml, Compound C and the compound of Example 14 led to an increased closure time, while the compound of Example 25 was efficacious at concentrations as low as 0.3 µg/ml. These data show that these three compounds inhibit platelet aggregation in human blood, in vitro.

FeCl$_3$-Induced Model of Arterial Thrombosis

Two hours prior to induction of vascular injury, Sprague Dawley outbreed rats (80-100 gram of body weight) received 4-(3-{5-chloro-1-(diphenylmethyl)-2-[2-({[2-fluoro-6-(trifluoromethyl)benzyl]sulfonyl}amino)ethyl]-1H-indol-3-yl}propyl)benzoic acid (Example 14) or 4-(3-{5-chloro-1-(diphenylmethyl)-2-[2-({[2-(trifluoromethoxy)benzyl] sulfonyl}amino)ethyl]-1H-indol-3-yl}propyl)benzoic acid (Example 25) at a dose of 25 mg/kg by oral gavage. The total volume of gavage was 0.5 ml. The control group of animals had been treated with only vehicle. Fifteen minutes before vascular injury rats were anesthetized by an intramuscular injection of a ketamine/xylazyne mixture. Following anesthesia the left carotid artery was dissected and exposed for further measurements. For induction of prothrombotic injury, a round piece of filter paper (2 mm in diameter) soaked in 10% of FeCl$_3$ solution was applied onto the wall of the exposed vessel. After 5 minutes the filter paper was removed and the 1PRB perivasular Doppler flow probe (Transonic Systems Inc.) was secured around the carotid artery to measure blood flow. Blood flow was recorded for a total period of 30 minutes using Transonic Flow Meter (model TS420, Transonic Systems Inc.) and Windaq data acquisition software.

Figure 2:
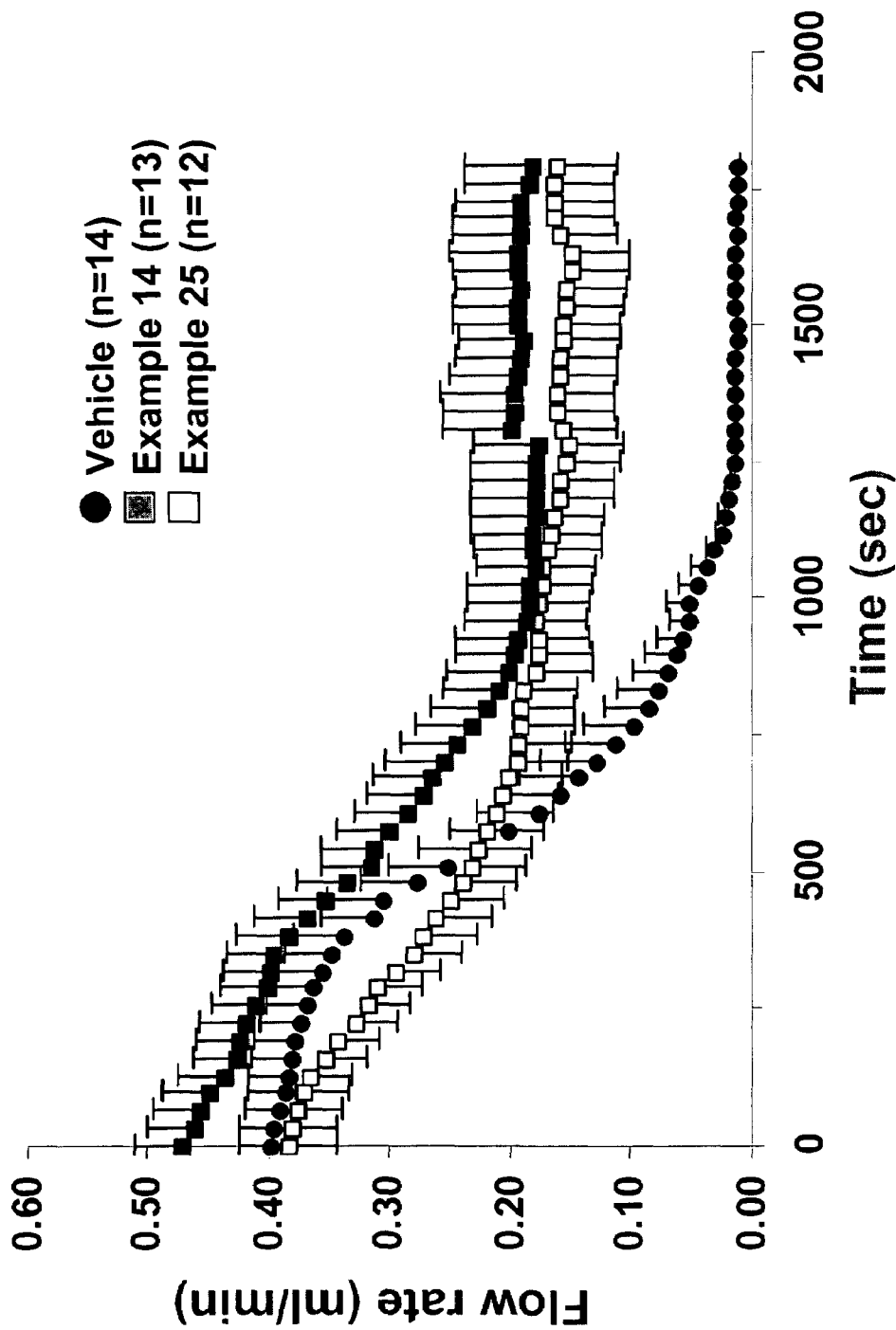
FIG. 2 shows the improved blood flow and reduction of thrombus formation by the compounds of Examples 14 and 15, in a rat model of acute thrombosis

The results, shown in FIG. 2, show that both compounds are efficacious in the rat ferric chloride thrombosis model when dosed orally at 25 mg/kg.

Thromboxane B$_2$ Levels in Rats with FeCl$_3$ Induced Thrombosis

Blood was collected from rats that were dosed with vehicle, the compound of Example 14 or the compound of Example 25, and subjected to the ferric chloride injury protocol above. Blood was collected from the vena cava and blood coagulation was allowed to take place for 1 hour at 37 degree Celsius. Serum was then isolated and serum thromboxane B2 levels were determined by ELISA.

Figure 3:
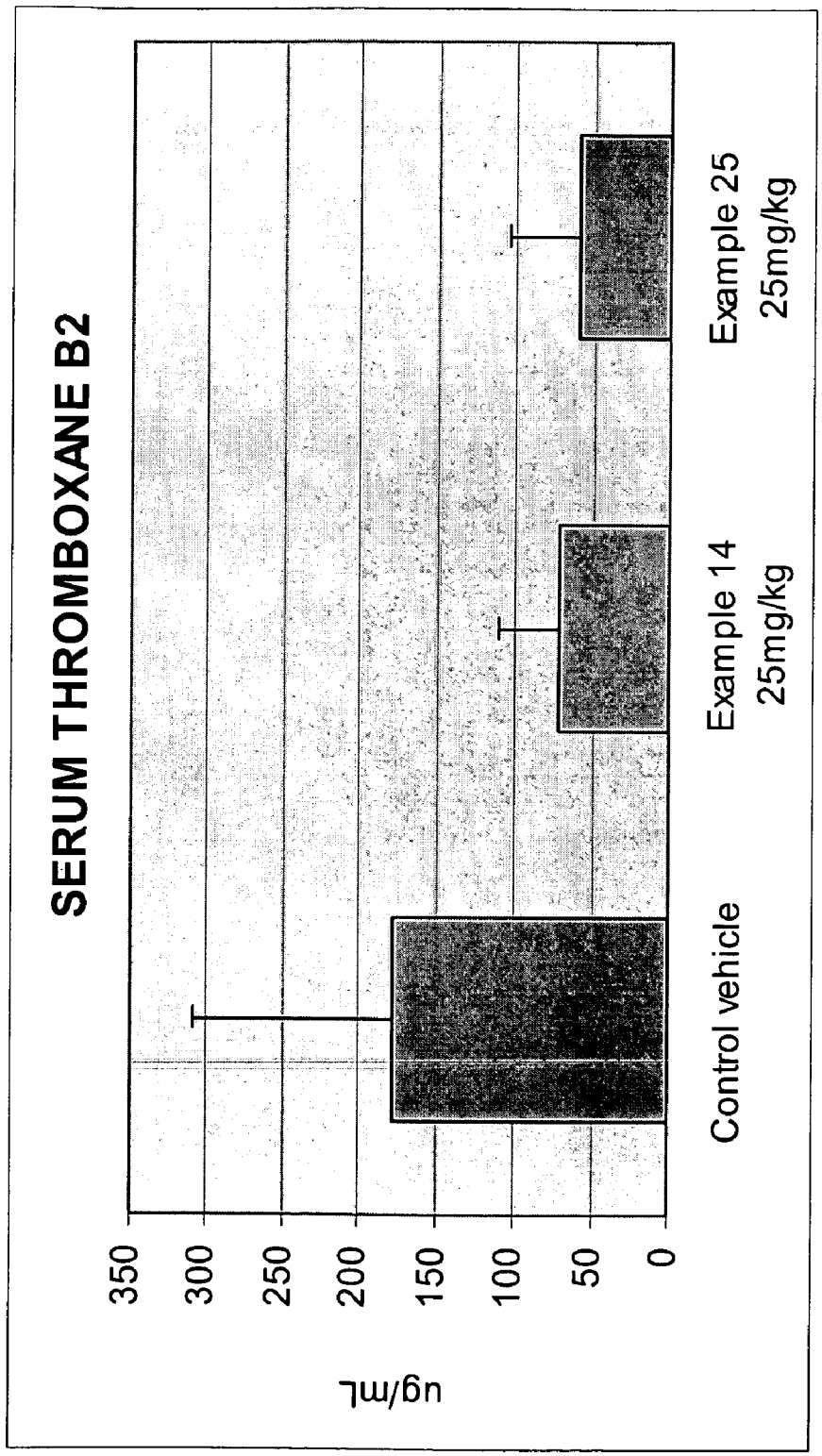
FIG. 3 shows the reduction of serum thromboxane $B_2$ levels in rats subjected to ferric chloride induced thrombosis by the compounds of Examples 14 and 25.

The results are shown in FIG. 3. These data show that both compounds provided a reduction in serum Thromboxane B$_2$ levels.

Effect of cPLA$_2$ Inhibitor in an Animal Model of Multiple Sclerosis.

The effect of administration of a cPLA$_2$ inhibitor in an animal model of multiple sclerosis was determined by the following procedure.

Six groups of B6 mice were immunized with MOG/CFA and injected with pertussis toxin to induce experimental autoimmune encephalomyelitis (EAE), an animal model of Multiple sclerosis. Three groups of mice were treated with vehicle, 4-{3-[1-benzhydryl-5-chloro-2-(2-{[(2,6-dimethylbenzyl)sulfonyl]amino}ethyl)-1H-indol-3-yl]propyl}benzoic acid Compound A), or 4-{2-[1-benzhydryl-5-chloro-2-(2-{[(3,4-dichlorobenzyl)sulfonyl]amino}-ethyl)-1H-indol-3-yl]ethoxy}benzoic acid (Compound B) from the day of immunization (orally, 100 mg/kg, twice/day). Another three groups of mice were treated with vehicle, Compound A or Compound B starting on the day of EAE onset (day 15) (orally, 100 mg/kg, twice/day). On this day, over 20% of the animals showed first clinical signs of EAE and the treatment started in all the animals in these groups. The results are shown in the Table below, wherein mean clinical score is a mean of clinical evaluation of each animal for that particular day. Animals are scored as follows:

0—no clinical signs of EAE (no paralysis)
1—paralysis of tail
2—paralysis of tail and partial hind leg paralysis
3—paralysis of tail and complete hind leg paralysis
4—paralysis of tail, complete hind leg paralysis and a partial front leg paralysis
5—moribund animal (all four limbs paralyzed, lack of responsiveness, these mice were immediately euthanized).

| Days After Immun. | Vehicle Control, Day 1 | Compound A, Day 1 | Compound B, Day 1 | Vehicle Control, Onset | Compound A, Onset | Compound B, Onset |
| --- | --- | --- | --- | --- | --- | --- |
| 11 | 0 | 0 | 0 | 0 | 0 | 0 |
| 12 | 0 | 0 | 0 | 0 | 0 | 0 |
| 13 | 0 | 0 | 0 | 0 | 0 | 0 |
| 14 | 0 | 0 | 0 | 0 | 0 | 0 |
| 15 | 0.23 | 0 | 0 | 0.37 | 0.33 | 0.10 |
| 16 | 0.50 | 0 | 0 | 0.97 | 0.60 | 0.45 |
| 17 | 0.63 | 0 | 0.06 | 1.30 | 0.80 | 0.80 |
| 18 | 0.93 | 0 | 0.06 | 1.63 | 1.03 | 1.05 |
| 19 | 1.03 | 0 | 0.11 | 1.63 | 1.13 | 1.10 |
| 20 | 1.47 | 0 | 0.39 | 2.23 | 1.50 | 1.00 |
| 21 | 1.63 | 0.06 | 0.44 | 2.40 | 1.57 | 1.20 |
| 22 | 2.13 | 0.09 | 0.50 | 2.43 | 1.60 | 1.10 |

-continued

| Days After Immun. | Vehicle Control, Day 1 | Compound A, Day 1 | Compound B, Day 1 | Vehicle Control, Onset | Compound A, Onset | Compound B, Onset |
|---|---|---|---|---|---|---|
| 23 | 2.53 | 0.16 | 0.67 | 2.47 | 1.37 | 1.40 |
| 24 | 2.73 | 0.19 | 0.56 | 2.47 | 1.43 | 1.35 |
| 25 | 2.67 | 0.25 | 0.56 | 2.30 | 1.23 | 1.25 |
| 26 | 2.73 | 0.28 | 0.56 | 2.17 | 0.87 | 1.40 |
| 27 | 2.63 | 0.38 | 0.72 | 2.17 | 0.87 | 1.55 |

In addition, the compounds of Examples 14 and 25 were also found to be efficacious in the mouse experimental autoimmune encephalomyelitis (EAE) model of multiple sclerosis. As shown by the data in the Table below, these compounds led to a delayed onset of disease and reduced severity of disease when administered orally in doses as low as 2.5 mg/kg.

| Days After Immunization | Vehicle Control | Example 14 2.5 mg/kg Day 1 | Example 25 2.5 mg/kg Day 1 |
|---|---|---|---|
| 11 | 0 | 0 | 0 |
| 12 | 0.08 | 0 | 0 |
| 13 | 0.50 | 0 | 0 |
| 14 | 1.13 | 0 | 0.14 |
| 15 | 1.48 | 0.14 | 0.20 |
| 16 | 2.00 | 0.32 | 0.55 |
| 17 | 2.00 | 0.50 | 0.55 |
| 18 | 2.19 | 0.55 | 0.55 |
| 19 | 3.31 | 1.32 | 0.84 |
| 20 | 3.48 | 1.41 | 1.27 |
| 21 | 3.60 | 1.77 | 1.68 |
| 22 | 3.60 | 1.89 | 1.89 |
| 23 | 3.58 | 2.00 | 1.93 |
| 24 | 3.60 | 2.05 | 2.00 |
| 25 | 3.71 | 1.90 | 1.98 |
| 26 | 3.71 | 1.89 | 1.95 |
| 27 | 3.71 | 1.89 | 1.93 |

These results show that treatment of mice with $cPLA_2$ inhibitors of Examples 14, 25, Compound A and Compound B can prevent EAE when administered from the time of immunization and reduce clinical severity of EAE in mice which have already developed EAE or are close to developing clinical signs of the disease.

Effect of $cPLA_2$ Inhibitor in Atherosclerosis

The effect of administration of a $cPLA_2$ inhibitor in the apolipoprotein E (ApoE) knockout mouse model of atherosclerosis was determined by the following procedure.

ApoE KO Mouse Model

The apolipoprotein E (ApoE) knockout mouse was created by gene targeting in embryonic stem cells to disrupt the ApoE gene. ApoE is a glycoprotein that is responsible for the uptake of chylomicrons and VLDL particles by the liver, thereby preventing the accumulation of cholesterol rich remnants in the blood stream. As a result of the homozygous inactivation of the ApoE gene, ApoE KO mice exhibit high levels of cholesterol, which in turn induces the formation atherosclerotic plaques in areas of singularities along the arterial tree, specifically at the aortic sinus where high hemodynamic disturbances prevail and at branching sites along the aorta.

$cPLA_2$ in Atherosclerosis

Cytosolic phospholipase A2 ($cPLA_2$) preferentially mediates the release of arachidonic acid upon cell activation. Metabolites of arachidonic acid, the eicosanoids, are recognized as important modulators of inflammatory processes. Decreased biosynthesis of pro-inflammatory eicosanoids has been shown to inhibit atherosclerotic lesion progression in humans and mice, thereby suggesting a potential role of $cPLA_2$ in atherosclerosis (see Ranke et al., Circulation 1993; 87(6) 1873-1879; Paul et al., Life Sciences 2000; 68(4):457-465; Cyrus et al., Circulation 2002; 106(10) 1282-1287; Pratico et al., PNAS 2001; 98(6): 3358-3363; Burleigh et al., Circulation 2002; 105(15): 1816-1823; Cayatte et al., ATVB 2000; 20(7): 1724-1728; Aiello et al., ATVB 2002; 22(3): 443-449; Subbanagounder et al., Circ. Res. 1999; 85(4): 311-318). In addition, $cPLA_2$ expression has been detected in human atherosclerotic arteries but not in normal healthy human arteries (see Schäfer Elinder et al., ATVB 1997; 17(10):2257-2263).

Effect of an Inhibitor of $cPLA_2$ on Atherosclerosis in Mice

Six week old male ApoE KO mice were treated with 4-{3-[1-benzhydryl-5-chloro-2-(2-{[(3,4-dichlorobenzyl)sulfonyl]amino}ethyl)-1H-indol-3-yl]propyl}benzoic acid (Compound C). Mice were fed a normal chow diet supplemented with Compound C at 1.3 mg/g and 3.3 mg/g (resulting in ~250 ng/mL and ~500 ng/mL maximum drug exposure, respectively) or vehicle for 20 weeks. Serum thromboxane B2 levels were significantly decreased after 9 and 20 weeks of treatment when compared to control animals, as shown in the table below:

| Serum Thromboxane B2 Levels | | |
|---|---|---|
| % Decrease vs Control | Compound C (1.3 mg/g) | Compound C (3.3 mg/g) |
| after 9 weeks of treatment | 52.5 | 61.2 |
| after 20 weeks of treatment | 36.6 | 49.5 |

In addition, atherosclerotic plaque burden at the aortic sinus was decreased by 32.7% (349582±132685 vs 519220±100694 $\mu m^2$, $p<0.05$) and 45.6% (282697±146462 vs 519220±100694 $\mu m^2$, $p<0.001$) in animals that were administered the compound at 1.3 mg/g and 3.3 mg/g, respectively, when compared to control animals. Further, as shown in the table below, reduction in percent lesion area along the aorta was not significant (ns), demonstrating the role of this $cPLA_2$ inhibitor in affecting disease specifically in regions of highest hemodynamic disturbances.

| Atherosclerotic Lesions Along the Aorta | | |
|---|---|---|
| | Compound C (1.3 mg/g) | Compound C (3.3 mg/g) |
| % Decrease vs Control | 32.4 ns | 35.2 ns |

As shown in the Table below, atherosclerotic lesion complexity was reduced in animals treated with Compound C when compared to control animals, as attested by increased frequency of early-stage lesions and decreased frequency of advanced stage lesions at the aortic sinus. The Table shows percent of total animals with Stage 1 (fibrofatty lesion), Stage 2 (early fibrous plaque), Stage 3 (advanced fibrous plaque), Stage 4 (stable complicated lesion) and Stage 5 (unstable complicated lesion) for animals dosed with vehicle, Compound C at 1.3 mg/g and Compound C at 3.3 mg/g.

| Athersclerotic Lesion Complexity | | | | | |
|---|---|---|---|---|---|
| | Stage 1 | Stage 2 | Stage 3 | Stage 4 | Stage 5 |
| Vehicle | | | 11% | 56% | 33% |
| Cpd. C 1.3 mg/g | | | 33% | 56% | 11% |
| Cpd. C 3.3 mg/g | 9% | 18% | 37% | 27% | 9% |

Thromboxane $B_2$ Levels in the ApoE KO Mouse Model of Atherosclerosis

ApoE KO mice were fed a normal chow diet supplemented with Compound C or the compound of Example 10 at 3.3 mg/g chow or vehicle for two days. Blood was collected through the retro-orbital siunus and left to coagulate at 37° C. for one hour. Serum was then isolated and assayed for thromboxane B2 by ELISA. Thromboxane concentrations (ng/mL) were found to be: Vehicle: 76.1±17.3; Compound C (3.3 mg/g): 33.5±11.6; Compound of Example 10: (3.3 mg/g): 1.4±0.7.

In a separate experiment, ApoE KO mice were dosed with vehicle or the compound of Example 25 at 10 mg/kg by oral gavage. Blood was collected through the retro-orbital siunus and left to coagulate at 37° C. for one hour. Serum was then isolated and assayed for thromboxane B2 by ELISA. Thromboxane concentrations (ng/mL) were found to be: Vehicle: 267.9±34.3; Compound of Example 25: 9.4±5.0.

Effect of $cPLA_2$ Inhibitor in Models of Stroke

The effect of administration of a $cPLA_2$ inhibitor in models for stroke was determined by the following procedures.

Cerebellar Granule Neuron Cultures

Primary cerebellar granule neurons were isolated from P5-8 rat pups. Briefly, cerebelli were collected and pooled in ice-cold phosphate buffer saline (PBS) without $Ca^{2+}$ and $Mg^{2+}$. The tissue was finely chopped and transferred to an enzymatic dissociation media containing 20 IU/ml papain in Earle's balanced salt solution (Worthington Biochemical, Freehold, N.J.) and incubated for 30 minutes at 37° C. After enzymatic dissociation, the papain solution was aspirated and the tissue mechanically triturated with a fire-polished Pasteur pipette in complete media [Neurobasal Medium with B-27 supplement (Gibco, Grand Island, N.Y.), penicillin/streptomycin, aphidicolin, glutamate, potassium chloride] containing 2,000 IU/ml DNase and 10 mg/ml ovomucoid protease inhibitor. Single-cell suspensions in complete media were plated on pre-coated poly-L-ornithine/laminin 24-well plates (Becton-Dickinson, Bedford, Mass.) at a density of $5.0 \times 10^5$ cells/well. Cells were maintained for two weeks prior to experimentation.

Oxygen-Glucose Deprivation (OGD) in Cultured Neurons

Cultures were treated with Compound A at various concentrations, 60 minutes before OGD. Media was removed and replaced with deoxygenated buffer in an anaerobic chamber (80% nitrogen, 10% hydrogen, 10% carbon dioxide gas mixture). Fresh Compound A, Example 34 or Example 41 was added to the cultures and maintained in the anaerobic chamber for 2 hours. At the end of the incubation, fresh media was exchanged and fresh Compound A was added. Cultures were maintained for an additional 24 hours in a normoxic incubator. Cell death was determined by measuring lactate dehydrogenase release into the media 24 hours later (Roche Biochemicals). In the table below, values are shown for the control, OGD, various concentrations of Compound A, and MK801, a NMDA receptor antagonist, which is a positive control.

| Neuroprotection by cPLA2 inhibitors Against OGD | | | | | |
|---|---|---|---|---|---|
| | Control | OGD | 0.1 μM | 0.3 μM | 1 μM | 3 μM |
| Control | | | | | | |
| Avg. | 14 | 51 | | | | |
| St. Dev, | 3 | 5 | | | | |
| Cpd. A | | | | | | |
| Avg. | | | 38 | 31 | 27 | 20 |
| St. Dev. | | | 2 | 5 | 4 | 2 |
| Ex. 34 | | | | | | |
| Avg. | | | 35 | 28 | 21 | 18 |
| St. Dev. | | | 4 | 3 | 3 | 2 |
| Ex. 41 | | | | | | |
| Avg. | | | 40 | 33 | 30 | 24 |
| St. Dev. | | | 6 | 4 | 5 | 4 |

It can be seen from these data that administration of Compound A, the compound of Example 34, or the compound of Example 41 was effective in protecting cultured neurons from OGD-induced cell death. At concentrations as low as 0.1 μM, statistically significant reduction in percent cell death was observed for these compounds.

Effect of $cPLA_2$ Inhibitor in Models of Parkinson's Disease

The effect of administration of a $cPLA_2$ inhibitor in a model for Parkinson's Disease was determined by the following procedures.

Dopaminergic Neuron Cultures

Primary dopaminergic neurons were isolated from E15 rat embryos as described in Pong K., et al., (1997) J. Neurochem. 69 986-994. Briefly, the ventral mesencephalon was isolated and tissue was pooled in ice-cold phosphate buffer saline (PBS) without $Ca^{2+}$ and $Mg^{2+}$. The tissue was transferred to an enzymatic dissociation media containing 20 IU/ml papain in Earle's balanced salt solution (Worthington Biochemical, Freehold, N.J.) and incubated for 30 minutes at 37° C. After enzymatic dissociation, the papain solution was aspirated and the tissue mechanically triturated with a fire-polished Pasteur pipette in complete media [Neurobasal Medium with B-27 supplement (Gibco, Grand Island, N.Y.), penicillin/streptomycin, aphidicolin, glutamate] containing 2,000 IU/ml DNase and 10 mg/ml ovomucoid protease inhibitor. Single-cell suspensions in complete media were plated on pre-coated poly-L-ornithine/laminin 24-well plates (Becton-Dickinson, Bedford, Mass.) at a density of $5.0 \times 10^5$ cells/well. Cells were maintained for one week prior to experimentation.

$MPP^+$ Exposure in Dopaminergic Neurons

Cultures were treated with various concentrations of Compound A, Compound B, Compound C and GDNF (glial-cell line derived neurotrophic factor, a positive control) hours before exposure to the neurotoxin $MPP^+$, the toxic metabolite of MPTP. Cultures were exposed to 10 µM $MPP^+$ for 60 minutes. After the exposure, fresh media was exchanged and fresh compound was added. Dopaminergic neuron viability was determined 24 hours later by measuring $^3H$-dopamine uptake as described in Pong et al., 1997, supra. The results are shown in the Table below:

| | Neuroprotectin by cPLA2 inhibitors against $MPP^+$ | | | | |
|---|---|---|---|---|---|
| | Control | 10 µM MPI | 0.3 µM | 1 µM | 3 µM | 10 µM |
| Avg. Cpd. A | 100 | 56.6 | | | | |
| St. Dev, | 8.2 | 2.2 | | | | |
| Avg. Cpd. B | | | 76.9 | 83.4 | 78.8 | 81.1 |
| St. Dev. | | | 3.4 | 5.7 | 3.3 | 6.4 |
| Avg. Cpd. C | | | 74 | 71.6 | 78.6 | 83.2 |
| St. Dev. | | | 3 | 2 | 5.5 | 5.1 |
| Avg. | | | 68.6 | 70.6 | 75.9 | 79.6 |
| St. Dev. | | | 3.8 | 3.6 | 2.6 | 1.3 |

It can be seen from these data that administration of these compounds were effective to protect dopaminergic neuron viability against $MPP^+$.

Effects of $cPLA_2$ Inhibitor in Models of Osteoarthritis, Rheumatoid Arthritis and Pain In vivo pharmacology studies using the compound of Example 10 were conducted to demonstrate the effectiveness of oral administration in models of inflammation and peripheral pain including the carrageenan paw edema model (See Winter, C. A., et al., *Proc Soc Exp Biol Med* 1962; 111:544-547), the collagen induced arthritis model (See Trentham, D. E., et al., *J Exp. Med* 146; 828-833), and the Complete Freund's Adjuvant (CFA)-induced model of hyperalgesia (See Stein C, et al., *Pharmacology Biochemistry & Behavior*, 1988; 31:445-451). The in vivo inhibition of prostaglandins and leukotrienes was also measured in the CFA-challenged paws in the hyperalgesia model.

Carrageenan Paw Edema Assay

The carrageenan paw edema assay is an acute model of inflammation that is particularly useful for in vivo assessment of compounds that effect the production of prostaglandins. In particular, NSAIDs inhibit edema in a characteristic dose response fashion in this model, and the activity of NSAIDs in this model correlates well with the activity observed in man (See Mukherjee A, et al., *Inflamm Res.* 1996; 45:531-540). Therefore, the compound of Example 10 was tested in the carrageenan paw edema model. In this model, the compound was administered orally 2 hours before sub-plantar injection of carrageenan and the inhibition of paw swelling was determined over the next three hours. Paw edema was statistically significantly decreased at doses as low as 3 mg/kg and an approximate ED50 (based on a maximal inhibition of 50%) was determined to be 7.5 mg/kg.

These data demonstrate that compound of Example 10 works in a classic model of in vivo inflammation that has been used to predict the effectiveness of both NSAIDs and COX-2 inhibitors.

Effect of Compound of Example 10 in the Collagen-Induced Arthritis Model

The compound of Example 10 was tested in the mouse CIA model, which has many immunologic and pathologic similarities to human rheumatoid arthritis (See Trentham, D. E., et al., supra). Arthritis was induced in DBA/1LacJ mice by intradermal injection of an emulsion of bovine type II collagen and CFA followed by a boost with an intradermal injection of bovine type II collagen emulsified in incomplete Freund's Adjuvant 21 days after the initial immunization. Compound efficacy was assessed in a semi-therapeutic dosing regimen that was initiated when 10% of the animals showed disease symptoms. At that point animals were randomly assigned to treatment groups and administered the compound of Example 10 (100 mg/kg) PO BID for 28 days. Control groups received celecoxib, vehicle alone or were left untreated. All animals were scored daily in a blinded fashion for visual signs of disease symptoms.

The mean scores of the group treated with the compound of Example 10 were compared to the vehicle-control group values using the Student's t-test. During treatment starting on day 10, the group treated with the compound of Example 10 (100 mg/kg BID) showed a statistically significant decrease in the disease severity scores in all experiments; and the number of animals without disease symptoms was greatest in the groups that were treated with the compound of Example 10.

After completion of the experiments, paws were processed for histology. Two board certified veterinary pathologist evaluated the slides in a blinded fashion. Each paw was assigned a numerical score for both arthritis severity and the general number of joints affected. Mice treated with the compound of Example 10 (100 mg/kg BID) had the lowest group mean severity scores and the highest percentage of unaffected (grade 0) paws; vehicle-treated and untreated mice had the highest group mean severity scores and the highest combined percentage of grade 3 and grade 4 affected paws. Mice treated with the compound of Example 10 (100 mg/kg) had an average severity grade of 0.9/2.1 (pathologist 1/pathologist 2) whereas vehicle treated animals had an average severity score of 2.1/3.0. Similar results were seen in an additional experiment at 100 mg/kg.

Effect of Compound of Example 10 in Rat Hyperalgesia Models

The sensitivity of peripheral sensory neurons can be enhanced such that they respond to both noxious and non-noxious stimuli resulting in chronic pain (See Julius, D. et al., *Nature*. 2001; 413:203; Woolf, C. J., et al., *Science*. 200; 288:1765). Prostaglandins and leukotrienes at the site of inflammation and tissue damage are partially responsible for this potentiation of the pain response. Prostaglandins promote the phosphorylation of ion channels, increasing the excitability and lowering the pain threshold of sensory neurons. Analogously, leukotriene $B_4$ and related arachidonate metabolites of 12-LO bind to and activate the capsaicin receptor (or $VR_1$) ion channel on neurons that respond to heat and low pH (See Piomelli D., *TRENDS in Pharmacological Sciences*, January 2001; 22(1):17-29). The effect of the compound of Example 10 was measured in the CFA-induced hyperalgesia model, and lipid mediator production was measured at peripheral and central sites.

The animals were dosed with vehicle, the compound of Example 10, naproxen or celecoxib, and then CFA was immediately injected into the hind footpad. To assess hyperalgesia, pressure was applied to the left hind paw at a slow and constant rate using a digital force gauge. Measurements were taken at 0 and 6 hours. The application of the force was stopped when the animal vocalized, or struggled. Readings were taken prior to dosing and CFA injection, and repeated six hours after the CFA injection. Two independent experiments were run and the data were analyzed separately. The compound of Example 10 appeared to provide a statistically significant decrease in pain compared to the vehicle control group at 25 mg/kg.

The paws were collected at the end of each experiment (6 hours) and the levels of $PGE_2$, $LTB_4$ and $TXB_2$ were measured in the exudates. $PGE_2$ levels in the paw were significantly inhibited by the compound of Example 10 (at 25 mg/kg) and by the celecoxib and naproxen controls. $TXB_2$ levels were also significantly inhibited by celecoxib, however, the inhibition with the compound of Example 10 and naproxen was greater than the inhibition with celecoxib, suggesting a COX-1 dependent component to the synthesis. As expected, $LTB_4$ levels were significantly inhibited by the compound of Example 10, but there was evidence of substrate shunting to the 5-lipoxygenase pathway as levels actually increased with naproxen and celecoxib.

In summary, the compound of Example 10 was active in models of osteoarthritis, rheumatoid arthritis and pain. The compound significantly inhibited edema at a dose of 3 mg/kg and was at 50% of the maximum effect at ~7.5 mg/kg in the carrageenan paw edema model. Daily treatment with the compound of Example 10 (100 mg/kg BID) for 28 days produced a significant reduction of disease in the semi-therapeutic collagen-induced arthritis model based on both clinical and histological assessment. The compound was also effective at 25 mg/kg in the CFA model of hyperalgesia.

The compound of Example 10 was also effective at inhibiting the production of both prostaglandins and leukotrienes using in vivo models. The production of COX-2 dependent PGE2, COX-1 dependent Thromboxane and 5-LO dependent leukotriene B4 was inhibited in paws challenged with CFA.

Effect of Compound of Example 10 in Rodent and Sheep Models of Asthma

Asthma has been defined as a chronic inflammatory disorder of the airways in which many cells and cellular elements play a role. In susceptible individuals this inflammation causes recurrent or persistent episodes of wheezing, breathlessness, chest tightness and coughing, particularly at night or in the early morning. These episodes are usually associated with widespread but variable airflow obstruction that often resolves spontaneously or with treatment. The inflammation also causes an associated increase in the existing bronchial hyperresponsiveness to a variety of stimuli. Preclinical models of asthma have provided insight into the underlying mechanisms of disease pathology and have been instrumental in the development of asthma therapeutics. In particular, rodent models of allergen-induced pulmonary inflammation are useful for in vivo assessment of compounds that inhibit the inflammation associated with allergic asthma and have been used extensively to evaluate the efficacy of glucocorticoids, leukotriene receptor antagonists, 5-LO inhibitors, and phosphodiesterase 4 inhibitors (See Kumar, R. K. et al, *J Pharmacol Exp Ther.* 2003; 307:349-355; Wu, A. Y. et al. *Clin Exp Allergy.* 2003; 33:359-366; Bell, R. L. et al., *J Pharmacol Exp Ther* 1997; 280:1366-1373; and Henderson, W. R., Jr., et al., *J Exp Med.* 1996; 184:1483-1494).

The compound of Example 10 was tested in both rat and mouse models of allergen-induced pulmonary inflammation.

In addition to the allergen induced pulmonary inflammation models in rodents, allergen induced changes in lung function are often evaluated in allergic sheep. *Ascaris* sensitized sheep that are challenged via the airways with *Ascaris suum* antigen exhibit features of reversible airway narrowing and AHR. Studies performed in this animal model present strong evidence that the release of arachidonic acid metabolites plays an important role in the development of late bronchial responses to antigen challenge (See Abraham, W. M., et al, *Respiration.* 1989; 56:48-56). Thus, the compound of Example 10 was evaluated for effects on allergen induced changes in lung function in a sheep model of asthma.

Rat Antigen Induced Pulmonary Inflammation Model

The efficacy of the compound of Example 10 was evaluated in a Brown Norway rat model in which ovalbumin (OVA)-sensitized animals were challenged via the airways with an aerosol of ovalbumin (OVA) on days 1 and 2. OVA sensitized rats were challenged via aerosol on day 1 and day 2. The compound of Example 10 was administered at 30 mg/kg PO BID 1 hour prior to challenge and 10 hours after challenge over the 2 day challenge period. Dexamethasone was administered at 3 mg/kg IP 1 hour prior to challenge on day 1 and day 2. Animals were sacrificed on day 3 and bronchoalveolar cavities lavaged for analysis of cellular influx. Oral BID administration at 30 mg/kg over the 2 day challenge period statistically significantly inhibited Bronchoalveolar lavage fluid (BALF) eosinophil influx in 8 out of 8 independent studies. The compound of Example 10 also statistically significantly attenuated the total numbers of inflammatory cells within the BALF at the dose tested but had no significant effect on the influx of lymphocytes or neutrophils in this model.

Effect of Compound of Example 10 in a Sheep Model of Antigen-Induced Early and Late-Phase Bronchoconstriction and AHR Allergen-induced reversible airway narrowing and AHR are two hallmark features of allergic asthma that can be examined in vivo in a sheep model of asthma. Studies performed in this animal model present strong evidence that the release of arachidonic acid metabolites plays an important role in the development of late bronchial responses to antigen challenge (See Abraham, W. M., et al., *Respiration.* 1989; 56:48-56). The release of leukotrienes through the LO pathway during the acute bronchial constriction after inhalation of *Ascaris suum* antigen represents the key factor for the initiation of the subsequent events, namely the late-phase response and the bronchial hyperreactivity. The 5-LO inhibitor zileuton blocks antigen-induced late airway responses, inflammation, and AHR in this model, whereas a continuous IV infusion of the selective $LTD_4$ receptor antagonist, montelukast, attenuates both the early and late-phase asthmatic responses (See Abraham, W. M., et al., *Eur J Pharmacol* 1992; 217:119-126; Jones, T. R. et al., *Can J Physiol Pharmacol.* 1995; 73:191-201). In addition, oral administration of a dual $LTD_4/TXB_2$ inhibitor can inhibit both the early and late-phase response, as well as AHR to carbachol and histamine (See Abraham, W. M., et al., *J Pharmacol Exp Ther.* 1988; 247:1004-1011). PAF has also been implicated in the late-phase response in this model providing further support for the concept that a more complete blockade of lipid mediators by a $cPLA_2\alpha$ antagonist may provide better clinical efficacy compared with current anti-leukotrienes (See Abraham, W. M., et al., *J Appl Physiol*. 1989; 66:2351-2357).

The compound of Example 10 was administered at 3 mg/kg BID (PO) 24 h prior to challenge, 2 h prior to challenge and 8 hr post challenge. The mean % increase in airway resistance for 3 individual sheep over the ensuing 8 h period was determined. Complete blockade of the late asthmatic response was observed The following day, airway hyperresponsiveness (AHR) was assessed in these same treated sheep by determining the cumulative carbachol concentration that increased specific lung resistance by 400%. Treatment with the compound of Example 10 resulted in complete blockade of airway hyperresponsiveness. In an extended dosing regimen, compound of Example 10 was administered at 3 mg/kg PO BID for 4 days before challenge, 2 hours before challenge on the fifth day and 8 hr post challenge.

The mean % increase in airway resistance for 5 individual sheep over the ensuing 8 h period was determined, and in this more extended dose regimen, there was a modest but statistically significant inhibition of the early asthmatic response in addition to a complete blockade of the late-phase response and a complete blockade of AHR to aerosolized carbachol.

The foregoing data show that the compound of Example 10 is a potent inhibitor of allergen induced pulmonary inflammation, bronchoconstriction and AHR in animal models of asthma.

The compounds of the invention inhibit cPLA2 activity that is required for supplying arachidonic acid substrate to cyclooxygenase-1 or 2 and 5-lipoxygenase, which in turn initiate the production of prostaglandins and leukotrienes respectively. In addition, $cPLA_2$ activity is essential for producing the lyso-phospholipid that is the precursor to PAF. Thus these compounds are useful in the treatment and prevention of disease states in which leukotrienes, prostaglandins or PAF are involved. Moreover, in diseases where more than one of these agents plays a role, a $cPLA_2$ inhibitor would be expected to be more efficacious than leukotriene, prostaglandin or PAF receptor antagonists and also more effective than cyclooxygenase or 5-lipoxygenase inhibitors.

Therefore, the compounds, pharmaceutical compositions and regimens of the present invention are useful in treating and preventing the disorders treated by cyclooxygenase-2, cyclooxygenase-1, and 5-lipoxygenase inhibitors and also antagonists of the receptors for PAF, leukotrienes or prostaglandins. Diseases treatable by compounds of this invention include but are not limited to: pulmonary disorders including diseases such as asthma, chronic bronchitis, and related obstructive airway diseases; allergies and allergic reactions such as allergic rhinitis, contact dermatitis, allergic conjunctivitis, and the like; inflammation such as arthritis or inflammatory bowel diseases, skin disorders such as psoriasis, atopic eczema, acne, UV damage, burns and dermatittis; cardiovascular disorders such as atherosclerosis, angina, myocardial ischaemia, hypertension, platelet aggregation, and the like; and renal insufficiency induced by immunological or chemical. The drugs may also be cytoprotective, preventing damage to the gastrointestinal mucosa by noxious agents. The compounds will also be useful in the treatment of adult respiratory distress syndrome, endotoxin shock and ischeamia induced injury including myocardial or brain injury.

The methods of treatment, inhibition, alleviation or relief of asthma of this invention include those for Extrinsic Asthma (also known as Allergic Asthma or Atopic Asthma), Intrinsic Asthma (also known as Nonallergic Asthma or Nonatopic Asthma) or combinations of both, which has been referred to as Mixed Asthma. The methods for those experiencing or subject to Extrinsic or Allergic Asthma include incidents caused by or associated with many allergens, such as pollens, spores, grasses or weeds, pet danders, dust, mites, etc. As allergens and other irritants present themselves at varying points over the year, these types of incidents are also referred to as Seasonal Asthma. Also included in the group of Extrinsic Asthmas is bronchial asthmas and allergic bronchopulminary aspergillosis.

Intrinsic Asthmas that may be treated or alleviated by the present methods include those caused by infectious agents, such as cold and flu viruses in adults and respiratory syncytial virus (RSV), rhinovirus and influenza viruses common in children. Also included are the asthma conditions which may be brought about in some asthmatics by exercise and/or cold air. The methods are useful for Intrinsic Asthmas associated with industrial and occupational exposures, such as smoke, ozone, noxious gases, sulfur dioxide, nitrous oxide, fumes, including isocyanates, from paint, plastics, polyurethanes, varnishes, etc., wood, plant or other organic dusts, etc. The methods are also useful for asthmatic incidents associated with food additives, preservatives or pharmacological agents. Common materials of these types are food coloring such as Tartrazine, preservatives like bisulfites and metabisulfites, and pharmacological agents such as aspirin and non-steroidal anti-inflammatory agents (NSAIDs). Also included are methods for treating, inhibiting or alleviating the types of asthma referred to as Silent Asthma or Cough Variant Asthma.

A further method of treatment of asthma of this invention comprises administering to a mammal in need of such treatment a pharmaceutically effective amount of a compound of this invention, as described above, and a pharmaceutically effective amount of one or more additional anti-asthma agents.

Anti-asthma agents useful with these combinations include long-term-control medications, such as corticosteroids (glucocorticoids), cromolyn sodium (disodium cromoglycate—DSCG), nedocromil, methylxanthines (such as theophylline) and leukotriene modifiers. Useful leukotriene modifiers include leukotriene receptor antagonists, such as zafirlukast (ACCOLATE®) and monetlukast (SINGULAIR®), and 5-lipoxygenase inhibitors, such as zileuton (ZYFLO®). Useful corticosteroids include inhaled products, such as Beclomethasone dipropionate, Budesonide, Flunisolide, Fluticasone, and Triamcinolone, as well as the pharmaceutically acceptable salt forms thereof. Also useful are systemic corticosteroids such as prednisone, prednisolone and methylprednisolone.

Also useful are quick-relief anti-asthma medications, such as long-acting $beta_2$-agonists, short-acting $beta_2$-agonists, anticholinergics and systemic corticosteroids. β-Adrenergic agents which may be used include epinephrine, isoproterenol, metaproterenol, terbutaline, isoetharine, albuterol, bitolterol and perbuterol. Useful anticholinergic agents include atropine (and its derivative ipatropium bromide) and glycopyrrolate. The compounds of this invention may also be used to treat asthma in conjunction with allergy immunotherapies, which also referred to in the art as hyposensitization therapies. These compounds may be administered according to the dosages and regimens known in the art.

Additional anti-asthma agents which may be used in the combinations of this invention include pranlukast, anakinra, seratrodast, olopatadine hydrochloride, cromoglicate lisetil, ramatroban, interleukin-4 receptor (Immunex), urodilatin, colforsin daropate, salbutamol, LCB-2183, andolast, ciclesonide, budesonide, formoterol, omalizumab, tranilast, saredutant, CDP-835 (anti-IL-5 Mab), fexofenadine HCl, N-(1-(Chlorophenyl)-1-methylethyl)-3-(imidazol-1-yl)propylaminedihydrochloride (BTS-71-321), cilomilast, bimosiamose, Corticotropin-releasing factor, clenoliximab, tiotropium bromide, 2 H-1,2-Benzoselenazine, 3,4-dihydro-4,4-dimethyl (BXT-51072), atreleuton, (R)-salbutamol, 8-Methoxyquinoline-5-(N-(2,5-dichloropyridin-3-yl)) carboxamide (D-4418), triamcinolone acetonide, KW-4490 (KF-19514), LAX-300 (LX-109), IDEC-152 (ST-152; anti-CD23 antibody), cytokine Traps, anandamide, SRL-172, salmeterol+Fluticasone, KCA-757, 2-Pyridinecarboxylic acid, 6-(2-(3,4-diethoxyphenyl)-4-thiazolyl)-(OPC-6535), PM-56D9, salbutamol, CT-2820 (PDEIV inhibitors), beclometasone, nepadutant, ketotifen fumarate, DHEAS (PB-005), Pharmaprojects No. 5163, No. 5278 and No. 5297, salbutamol sulfate, EPI-2010 (EpiGenRx), mepolizumab, Benzamide, N-(5-(3-((4-chlorophenyl)sulfonyl)propyl)-2-(1H-tetrazol-5-ylmethoxy)phenyl)-3-((4-(1,1-dimethylethyl)-2-thiazolyl)methoxy)-, monosodium salt (YM-158), 2-(4-ethoxycarbonylaminobenzyl)-6-(3,4-dimethoxyphenyl)-2,3,4,5-tetrahydro-pyridazin-3-one Pharmaprojects (No. 5450), Sch-205528, L-826141 (Pharmaprojects No. 5477), Budesonide, duramycin, 4,4-Bis(4-(quinolin-2-ylmethoxy)phenyl)pentanoic acid sodium salt (VML-530), IL-9 inhibitor, beclometasone dipropionate, formoterol, cyclo(MePhe-Leu-Asp-Val-D-Arg-D-Arg) (ZD-7349), salbutamol, Ethanaminium, 2-(((2-acetyl-4-((1-oxohexadecyl) amino) phenoxy) hydroxyphosphinyl)oxy)-N, N,N-trimethyl-, inner salt (CPR-2015), PD-168787 (CI-1018), cathepsin S inhibitors, SB-240683 (anti-IL-4 Mab), BIIL-284, APC-2059, budesonide+formoterol, Bay-16-9996 (IL-4 antagonist), beclometasone, GW-328267, VLA-4 antagonists, 4-hydroxy-1-methyl-3-octyloxy-7-sinapinoylamino-2(1 H)-quinolinone (TA-270), CpG-7909 (ProMune), DNK-333A (Pharmaprojects No. 6070), AWD-12-281, LM-1507 (LM-1484), formoterol, MOL-6131, cathepsin S inhibitors, CS-615, ibudilast, 2-{N-(4-(4-Chlorophenylsulfonylamino) butyl)-N-{3-(2-(4-cyclobutylthiazol-2-yl)ethyl) benzyl}sulfamoyl}benzoic acid (S-36527), and 2-{N-(4-(4-Chlorophenylsulfonylamino)butyl)-N-{3-((4-isopropylthiazol-2-yl)methyloxy) benzyl}sulfamoyl}benzoic acid (S-36496).

The methods herein are also useful for treatment and alleviation of Intrinsic Asthma associated with gastroesophageal reflux (GERD), which can stimulate bronchoconstriction. GERD, along with retained bodily secretions, suppressed cough, and exposure to allergens and irritants in the bedroom can contribute to asthmatic conditions and have been collectively referred to as Nighttime Asthma or Nocturnal Asthma. In methods of treatment, inhibition or alleviation of asthma associated with GERD, a pharmaceutically effective amount of the compounds of this invention may be used as described herein in combination with a pharmaceutically effective amount of an agent for treating GERD. These agents include, but are not limited to, proton pump inhibiting agents like PROTONIX® brand of delayed-release pantoprazole sodium tablets, PRILOSEC® brand omeprazole delayed release capsules, ACIPHEX® brand rebeprazole sodium delayed release tablets or PREVACID® brand delayed release lansoprazole capsules.

The compounds of this invention can be used as an antipyretic agent. The compounds of this invention may be utilized in methods of treating pain, particularly the pain associated with inflammation. Specific methods include, but are not limited to, those for treating centrally mediated pain, peripherally mediated pain, musculo-skeletal pain, lumbosacral pain, structural or soft tissue injury related pain, progressive disease related pain, such as oncology and degenerative disorders, neuropathic pain, which can include both acute pain, such as acute injury or trauma, pre and post-surgical, migraine pain, dental pain, etc., chronic pains, such as neuropathic pain conditions of diabetic peripheral neuropathy, post-herpetic neuralgia and fibromyalgia, and inflammatory conditions such as osteoarthritis or rheumatoid arthritis, sequela to acute injury or trauma and cancer-related pain.

The compounds of this invention can be used to alleviate, inhibit, relieve and/or treat arthritic disorders in a mammal including, but not limited to, rheumatoid arthritis, spondyloarthropathies, gouty arthritis, infectious arthritis, osteoarthritis (which includes erosive osteoarthritis and is also known as osteoarthrosis or degenerative joint disease or DJD), systemic lupus erythematosus and juvenile arthritis. Each of these methods comprises administering to a mammal in need of such action a pharmaceutically effective amount of a substituted indole of this invention, as described herein, or a pharmaceutically acceptable salt or ester form thereof.

In addition, the compounds of this invention can be used to alleviate, inhibit, relieve and/or treat arthritic conditions associated with spondylitis, including ankylosing spondylitis, reactive arthritis (Reiter's syndrome), psoriatic arthritis, arthritis associated with chronic inflammatory bowel disease and AIDS-related seronegative spondyloarthropathy.

This invention also provides methods for treating, alleviating or inhibiting rheumatic disease and disorders. These methods are useful for treatment of systemic lupus erythematosus, systemic sclerosis and forms of scleroderma, polymyositis, dermatomyositis, necrotizing vasculitis and other vasculopathies, hypersensitivity vasculitis (including Henoch-Schönlein purpura), Wegener's granulomatosis, Giant cell arteritis, mucocutaneous lymph node syndrome (Kawasaki disease), Behcet's syndrome, Cryoglobulinemia, juvenile dermatomyositis, Sjögren's syndrome, overlap syndromes (includes mixed connective tissue disease), polymyalgia rheumaticqa, erythema nodosum, relapsing polychondritis, tendonitis (tenosynovitis), Bicipital tendenitis, bursitis, Olecranon bursitis, adhesive capsulitis of the shoulder (frozen shoulder) trigger finger, and Whipple's disease.

The methods of this invention are also useful for treatment, alleviation or inhibition of metabolic and endocrine diseases with rheumatic states, including gout, pseudogout, chondrocalcinosis, amyloidosis, scurvy, speicific enzyme deficiency states (including Fabry's disease, alkaptonuria, ochonosisi, Lesch-Nyhan syndrome, and Gaucher's disease), hyperlipoproteinemias (types II, IIa, IV), Ehlers-Danlos syndrome, Marfan's syndrome, pseudoxanthoma elasticum, Wilson's disease. Also treatable with the present methods are the rheumatic states associated with endocrine diseases, such as diabetes mellitus, acromegaly, hyperparathyroidism, myositis ossificans progressiva, hypermobility syndromes, arthrogryposis multiplex congenita, and thyroid diseases such as thyroiditis, hypothyroidism and hyperthyroidism. These methods may also be used for rheumatic conditions associated with neoplasms such as primary neoplasms (synovioma), metastatic neoplasms, multiple myeloma, leukemia and lymphomas, pigmented villonodular synovitis, osteochondromatosis and others. Also included among the methods of this invention are relief from the rheumatic conditions associated with neuropathic disorders including, Charcot's joints, hand-arm vibration syndrome (also known as vibration-induced white finger or Raynaud's phenomenon), repetitive stress syndromes, reflex sympathetic dystrophy and compression neuropathies, such as peripheral entrapment (including carpal tunnel syndrome, pronator syndrome, thoracic outlet syndromes and tarsal tunnel syndrome), radiculopathy and spinal stenosis.

This invention further provides a method of alleviation, inhibition, relief or treatment of arthritic disorders in a mammal, the method comprising administering to a mammal in need thereof a pharmaceutically effective amount of a chemical inhibitor of phospholipase enzymes, particularly phospholipase $A_2$ enzymes, as defined herein and a pharmaceutically effective amount of an anti-rheumatic agent.

Combinations for the treatment of arthritic disorders may include commercially available anti-rheumatic agents such as, but not limited to, naproxen, which is commercially available in the form of EC-NAPROSYN® delayed release tablets, NAPROSYN®, ANAPROX® and ANAPROX® DS tablets and NAPROSYN® suspension from Roche Labs, CELEBREX® brand of celecoxib tablets, VIOXX® brand of rofecoxib, CELESTONE® brand of betamethasone, CUPRAMINE® brand penicillamine capsules, DEPEN® brand titratable penicillamine tablets, DEPO-MEDROL brand of methylpredhisolone acetate injectable suspension, ARAVA™ leflunomide tablets, AZULFIDIINE EN-tabs® brand of sulfasalazine delayed release tablets, FELDENE® brand piroxicam capsules, CATAFLAM® diclofenac potassium tablets, VOLTAREN® diclofenac sodium delayed release tablets, VOLTAREN®-XR diclofenac sodium extended release tablets, ENBREL® etanerecept products, (should we add other biologics use in RA) and other commercially available antirheumatic agents.

Also useful are GENGRAF™ brand cyclosprine capsules, NEORAL® brand cyclosprine capsules or oral solution, IMURAN® brand azathioprine tablets or IV injection, INDOCIN® brand indomethacin capsules, oral suspension and suppositories, PEDIAPED® prednisolone sodium phosphate oral solution, PLAQUENIL® brand hydroxychloroquine sulfate, PRELONE® brand prednisolone syrup, REMICADE® infliximab recombinant for IV injection, and SOLU-MEDROL® methylprednisolone sodium succinate for injection.

Also useful in the combinations of this invention are gold compounds and products useful in the treatment of arthritis and rheumatic conditions, such as auranofin or MYOCHRISYINE® gold sodium thiomalate injection.

Each of these products may be administered according to the pharmaceutically effective dosages and regimens known in the art, such as those described for the products in the Physicians' Desk Reference, 55 Edition, 2001, published by Medical Economics Co., Inc., Montvale, N.J.

The compounds of this invention may also be administered in the methods of this invention with analgesic and anti-inflammatory agents such as NSAIDs and aspirin and other salicylates. Examples of useful agents include ibuprofen (MOTRIN®, ADVIL®), naproxen (NAPROSYN®), sulindac (CLINORIL®, diclofenac (VOLTAREN®), piroxicam (FELDENE®) ketoprofen (ORUDIS®), diflunisal (DOLOBID®), nabumetone (RELAFEN®), etodolac (LODINE®), oxaprozin (DAYPRO®), indomethacin (INDOCIN®), melicoxam (MOBICOX®), valdecoxib and eterocoxib. Aspirin is anti-inflammatory when given in high doses, otherwise it is just a pain killer like acetaminophen (TYLENOL®).

Suitable cyclooxygenase 2 (COX-2) inhibitors—for use with the methods of this invention include, but are not limited to, 2-(4-ethoxy-phenyl)-3-(4-methanesulfonyl-phenyl)-pyrazolo[1,5-b]pyridazine, CDC-501, celecoxib, COX-189, 4-(2-oxo-3-phenyl-2,3-dihydrooxazol-4-yl)benzenesulfonamide, CS-179, CS-502, D-1367, darbufelone, DFP, DRF-4367, flosulide, JTE-522 (4-(4-cyclohexyl-2-methyl-5-oxazolyl)-2-fluorobenzenesulfonamide), L-745337, L-768277, L-776967, L-783003, L-791456, L-804600, meloxicam, MK663 (etoricoxib), nimesulide, NS-398, parecoxib, 1-Methylsulfonyl-4-(1,1-dimethyl-4-(4-fluorophenyl)cyclopenta-2,4-dien-3-yl)benzene, 4-(1,5-Dihydro-6-fluoro-7-methoxy-3-(trifluoromethyl)-(2)-benzothiopyran o(4,3-c)pyrazol-1-yl)benzenesulfonamide, 4,4-dimethyl-2-phenyl-3-(4-methylsulfonyl)phenyl)cyclobutenone, 4-Amino-N-(4-(2-fluoro-5-trifluoromethyl)-thiazol-2-yl)-benzene sulfonamide, 1-(7-tert-butyl-2,3-dihydro-3,3-dimethyl-5-benzo-furanyl)-4-cyclopropyl butan-1-one, Pharmaprojects No. 6089 (Kotobuki Pharmaceutical), RS-1 13472, RWJ-63556, S-2474, S-33516, SC-299, SC-5755, valdecoxib, UR-8877, UR-8813, UR-8880. Further suitable COX-2 inhibitors for use according to the invention include parecoxib, MK663, 4-(4-cyclohexyl-2-methyl-5-oxazolyl)-2-fluorobenzenesulfonamide (JTE-522), nimesulide, flosulide, DFP and 2-(4-ethoxy-phenyl)-3-(4-methanesulfonyl-phenyl)-pyrazolo[1,5-b]pyridazine, and their physiologically acceptable salts, esters or solvates.

Such compositions are also useful in the treatment of menstrual cramps, preterm labor, tendonitis, bursitis, allergic neuritis, cytomegalovirus infection, apoptosis, including HIV-induced apoptosis, lumbago, liver disease including hepatitis.

The methods are also useful in treating gastrointestinal conditions such as inflammatory bowel disease, Crohn's disease, gastritis, irritable bowel syndrome and ulcerative colitis and for the prevention of treatment of cancer such as colorectal cancer. The compounds and compositions of the present invention are also useful for the prevention or treatment of benign and malignant tumors/neoplasia including cancers such as colorectal cancer, brain cancer, bone cancer, epithelial cell-derived neoplasia (epithelial carcinoma) such as basal cell carcinoma, adenocarcinoma, gastrointestinal cancer, including lip cancer, mouth cancer, esophogeal cancer, small bowel cancer and stomach cancer, colon cancer, liver cancer, bladder cancer, pancreatic cancer, ovarian cancer, cervical cancer, lung cancer, breast cancer, and skin cancers, such as squamous cell and basal cell cancers, prostate cancer, renal cell carcinoma, and other known cancers that effect epithelial cells throughout the body. Neoplasias for which compositions of the invention are contemplated to be particularly useful are gastrointestinal cancer, Barrett's esophagus, liver cancer, bladder cancer, pancreas cancer, ovarian cancer, prostatic cancer, cervical cancer, lung cancer, breast cancer, and skin cancer, such as squamous cell and basal cell cancers. The compounds and methods of this invention can also be used to treat the fibrosis occurring with radiation therapy. Such compositions can be used to treat subjects having adenomatous polyps, including those with familial adenomatous polyposis (FAP). Additionally, such compositions can be used to prevent polyps from forming in patients at risk of FAP. Compounds of this invention are useful in the treatment of cancers because of their anti-angiogenic effects.

Further uses include treating inflammation in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like. Also included are treatments of ophthalmic diseases, such as retinitis, conjunctivitis, retinopathies, uveitis, ocular photophobia, and of acute injury to the eye tissue. The compounds of this invention will be useful in the treatment of post-operative inflammation including that following ophthalmic surgery such as cataract surgery or refractive surgery. Also included are treatments of pulmonary and upper respiratory tract inflammation, such as that associated with viral infections and cystic fibrosis, and in bone resorption such as that accompanying osteoporosis. These compounds and compositions are useful for the treatment of certain central nervous system disorders, such as cortical dementias including Alzheimer's disease, neurodegeneration, and central nervous system damage resulting from stroke, ischemia and trauma. The compounds of this invention may also be useful in the treatment of Parkinson's disease.

Methods of treating pain comprise administering to a mammal subject to such pain a pharmaceutically effective amount of a compound of this invention alone or in combination with one or more additional pharmaceutically effective agents for the treatment of pain or inflammation or the related underlying medical condition. Examples of drug agents which may be combined with the present compounds are analgesics, anti-angiogenic agents, anti-neoplastic agents, These compounds may also be combined with anti-epileptic compounds that have pain alleviating properties, such as gabapentin and pregabalin.

One such combination method of this invention comprises administering to a mammal in need thereof a pharmaceutically effective amount of a compound of this invention and a pharmaceutically effective amount of a nontoxic N-methyl-D-aspartate (NMDA) receptor antagonist and/or an agent that blocks at least one major intracellular consequence of NMDA receptor activation. Examples of NMDA receptor antagonists useful in these methods include dextromethorphan, dextrorphan, amantadine and memantine, or the pharmaceutically acceptable salts thereof.

Another method herein of treating inflammation and inflammatory disorders comprises the co-administration to a mammal in need thereof of an inhibitor of induced nitric oxide synthase with a compound of this invention. Administration of this combination is useful for prophylactic or therapeutic administration in a mammal experiencing or subject to an abnormally low level of nitric oxide synbthase (NOS) activity, particularly those subject to hypertension or an elevated risk of pulmonary hypertension, ischemic stroke, myocardial infarction, heart failure, progressive renal disease, thrombosis, reperfusion injury, or a nervous system degenerative disorder, such as Alzheimer's disease, or those chronically exposed to hypoxic conditions.

The methods of this invention also include those for treating or preventing a neoplasia disorder in a mammal, including a human, in need of such treatment or prevention. The method comprises treating the mammal with a therapeutically effective amount of a compound of this invention in combination with an MMP inhibitor. These two components may further be optionally combined with one or more agents selected from an antiangiogenesis agent, an antineoplastic agent, an adjunctive agent, an immunotherapeutic agent, an analgesic agent; and/or a radiotherapeutic agent. One such multiple component therapy comprises administering to the mammal in need thereof a compound of this invention, a matrix metalloproteinase inhibitor and an antineoplastic agent.

The methods and combinations of this invention may be used for the treatment or prevention of neoplasia disorders including acral lentiginous melanoma, actinic keratoses, adenocarcinoma, adenoid cyestic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, chorioid plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial. squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adenocarcinoma, pineal cell, pituitary tumors, plasmacytoma, pseudosarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor.

Antineoplastic agents useful in the combination therapies herein include anastrozole, calcium carbonate, capecitabine, carboplatin, cisplatin, Cell Pathways CP-461, docetaxel, doxorubicin, etoposide, fluorouracil, fluoxymestrine, gemcitabine, goserelin, irinotecan, ketoconazole, letrozol, leucovorin, levamisole, megestrol, mitoxantrone, paclitaxel, raloxifene, retinoic acid, tamoxifen, thiotepa, topotecan, toremifene, vinorelbine, vinblastine, vincristine, selenium (selenomethionine), ursodeoxycholic acid, sulindac sulfone, exemestane and eflornithine (DFMO), 1-[4-(2-Azepan-1yl-ethoxy)-benzyl]-2-(4-hydroxy-phenyl)-3-methyl-1H-indol-5-ol (also known as TSE-424) and 2-(4-Hydroxy-phenyl)-3-methyl-1-(4-(2-piperidin-1-yl-ethoxy)-benzyl]-1H-indol-5-ol (also known as ERA-923).

This invention also includes methods of utilizing the compounds herein in combination with a proteinaceous interleukin-1 inhibitor, such as an IL-1 receptor antagonist (IL-Ira), for preventing or treating inflammatory diseases in a mammal. Acute and chronic interleukin-1 (IL-1)-mediated inflammatory diseases of interest in these methods include, but is not limited to acute pancreatitis; ALS; Alzheimer's disease; cachexia/anorexia; asthma; atherosclerosis; chronic fatigue syndrome, fever; diabetes (e.g., insulin diabetes); glomerulonephritis; graft versus host rejection; hemohorragic shock; hyperalgesia, inflammatory bowel disease; inflammatory conditions of a joint, including osteoarthritis, psoriatic arthritis and rheumatoid arthritis; ischemic injury, including cerebral ischemia (e.g., brain injury as a result of trauma, epilepsy, hemorrhage or stroke, each of which may lead to neurodegeneration); lung diseases (e.g., ARDS); multiple myeloma; multiple sclerosis; myelogenous (e.g., AML and CML) and other leukemias; myopathies (e.g., muscle protein metabolism, esp. in sepsis); osteoporosis; Parkinson's disease; pain; pre-term labor; psoriasis; reperfusion injury; septic shock; side effects from radiation therapy, temporal mandibular joint disease, tumor metastasis; or an inflammatory condition resulting from strain, sprain, cartilage damage, trauma, orthopedic surgery, infection or other disease processes.

This invention also provides a method of administering one or more of the compounds of this invention to a female in need thereof to substantially prevent or reducing changes in the female's reproductive system associated with onset or continuation of labor. Also provided is a method of substantially preventing or reducing uterine contractility either occurring during pregnancy or associated with menorrhagia. These methods may optionally include coadministration of a compound of this invention with a progestogen, a progestin or a progestational agent.

Cytosolic phospholipase $A_2\alpha$ ($cPLA_2\alpha$) is a ubiquitously expressed enzyme that preferentially mediates the release of arachidonic acid upon cell activation. Bioactive metabolites of arachidonic acid, the eicosanoids, are recognized as important modulators of platelet signaling. Inhibitors of the eicosanoid pathway (e.g. aspirin) reduce the formation of thromboxane $A_2$ ($TXA_2$), a labile and potent platelet agonist, resulting in depression of platelet function, thrombus formation, and proven clinical benefit in reducing morbidity and mortality.

The compounds of the invention inhibit $cPLA_2$ activity that is required for supplying arachidonic acid substrate to cyclooxygenase-1 or 2 and 5-lipoxygenase, which in turn initiate the production of prostaglandins and leukotrienes respectively. In addition, $cPLA_2$ activity is essential for producing the lyso-phospholipid that is the precursor to PAF. Thus these compounds are useful in the treatment and prevention of disease states in which leukotrienes, prostaglandins or PAF are involved. Moreover, in diseases where more than one of these agents plays a role, a $cPLA_2$ inhibitor would be expected to be more efficacious than leukotriene, prostaglandin or PAF receptor antagonists and also more effective than cyclooxygenase or 5-lipoxygenase inhibitors.

Therefore, the compounds, pharmaceutical compositions and regimens of the present invention are useful in treating and preventing the disorders treated by cyclooxygenase-2, cycloxygenase-1, and 5-lipoxygenase inhibitors and also antagonists of the receptors for PAF, leukotrienes or prostaglandins.

This invention also provides methods for treating or preventing venous or arterial thrombosis in a mammal, or preventing progression of symptoms of thrombosis, the method comprising administering to a mammal in need thereof a pharmaceutically acceptable amount of a compound of the invention, or a pharmaceutically acceptable salt thereof. In some embodiments, the thrombosis is atherothrombosis.

Each of the methods of this invention comprises administering to a mammal in need of such treatment a pharmaceutically or therapeutically effective amount of a compound of this invention. In the instances of combination therapies described herein, it will be understood the administration further includes a pharmaceutically or therapeutically effective amount of the second pharmaceutical agent in question. The second or additional pharmacological agents described herein may be administered in the doses and regimens known in the art.

The compounds of this invention may also be used in comparable veterinary methods of treatment, particularly for the veterinary treatment, inhibition or alleviation of inflammation and pain. These methods will be understood to be of particular interest for companion mammals, such as dogs and cats, and for use in farm mammals, such as cattle, horses, mules, donkeys, goats, hogs, sheep, etc. These methods may be used to treat the types of inflammation and pain experienced in veterinary medicine including, but not limited to, pain and inflammation associated with arthritis, joint imperfections, developmental joint defects, such as hip dysplasia, tendonitis, suspensary ligament inflammation, laminitis, curb and bursitis, or pain or inflammation associated with surgery, accident, trauma or disease, such as Lyme Disease. These compounds may also be used in the treatment of inflammation of the air passages, such as in conditions of asthma, laryngitis, tracheitis, bronchitis, rhinitis and pharyngitis Each of these veterinary methods comprises administering to the mammal in need thereof a pharmaceutically effective amount of a compound of this invention, or a pharmaceutically acceptable salt form thereof. The compounds of this invention may be used for human or veterinary methods in conjunction with other medicaments or dietary supplements known in the art for the treatment, inhibition or alleviation of inflammation or pain. These may include aspirin (including buffered aspirin, aspirin with Maalox and enteric coated aspirin), COX-2 inhibitors, such as celecoxib, non-acetylated carboxylic acids, such as magnesium salicylate, salicylamide or sodium salicylate, acetic acids, such as doclofenac or etodolac, propionic acids, such as ibuprofen, naproxen (available in NAPROSYNO® and EQUIPROXEN® brands), ketoprofen, RIMADYL® (carprofen), flunixin meglumine, fenamic acids, such as tolfenamic acid, mefanamic acid, meclofenamic acid (ARQUEL®) or niflumic acid, enolic acids, such as oxyphenbutazone, phenylbutazone, piroxicam or dipyrone, or non-acidic compounds like nabumetone. Also used in veterinary applications are dimethylsulfoxide (DMSO), orgotein (such as PALOSEIN® brand of orgotein), polysulfated glycosaminoglycans or PS-GAGs (such as ADEQUAN® brand polysulfated glycosaminoglycan), hyaluronic acid and its natural and synthetic analogues, Ketorolac trimethamine (such as the TORADOL® brand), FELDENE® (piroxicam), or METACAM® (meloxicam).

Dietary supplements used in human or veterinary applications include glucosamines, chondroitin sulfate, methylsulfonylmethane (MSM), and omega 3 fatty acids and other cold water fish oils. The compounds and methods of this invention may also be used in conjunction with human or veterinary physical therapy, massage, chiropractic and accupuncture treatments and regimens. Each of these medicaments and dietary supplements may be administered to the mammal in question using regimens and effective dosages known in the art.

It is intended that each of the patents, applications, and printed publications including books mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. 3-{4-[(2-{5-chloro-1-(diphenylmethyl)-2-[2-({[2-(trifluoromethyl)benzyl]sulfonyl}amino)ethyl]-1H-indol-3-yl}ethyl)sulfonyl]phenyl}propanoic acid, or a pharmaceutically acceptable salt thereof.

2. A pharmaceutical composition comprising 3-{4-[(2-{5-chloro-1-(diphenylmethyl)-2-[2-({[2-(trifluoromethyl)benzyl]sulfonyl}amino)ethyl]-1H-indol-3-yl}ethyl)sulfonyl]phenyl}propanoic acid, or a pharmaceutically acceptable salt thereof, and a pharmaceutically acceptable carrier.

* * * * *